(12) United States Patent
Lynch et al.

(10) Patent No.: US 7,560,477 B2
(45) Date of Patent: *Jul. 14, 2009

(54) COMPOUNDS ACTIVE IN SPHINGOSINE 1-PHOSPHATE SIGNALING

(75) Inventors: Kevin R. Lynch, Charlottesville, VA (US); Timothy L. Macdonald, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/748,296

(22) Filed: May 14, 2007

(65) Prior Publication Data

US 2007/0219163 A1    Sep. 20, 2007

Related U.S. Application Data

(62) Division of application No. 10/523,337, filed as application No. PCT/US03/023768 on Jul. 30, 2003, now Pat. No. 7,241,790.

(60) Provisional application No. 60/425,595, filed on Nov. 12, 2002, provisional application No. 60/399,545, filed on Jul. 30, 2002.

(51) Int. Cl.
*A61K 31/417* (2006.01)
*C07D 233/64* (2006.01)

(52) U.S. Cl. .................... 514/400; 548/340.1

(58) Field of Classification Search ............ 548/112, 548/335.1, 335.5, 340.1; 514/396, 400, 92, 514/93, 94, 95, 98, 99

See application file for complete search history.

(56) References Cited

U.S. PATENT DOCUMENTS

| | | | |
|---|---|---|---|
| 4,939,130 | A | 7/1990 | Jaeggi et al. |
| 5,405,988 | A | 4/1995 | Klar et al. |
| 6,069,251 | A | 5/2000 | Thurkauf et al. |
| 6,875,757 | B2 | 4/2005 | Miller et al. |
| 7,060,697 | B2 | 6/2006 | Marsilje et al. |
| 7,064,217 | B2 | 6/2006 | Macdonald et al. |
| 7,241,790 | B2 | 7/2007 | Lynch et al. |
| 2004/0224941 | A1 | 11/2004 | Seko et al. |
| 2005/0032744 | A1 | 2/2005 | Michaelis et al. |
| 2005/0043386 | A1 | 2/2005 | Nishi et al. |
| 2005/0107345 | A1* | 5/2005 | Doherty et al. ............ 514/114 |
| 2005/0107447 | A1 | 5/2005 | Lynch et al. |
| 2006/0135786 | A1 | 6/2006 | Saha et al. |
| 2006/0223866 | A1 | 10/2006 | Evindar et al. |
| 2007/0088002 | A1 | 4/2007 | Lynch et al. |
| 2007/0191313 | A1 | 8/2007 | Beard et al. |

FOREIGN PATENT DOCUMENTS

| | | |
|---|---|---|
| DE | 1 056 139 B | 4/1959 |
| DE | 3544373 A1 | 6/1987 |
| EP | 1 553 091 A1 | 7/2005 |
| GB | 950388 | 2/1964 |
| JP | 2002-316985 | 10/2002 |
| WO | WO 99/35259 | 7/1999 |
| WO | WO 01/60819 A1 | 8/2001 |
| WO | WO 01/71022 A2 | 9/2001 |
| WO | WO 02/064616 A2 | 8/2002 |
| WO | WO 02/076995 A2 | 10/2002 |
| WO | WO 02/092068 A1 | 11/2002 |
| WO | WO 03/059880 A1 | 7/2003 |

(Continued)

OTHER PUBLICATIONS

Bandini, M. et al., "An Effective and Useful Synthesis of Enantiomerically Enriched Arylglycinols", *Eur. J. Chem.* 2001, 1937-1942.

(Continued)

*Primary Examiner*—Kamal A Saeed
*Assistant Examiner*—Kristin Bianchi
(74) *Attorney, Agent, or Firm*—IPLM Group, P.A.

(57) ABSTRACT

The present invention relates to S1P analogs that have activity as S1P receptor modulating agents and the use of such compounds to treat diseases associated with inappropriate S1P receptor activity. The compounds have the general structure:

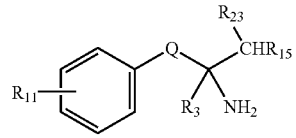

wherein $R_{11}$ is $C_5$-$C_{18}$ alkyl or $C_5$-$C_{18}$ alkenyl;
Q is $C_3$-$C_6$ optionally substituted cycloalkyl, $C_3$-$C_6$ optionally substituted heterocyclic, $C_3$-$C_6$ optionally substituted aryl $C_3$-$C_6$ optionally substituted heteroaryl or —NH(CO)—;
$R_3$ is H, $C_1$-$C_4$ alkyl, ($C_1$-$C_4$ alkyl)OH or ($C_1$-$C_4$ alkyl)$NH_2$;
$R_{23}$ is H or $C_1$-$C_4$ alkyl, and
$R_{15}$ is hydroxy, phosphonate, or

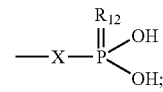

wherein X and $R_{12}$ is O or S;
or a pharmaceutically acceptable salt or tautomer thereof.

15 Claims, 14 Drawing Sheets

FOREIGN PATENT DOCUMENTS

| WO | WO 03/061567 A2 | 7/2003 |
|---|---|---|
| WO | WO 2004/010949 A2 | 2/2004 |
| WO | WO2004/010987 A2 | 2/2004 |
| WO | WO 2004/017917 A2 | 3/2004 |
| WO | WO 2004/024673 A1 | 3/2004 |
| WO | WO 2004/028521 A2 | 4/2004 |
| WO | WO 2004/103306 A2 | 10/2004 |
| WO | WO 2004/096752 A1 | 11/2004 |
| WO | WO 2004/103279 A2 | 12/2004 |
| WO | WO 2005/032465 A2 | 4/2005 |
| WO | WO 2005/041899 A2 | 5/2005 |
| WO | WO 2006/001463 A1 | 1/2006 |
| WO | WO 2006/020951 A1 | 2/2006 |
| WO | WO 2006/063033 A2 | 6/2006 |
| WO | WO 2006/088944 A1 | 8/2006 |
| WO | WO 2007/085451 A2 | 8/2007 |
| WO | WO 2007/086001 A2 | 8/2007 |
| WO | WO 2007/091396 A1 | 8/2007 |

OTHER PUBLICATIONS

Beilstein, XP-002380276.

Bertus, P. et al., "New and easy route to primary cyclopropylamines from nitriles", *Chem Commun*, 2001, 1792-1793.

Brinkmann, V. et al., "FTY720: Altered Lymphocyte Traffic Results in Allograft Protection" *Transplantation* 72, 2001, 764-769.

Brinkmann, V. et al., "The Immune Modulator FTY720 Targets Sphingosine 1-Phophate Receptors" *J Biol Chem* 277, 2002, 21453-21457.

Burger, A. et al., "1-Methyl-2-phenylcyclopropylamine", *Journal of Medicine and Pharmaceutical Chemistry*, vol. 4, No. 3, 1961.

Chiba, K. et al., "FTY720, a Novel Immunosuppressant, Induces Sequestration of Circulating Mature Lymphocytes by Acceleration of Lymphocyte Homing in Rats. I. FTY720 Selectively Decreases the Number of Circulating Mature Lymphocytes by Acceleration of Lymphocyte Homing", *J Immunol* 160, 1998, 5037-5044.

Choi, D. et al., "Synthesis and Anticonvulsant Activities of N-Benzyl-2-acetamidopropionamide", *J Med Chem* 39, 1996, 1907-1916.

Clair, T. et al., "Autotaxin Hydrolyzes Sphingosylphophorylcholine to Produce the Regulator of Migration, Sphingosine-1-Phosphate", *Cancer Res* 63, 2003, 5446-5453.

Clemens, J. et al., "Synthesis of *Para*-Alkyl Aryl Amide Analogues of Sphingosine-1-phosphate: Discovery of Potent S1P Receptor Agonists", *Bioorg Med Chem Lett* 13, 2003, 3401-3404.

Clemens, J. et al., "Synthesis of 4(5)-phenylimidazole-based analogs of sphingosine-1-phosphate and FTY720: Discovery of potent $S1P_1$ receptor agonists", *Bioorganic & Medicinal Chemistry Letters* 15, 2005, 3568-3572.

Crosignani, S. et al., "4-Naphthyl-Substituted Bis(Oxazoline): a New Easily Recoverable and Efficient Chiral Ligand in Asymmetric Catalysis of the Diels-Alder Reaction", *Tetrahedron* 54, 1998, 15721-15730.

Davis, M. et al., "Sphingosine 1-Phosphate Analogs as Receptor Antagonists", *The Journal of Biological Chemistry*, vol. 280, No. 11, 2005, 9833-9841.

Forrest, M. et al., "Immune Cell Regulation and Cardiovascular Effects of Sphingosine 1-Phophate Receptor Agonists in Rodents are Mediated via Distinct Receptor Subtypes", *J Pharmacol Exp Ther* 309, 2004, 758-768.

Foss, F. et al., "Synthesis, stability, and implications of phosphothioate agonists of sphingosine-1-phosphate receptors", *Bioorganic & Medicinal Chemistry* 15, 2005, 4470-4474.

Foss, F. et al., "Synthesis and biological evaluation of γ-aminophosphonates as potent, subtype-selective sphingosine 1-phosphate receptor agonists and antagonists", *Bioorganic & Medicinal Chemistry* 15, 2007, 663-677.

Fujino, M. et al., "Amelioration of Experimental Autoimmune Encephalomyelitis in Lewis Rats by FTY720 Treatment", *J Pharmacol Exp Ther* 305, 2003, 70-77.

Graler, M. H. et al., "The immunosuppressant FTY720 down-regulates sphingosine 1-phosphate G-protein-coupled receptors", *FASEB* 18, 2004, 551-553.

Hale, Jeffrey J. et al., " Potent S1P receptor agonists replicate the pharmacologic actions of the novel immune modulator FTY720", *Bioorganic & Medicinal Chemistry Letters* 14, 2004, 3351-3355.

Hale, J. J. et al., "Selecting against $S1P_3$ enhances the acute cardiovascular tolerability of 3-(n-benzyl)aminopropylphosphonic acid S1P receptor agonists", 2004 *Bioorg Med Chem Lett* 14, 2004, 3501-3505.

Hale, J. J. et al., "The discovery of 3-(N-alkyl)aminopropylphosphonic acids as potent S1P receptor agonists", (2004) *Bioorg Med Chem Lett* 14, 3495-3499.

Hale, J. J. et al., "A Rational Utilization of High-Throughput Screening Affords Selective, Orally Bioavailable 1-Benzyl-3-carboxyazetidine Sphingosine-1-phophate-1 Receptor Agonists", *J Med Chem*, 2004, 47, 6662-6665.

Hanessian, S. et al., Constrained azacyclic analogues of the immunomodulatory agent FTY720 as molecular probes for sphingosine 1-phosphate receptors:, *Bioorganic & Medicinal Chemistry Letters* 17, 2007, 491-494.

Hoshino, Y. et al., "FTY720, A Novel Immunosuppressant, Shows a Synergetic Effect in Combination With FK 506 in Rat Allograft Models", (1999) *Transplant Proc* 31, 1224-1226.

Im, D. S. et al., "Characterization of a Novel Sphingosine 1-Phosphate", (2000) *J Biol Chem* 275, 14281-14286.

Im, D. S. et al., "Characterization of the Human and Mouse Sphingosine 1-Phosphate Receptor, $S1P_5$ (Edg-8): Structure—Activity Replationship of Sphingosine 1-Phosphate Receptors", Biochemistry 40, 2001, 14053-14060.

Jones, L. et al., Rapid Solution and Solid Phase Synthesis of Oligo (1,4-phrenylene ethynylene)s with Thioester Termini: Molecular Scale Wires with Alligator Clips. Derivation of Iterative Reation Efficiencies on a Polymer Support, (1997) *J Org Chem* 62, 1388-1410.

Kaiser, C. et al., "2-Substituted Cyclopropylamines. I. Derivatives and Analogs of 2-Phenylcyclopropylamine", XP009032189, Nov. 1962, 1243-1265.

Kawasaki, K. et al., "Enantioselective Allylic Oxidation of Cycloalkenes by Using Cu(II)-Tris(oxazoline) Complex as a Catalyst", *Tetrahedron*, vol. 53, No. 18, 1997, 6337-6350.

Kharel, Y. et al., "Sphingosine Kinase 2 Is Required for Modulation of Lymphocyte Traffic by FTY 720", *J Bio Chem*, vol. 280, No. 44, Nov. 4, 2005, 36865-36872.

Kimura, T. et al., High-Density Lipoprotein Stimulates Endothelial Cell Migration and Survival Through Sphingosine 1-Phosphate and Its Receptors:, (2003) *Arterioscler Thromb Vasc Biol* 23, 1283-1288.

Kiuchi, M. et al., "Synthesis and Immunosuppressive Activity of 2-Substituted 2-Aminopropane-1,3-diols and 2-Aminoethanols[1,2]",(2000) *J Med Chem* 43, 2946-2961.

Kon, J. et al., "Comparison of Intrinsic Activities of the Putative Sphingosine 1-Phosphate Receptor Subtypes to Regulate Several Signaling Pathways in Their cDNA-transfected Chinese Hamster Ovary Cells", (1999) *J Biol Chem* 274, 23940-23947.

Lee, M. J. et al., "Sphingosine-1-Phosphate as a Ligand for the G Protein-Coupled Receptor EDG-1", (1998) *Science* 279, 1552-1555.

Lew, M. J. et al., "Analysis of competitive agonist-antagonist interactions by nonlinear regression", (1995) *Trends Pharmacol Sci* 16, 328-337.

Li, Z. et al., "Discovery of Potent 3,5-Diphenyl-1,2,4-oxadiazole Sphingosine-1-phosphate-1 ($S1P_1$) Receptor Agonists with Exceptional Selectivity against $S1P_2$ and $S1P_3$,", *Journal of Medicinal Chemistry*, vol. 48, No. 20, Oct. 6, 2005, 6169-6173.

Maki, T. et al., "Prevention of Autoimmune Diabetes By FTY720 in Nonobese Diabetic Mice", (2002) *Transplantation* 74, 1684-1686.

Maki, T. et al., "Prevention and Cure of Autoimmune Diabetes in Nonobese Diabetic Mice by Continuous Administration of FTY720", (2005) *Transplantation* 79, 1051-1055.

Mandala, S. et al., "Alteration of Lymphocyte Trafficking by Sphingosine 1-Phosphate Receptor Agonists", (2002) *Science* 296, 346-349.

Matloubian, M. et al., "Lymphocyte egress from thymus and peripheral lymphoid organs is dependent on S1P receptor 1",(2004) *Nature* 427, 355-360.

Sanchez, T. et al., "Phosphorylation and Action of the Immunomodulator FTY720 Inhibits Vascular Endotheliel Cell Growth Factor-induced Vascular Permeability", (2003) *J Biol Chem* 278, 47281-47290.

Sanna, M. G. et al., "Sphingosine 1-Phosphate (S1P) Receptor Subtypes $S1P_1$ and $S1P_3$, Respectively, Regulate Lymphocyte Recirculation and Heart Rate",(2004) *J Biol Chem* 279, 13839-13848.

Sanna, M. G. et al., "Enhancement of capillary leakage and restoration of lymphocyte egress by a chiral $S1P_1$ antagonist in vivo", *Nature Chemical Biology*, vol. 2, Aug. 2006, 434-441.

Suzuki, S. et al., "Immunosuppressive effect of a drug, FTY720, on lymphocyte responses in vitro and cardiac allograft survival in rats" (1996) *Transpl Immunol* 4, 252-255.

Van Brocklyn, J. R. et al., "Sphingosine, 1-Phosphate-induced Cell Rounding and Neurite Retraction are Mediated by the G Protein-coupled Receptor H218", (1999) *J Biol Chem* 274, 4626-4632.

Vogler, R. et al., "Sphingosine-1-Phosphate and Its Paradoxical Effects on Critical Parameters of Cutaneous Wound Healing", *The Journal of Investigative Dermatology*, vol. 48, No. 20, 2005, 6169-6173.

Xie, J. H. et al., "Sphingosine-1-Phosphate Receptor Agonism Impairs the Efficiency of the Local Immune Response by Altering Trafficking of Naive and Antigen-Activated $CD4^+$ T Cells", (2003) *J Immunol* 170, 3662-3670.

Yanagawa, Y. et al., "The significance of timing of FTY720 administration on the immunosuppressive effect to prolong rat skin allograft survival" (2000) *Int J Immunopharmacol* 22, 597-602.

Yanagawa, Y. et al., FTY720, a Novel Immunosuppressant Prolongs Rat Skin Allograft Survival by Decreasing T-Cell Infiltration Into Grafts (1999) *Transplant Proc* 31, 1227-1229.

Yang, Z., et al. "The immune modulator FYT720 prevents autoimmune diabetes in nonobese diabetic mice", (2003) *Clin Immunol* 107, 30-35.

Zhang, T. et al., "Concurrent Overexpression of Cyclin D1 and Cyclin-dependent Kinase 4 (Cdk4) in Intestinal adenomas from Multiple Intestinal Neoplasia Mice and Human Familial Adenomatous Polyposis Patients", (1997) *Cancer Res 57*, 169-175.

Zhang, Y. H. et al., "Sphingosine-1-Phosphate Via Activation of a G-Protein-Coupled Receptor(s) Enhances the Excitability of Rat Sensory Neurons", *J Neurophysiol* 96, 2006, 1042-1052.

Zhang, Y. H. et al., "Intracellular sphingosine 1-phosphate mediates the increased excitability produced by nerve growth factor in rat sensory neurons", *J Physiol 575.1*, 2006, 101-113.

\* cited by examiner

COMPOUNDS ACTIVE IN SPHINGOSINE 1-PHOSPHATE SIGNALING

RELATED APPLICATIONS

This application is a divisional application of U.S. application Ser. No. 10/523,337, filed Jan. 28, 2005, now U.S. Pat. No. 7,241,790, which is a national stage filing of International Patent Application Ser. No. PCT/US2003/023768 filed on 30 Jul. 2003, which claims priority from U.S. patent application Ser. No. 10/523,337, filed Jan. 28, 2005, U.S. Provisional Application Ser. No. 60/399,545, filed Jul. 30, 2002, and U.S. Provisional Application Ser. No. 60/425,595, filed Nov. 12, 2002, the disclosures of which are incorporated herein by reference.

US GOVERNMENT RIGHTS

This invention was made with United States Government support under Grant No. NIH R01 GM52722 and NIH R01 CA88994 awarded by National Institutes of Health. The United States Government has certain rights in the invention.

BACKGROUND

Sphingosine-1-phosphate (S1P) has been demonstrated to induce many cellular effects, including those that result in platelet aggregation, cell proliferation, cell morphology, tumor-cell invasion, endothelial cell chemotaxis and endothelial cell in vitro angiogenesis. For these reasons, S1P receptors are good targets for therapeutic applications such as wound healing and tumor growth inhibition. Sphingosine-1-phosphate signals cells in part via a set of G protein-coupled receptors named S1P1, S1P2, S1P3, S1P4, and S1P5 (formerly Edg-1, Edg-5, Edg-3, Edg-6, and Edg-8, respectively). These receptors share 50-55% identical amino acids and cluster with three other receptors (LPA1, LPA2, and LPA3 (formerly Edg-2, Edg-4 and Edg-7)) for the structurally-related lysophosphatidic acid (LPA).

A conformational shift is induced in the G-Protein Coupled Receptor (GPCR) when the ligand binds to that receptor, causing GDP to be replaced by GTP on the α-subunit of the associated G-proteins and subsequent release of the G-proteins into the cytoplasm. The α-subunit then dissociates from the βγ-subunit and each subunit can then associate with effector proteins, which activate second messengers leading to a cellular response. Eventually the GTP on the G-proteins is hydrolyzed to GDP and the subunits of the G-proteins reassociate with each other and then with the receptor. Amplification plays a major role in the general GPCR pathway. The binding of one ligand to one receptor leads to the activation of many G-proteins, each capable of associating with many effector proteins leading to an amplified cellular response.

S1P receptors make good drug targets because individual receptors are both tissue and response specific. Tissue specificity of the S1P receptors is desirable because development of an agonist or antagonist selective for one receptor localizes the cellular response to tissues containing that receptor, limiting unwanted side effects. Response specificity of the S1P receptors is also of importance because it allows for the development of agonists or antagonists that initiate or suppress certain cellular responses without affecting other responses. For example, the response specificity of the S1P receptors could allow for an S1P mimetic that initiates platelet aggregation without affecting cell morphology.

Sphingosine-1-phosphate is formed as a metabolite of sphingosine in its reaction with sphingosine kinase and is stored in abundance in the aggregates of platelets where high levels of sphingosine kinase exist and sphingosine lyase is lacking. S1P is released during platelet aggregation, accumulates in serum and is also found in malignant ascites. Biodegradation of S1P most likely proceeds via hydrolysis by ectophosphohydrolases, specifically the sphingosine 1-phosphate phosphohydrolases.

The physiologic implications of stimulating individual S1P receptors are largely unknown due in part to a lack of receptor type selective ligands. Therefore there is a need for compounds that have strong affinity and high selectivity for S1P receptor subtypes. Isolation and characterization of S1P analogs that have potent agonist or antagonist activity for S1P receptors has been limited due to the complication of synthesis derived from the lack of solubility of S1P analogs. The present invention is directed to a series of compounds that are active at S1P receptors.

SUMMARY OF THE INVENTION

One embodiment of the present invention is directed to novel sphingosine-1-phosphate analogs, compositions comprising such analogs, and methods of using such analogs as agonist or antagonists of sphingosine-1-phosphate receptor activity to treat a wide variety of human disorders. S1P analogs of the present invention have a range of activities including agonism, with various degrees of selectivity at individual S1P receptor subtypes, as well as compounds with antagonist activity at the S1P receptors. More particularly, the S1P analogs of the present invention include compounds with the general structure:

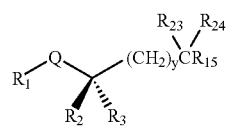

wherein Q is selected from the group consisting of $C_3$-$C_6$ optionally substituted cycloalkyl, $C_3$-$C_6$ optionally substituted heterocyclic, $C_3$-$C_6$ optionally substituted aryl, $C_3$-$C_6$ optionally substituted heteroaryl and

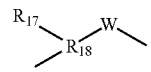

$R_1$ is selected from the group consisting of alkyl, alkenyl, alkynyl, alkyl(optionally substituted aryl), arylalkyl and arylalkyl(optionally substituted)aryl;

$R_{17}$ is H, alkyl, alkylaryl or alkyl(optionally substituted aryl);

$R_{18}$ is N, O, S, CH or together with $R_{17}$ form a carbonyl group or a bond;

W is NH, $CH_2$ or $(CH_2)_n NH(CO)$;

$R_2$ and $R_3$ are independently selected from the group consisting of H, $NH_2$, $C_1$-$C_6$ alkyl, ($C_1$-$C_4$ alkyl)OH, and ($C_1$-$C_4$ alkyl)$NH_2$, with the proviso that $R_2$ and $R_3$ are not the same and either $R_2$ or $R_3$ is $NH_2$.

$R_{23}$ is selected from the group consisting of H, F, $NH_2$, OH, $CO_2H$, $C_1$-$C_6$ alkyl, ($C_1$-$C_4$ alkyl)OH, and ($C_1$-$C_4$ alkyl)$NH_2$;

$R_{24}$ is selected from the group consisting of H, F, $CO_2H$, OH and $PO_3H_2$, or $R_{23}$ together with $R_{24}$ and the carbon to which they are attached form a carbonyl group;

$R_{15}$ is selected from the group consisting of hydroxy, phosphonate, and

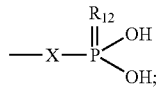

wherein $R_{12}$ is selected from the group consisting of O, NH and S;

X is selected from the group consisting of O, NH and S;

y is an integer ranging from 0-10; n is an integer ranging from 0-4; and pharmaceutically acceptable salts and tautomers of such compounds, with the proviso that R18 and W are not both CH2. Selective agonists and antagonists at S1P receptors will be useful therapeutically in a wide variety of human disorders.

BRIEF DESCRIPTION OF THE DRAWINGS

FIG. 1A=S1P1 receptor, FIG. 1B=S1P3 receptor, FIG. 1C=S1P2 receptor, FIG. 1D=S1P4 receptor, FIG. 1E=S1P5 receptor, and FIG. 1F=S1P3 receptor. Each data point represents the mean of three determinations (CPM=counts per minute).

FIG. 2A=S1P1 receptor, FIG. 2B=S1P3 receptor, FIG. 2C=S1P2 receptor, FIG. 2D=S1P4 receptor, and FIG. 2E=S1P5 receptor. Each data point represents the mean of three determinations (CPM=counts per minute).

FIG. 3A=S1P1 receptor, FIG. 3B=S1P3 receptor, FIG. 3C=S1P2 receptor, FIG. 3D=S1P4 receptor, and FIG. 3E=S1P5 receptor. Each data point represents the mean of three determinations (CPM=counts per minute).

FIG. 4A=S1P1 receptor, FIG. 4B=S1P3 receptor, FIG. 4C=S1P2 receptor, FIG. 4D=S1P4 receptor, and FIG. 4E=S1P5 receptor. Each data point represents the mean of three determinations (CPM=counts per minute).

FIG. 5A is a graphic representation of [γ-35 S]GTP binding to HEK293T cell membranes containing the S1P1 receptor, in response to S1P, VPC23087 and VPC23087+S1P. FIG. 5B is a graphic representation of [γ-35 S]GTP binding to HEK293T cell membranes containing the S1P3 receptor, in response to S1P, VPC23089 and VPC23089+S1P. Each data point represents the mean of three determinations (CPM=counts per minute).

FIG. 6A=S1P1 receptor, FIG. 6B=S1P3 receptor, FIG. 6C=S1P4 receptor, and FIG. 6D=S1P5 receptor. Each data point represents the mean of three determinations, wherein the activity of VPC24289 and VPC24287 is measured relative to S1P activity at the specific receptor subtype.

DETAILED DESCRIPTION

Figure 1A:
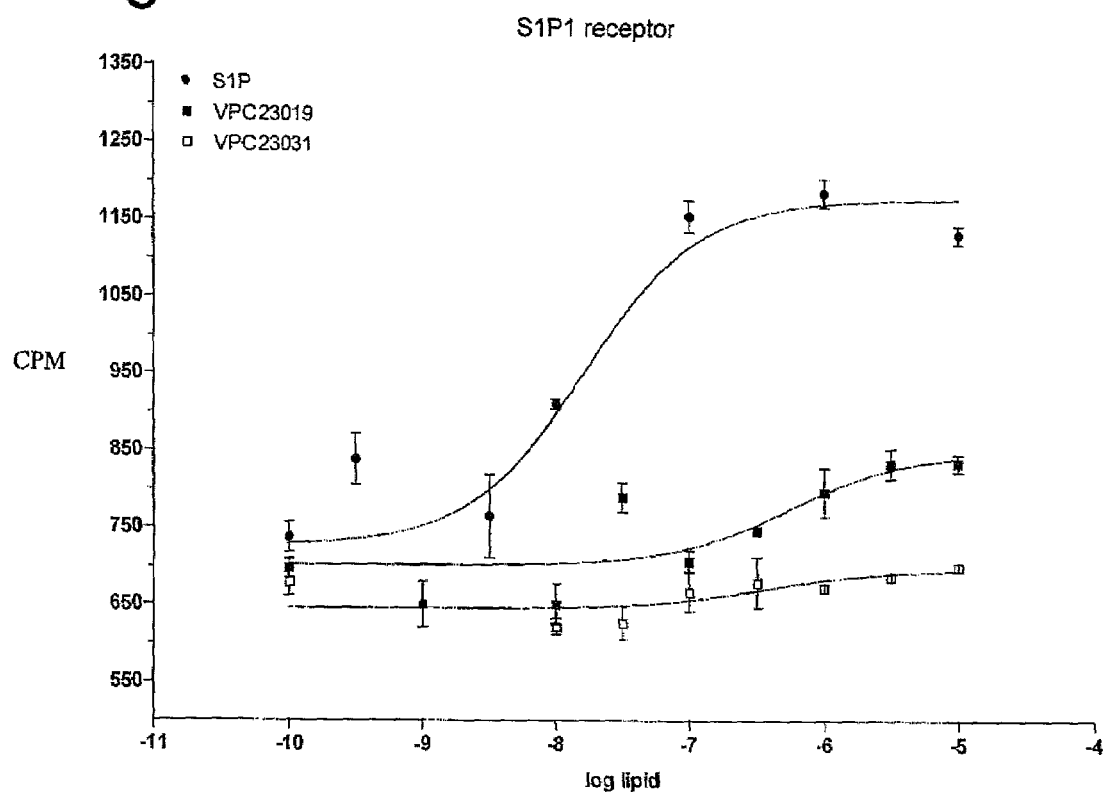
FIG. 1A-1F are graphic representations of [γ-35 S]GTP binding to HEK293T cell membranes (containing different S1P receptors) in response to S1P, VPC23019 and VPC23031.
Figure 1B:
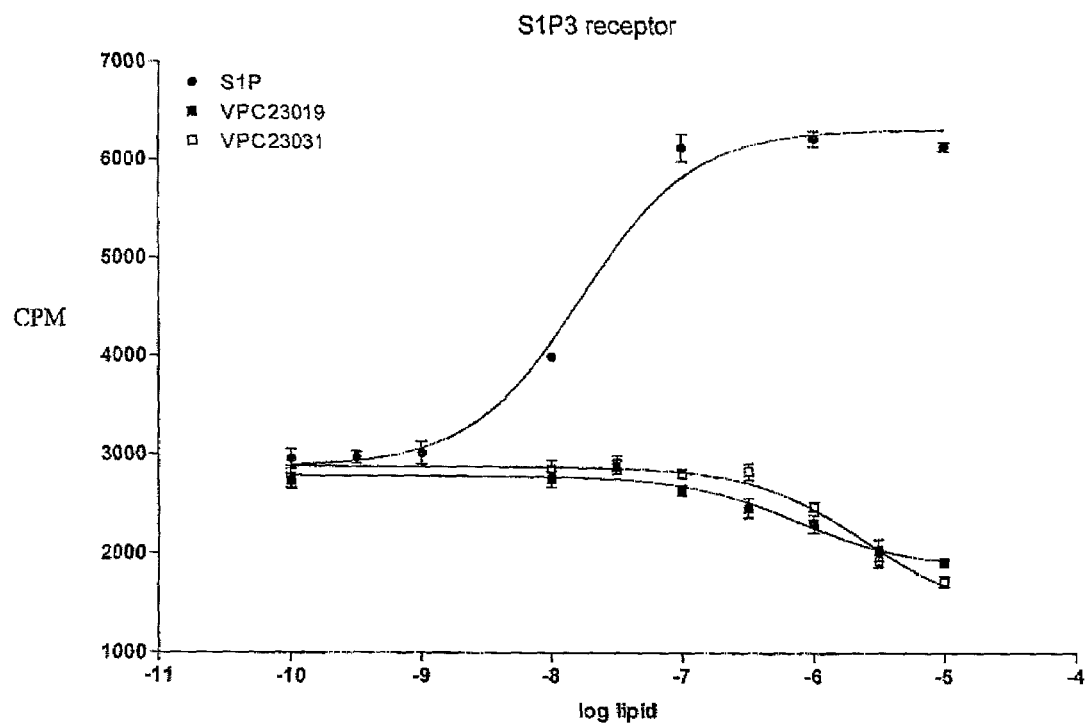
Figure 1C:
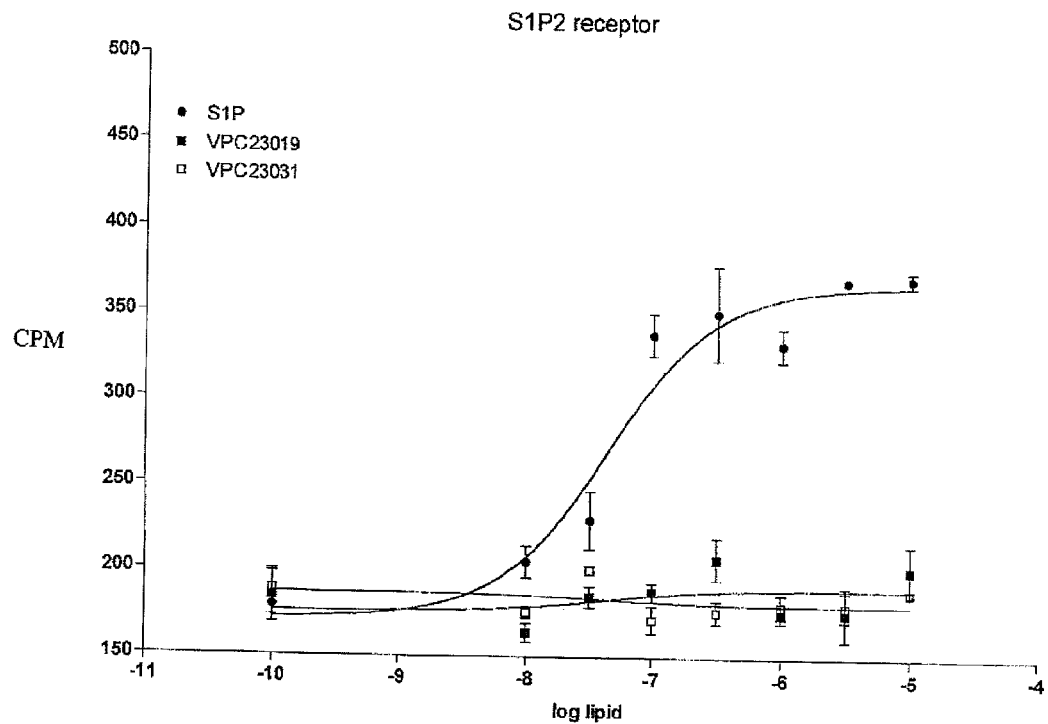
Figure 1D:
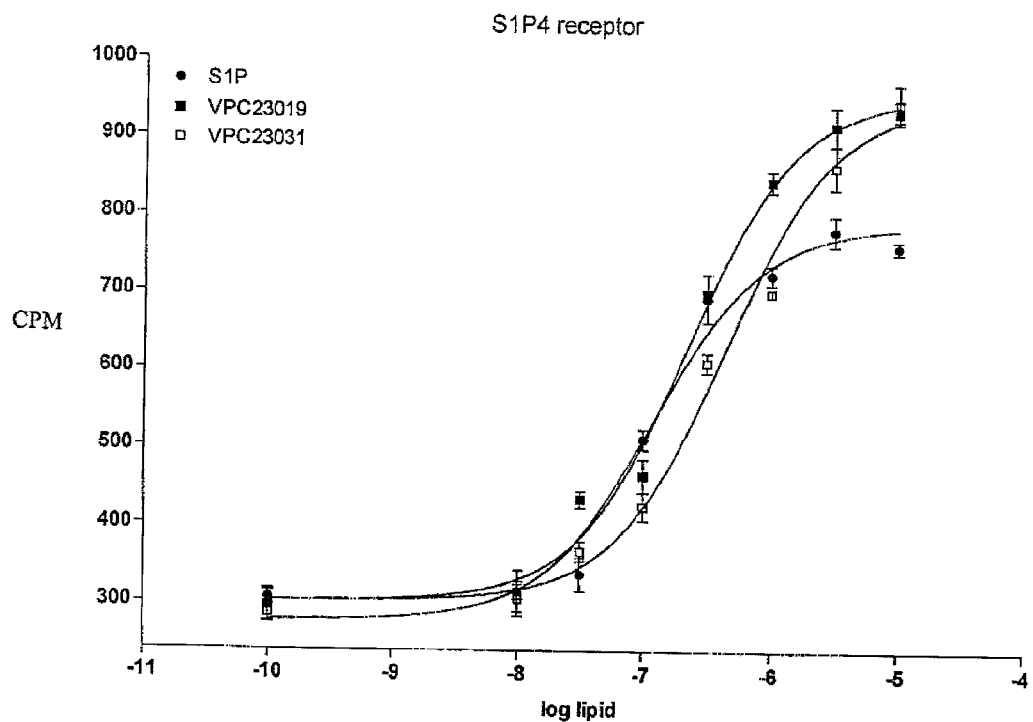
Figure 1E:
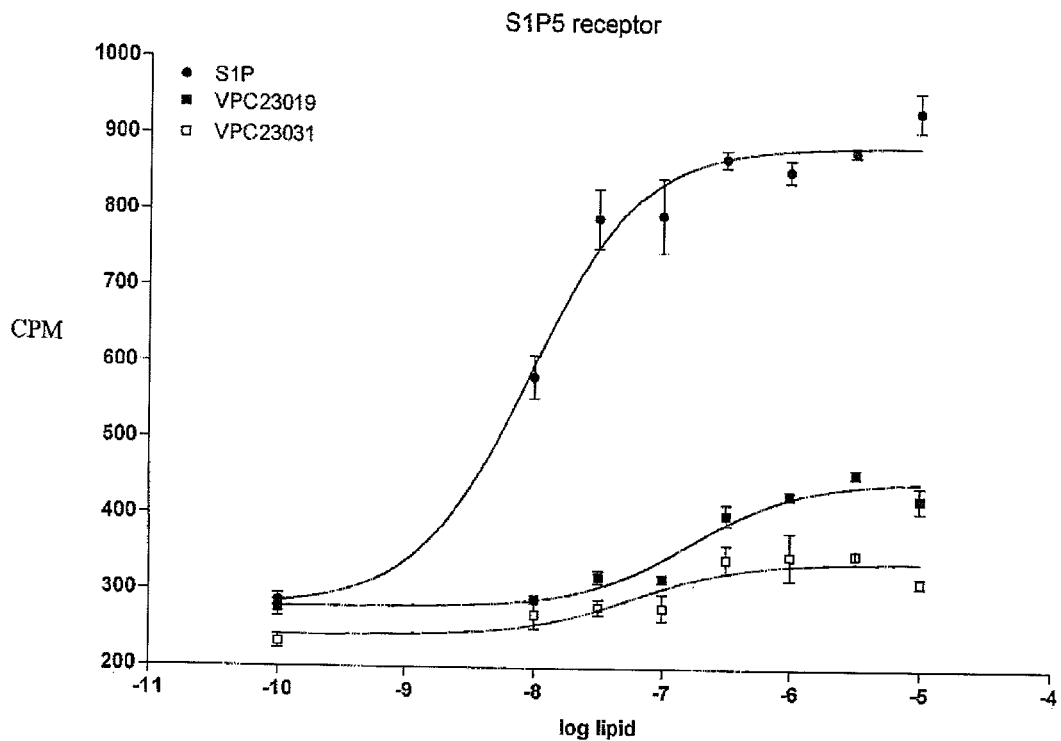
Figure 1F:
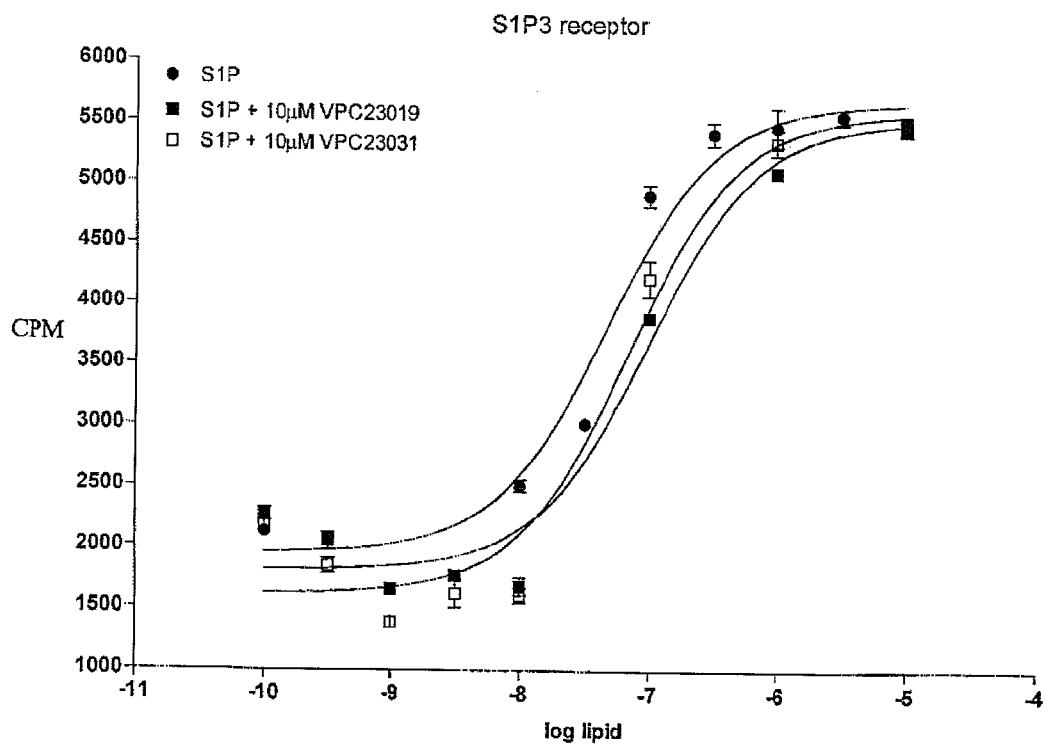

In describing and claiming the invention, the following terminology will be used in accordance with the definitions set forth below.

As used herein, the term "purified" and like terms relate to an enrichment of a molecule or compound relative to other components normally associated with the molecule or compound in a native environment. The term "purified" does not necessarily indicate that complete purity of the particular molecule has been achieved during the process. A "highly purified" compound as used herein refers to a compound that is greater than 90% pure.

As used herein, the term "pharmaceutically acceptable carrier" includes any of the standard pharmaceutical carriers, such as a phosphate buffered saline solution, water, emulsions such as an oil/water or water/oil emulsion, and various types of wetting agents. The term also encompasses any of the agents approved by a regulatory agency of the US Federal government or listed in the US Pharmacopeia for use in animals, including humans.

As used herein, the term "treating" includes prophylaxis of the specific disorder or condition, or alleviation of the symptoms associated with a specific disorder or condition and/or preventing or eliminating said symptoms.

As used herein, an "effective amount" means an amount sufficient to produce a selected effect. For example, an effective amount of an S1P receptor antagonist is an amount that decreases the cell signaling activity of the S1P receptor.

As used herein, the term "halogen" or "halo" includes bromo, chloro, fluoro, and iodo.

The term "haloalkyl" as used herein refers to an alkyl radical bearing at least one halogen substituent, for example, chloromethyl, fluoroethyl or trifluoromethyl and the like.

The term "$C_1$-$C_n$ alkyl" wherein n is an integer, as used herein, represents a branched or linear alkyl group having from one to the specified number of carbon atoms. Typically $C_1$-$C_6$ alkyl groups include, but are not limited to, methyl, ethyl, n-propyl, iso-propyl, butyl, iso-butyl, sec-butyl, tert-butyl, pentyl, hexyl and the like.

The term "$C_2$-$C_n$ alkenyl" wherein n is an integer, as used herein, represents an olefinically unsaturated branched or linear group having from 2 to the specified number of carbon atoms and at least one double bond. Examples of such groups include, but are not limited to, 1-propenyl, 2-propenyl, 1,3-butadienyl, 1-butenyl, hexenyl, pentenyl, and the like.

The term "$C_2$-$C_n$ alkynyl" wherein n is an integer refers to an unsaturated branched or linear group having from 2 to the specified number of carbon atoms and at least one triple bond. Examples of such groups include, but are not limited to, 1-propynyl, 2-propynyl, 1-butynyl, 2-butynyl, 1-pentynyl, and the like.

The term "$C_3$-$C_n$ cycloalkyl" wherein n=8, represents cyclopropyl, cyclobutyl, cyclopentyl, cyclohexyl, cycloheptyl, and cyclooctyl.

As used herein, the term "optionally substituted" refers to from zero to four substituents, wherein the substituents are each independently selected. Each of the independently selected substituents may be the same or different than other substituents.

As used herein the term "aryl" refers to a mono- or bicyclic carbocyclic ring system having one or two aromatic rings including, but not limited to, phenyl, benzyl, naphthyl, tetrahydronaphthyl, indanyl, indenyl, and the like. "Optionally substituted aryl" includes aryl compounds having from zero to four substituents, and "substituted aryl" includes aryl compounds having one to three substituents, wherein the substituents, including alkyl, halo or amino substituents. The term ($C_5$-$C_8$ alkyl)aryl refers to any aryl group which is attached to the parent moiety via the alkyl group.

The term "heterocyclic group" refers to a mono- or bicyclic carbocyclic ring system containing from one to three heteroatoms wherein the heteroatoms are selected from the group consisting of oxygen, sulfur, and nitrogen.

As used herein the term "heteroaryl" refers to a mono- or bicyclic carbocyclic ring system having one or two aromatic rings containing from one to three heteroatoms and includes, but is not limited to, furyl, thienyl, pyridyl and the like.

The term "bicyclic" represents either an unsaturated or saturated stable 7- to 12-membered bridged or fused bicyclic carbon ring. The bicyclic ring may be attached at any carbon atom which affords a stable structure. The term includes, but is not limited to, naphthyl, dicyclohexyl, dicyclohexenyl, and the like.

The term "lower alkyl" as used herein refers to branched or straight chain alkyl groups comprising one to eight carbon atoms, including methyl, ethyl, propyl, isopropyl, n-butyl, t-butyl, neopentyl and the like.

The terms 16:0, 18:0, 18:1, 20:4 or 22:6 hydrocarbon refers to a branched or straight alkyl or alkenyl group, wherein the first integer represents the total number of carbons in the group and the second integer represent the number of double bonds in the group.

As used herein, an "S1P modulating agent" refers a compound or composition that is capable of inducing a detectable change in S1P receptor activity in vivo or in vitro (e.g., at least 10% increase or decrease in S1P activity as measured by a given assay such as the bioassay described in Example 2).

As used herein, the term "$EC_{50}$ of an agent" refers to that concentration of an agent at which a given activity, including binding of sphingosine or other ligand of an S1P receptor and/or a functional activity of a S1P receptor (e.g., a signaling activity), is 50% maximal for that S1P receptor. Stated differently, the $EC_{50}$ is the concentration of agent that gives 50% activation, when 100% activation is set at the amount of activity of the S1P receptor which does not increase with the addition of more ligand/agonist and 0% is set at the amount of activity in the assay in the absence of added ligand/agonist.

As used herein, the term "phosphate analog" and "phosphonate analog" comprise analogs of phosphate and phosphonate wherein the phosphorous atom is in the +5 oxidation state and one or more of the oxygen atoms is replaced with a non-oxygen moiety, including for example, the phosphate analogs phosphorothioate, phosphorodithioate, phosphoroselenoate, phosphorodiselenoate, phosphoroanilothioate, phosphoranilidate, phosphoramidate, boronophosphates, and the like, including associated counterions, e.g., H, $NH_4$, Na, and the like if such counterions are present.

The S1P analogs of the present invention contain one or more asymmetric centers in the molecule. In accordance with the present invention a structure that does not designate the stereochemistry is to be understood as embracing all the various optical isomers, as well as racemic mixtures thereof.

The compounds of the present invention may exist in tautomeric forms and the invention includes both mixtures and separate individual tautomers. For example the following structure:

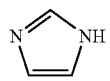

is understood to represent a mixture of the structures:

The term "pharmaceutically-acceptable salt" refers to salts which retain the biological effectiveness and properties of the S1P analogs of the present invention and which are not biologically or otherwise undesirable. In many cases, the S1P analogs of the present invention are capable of forming acid and/or base salts by virtue of the presence of amino and/or carboxyl groups or groups similar thereto.

Pharmaceutically-acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri(cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group. Examples of suitable amines include, by way of example only, isopropylamine, trimethyl amine, diethyl amine, tri(iso-propyl) amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like. It should also be understood that other carboxylic acid derivatives would be useful in the practice of this invention, for example, carboxylic acid amides, including carboxamides, lower alkyl carboxamides, dialkyl carboxamides, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

EMBODIMENTS

One aspect of the present invention is directed to novel S1P analogs that have activity as modulators of S1P receptor activity. Modulators of S1P activity include agents that have either agonist or antagonist activity at the S1P receptor as well as analogs of those compounds that have been modified to resist enzymatic modification (i.e. block modification of the compounds by phosphohydrolases, sphingosine lyases or sphingosine kinases), or provide a suitable substrate for sphingosine kinases to convert an administered form into a more active form.

The structure of S1P can be described as a combination of three regions: the phosphate head group, the linker region, and the fatty acid tail. Through structure activity relationships (SAR) of the closely related lysophospholipid, lysophosphatidic acid (LPA), it has been determined that the presence of a phosphate head group is an important feature to allow binding of S1P to its S1P receptors. However, there are exceptions to the requirement for a phosphate head group. In particular a phosphonate, hydroxyl, phosphate or phosphonate group can be substituted for the phosphate head group while retaining activity at the S1P receptor.

Based on the SAR of LPA, the linker region of S1P is anticipated to be the area of the molecule that can best accommodate change. Again using the SAR of LPA as a lead, it is presumed that presence of a hydrogen bond donor 5 bonds away from the phosphate is important to binding. From a retrosynthetic standpoint, the linker region may be seen as a functionalized derivative of L-Serine.

Due to the long fatty acid chain and charged phosphate head group, S1P has an amphipathic nature that makes it extremely insoluble in organic solvents. Manipulation of the saturation of the fatty acid chain may compromise aggregate formation of the molecule, thereby increasing solubility. One important aspect of the long chain, however, is the length. GTPγS studies that have been completed thus far have demonstrated that an 18 carbon backbone, as is the case in S1P, displays optimal activity compared to 16 and 20 carbon backbones, however the long fatty acid chain can vary from 8 to 25 carbons and still exhibit activity.

It is also anticipated that the S stereochemistry of the C-2 amine may have an effect on binding as one would expect from a receptor. Hydrogen bonds from the phosphate head group and the C-2 amine to adjacent argenine and glutamic acid residues on the model receptor have been demonstrated to be important to S1P-receptor binding. In accordance with one embodiment an S1P receptor modulating compound is provided wherein the compound has the general structure:

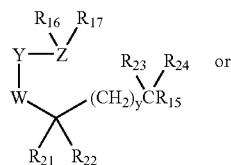

or

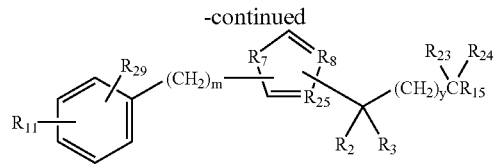

wherein
W is $CR_{27}R_{28}$ or $(CH_2)_n NH(CO)$;
wherein $R_{27}$ and $R_{28}$ are independently selected from the group consisting of H, halo and hydroxy;
Y is selected from the group consisting of a bond, $CR_9R_{10}$, carbonyl, NH, O or S;
wherein $R_9$ and $R_{10}$ are independently selected from the group consisting of H, halo, hydroxy and amino;
Z is $CH_2$, aryl, flourine substituted aryl or heteroaryl;
$R_{11}$ and $R_{16}$ are independently selected from the group consisting of $C_1$-$C_{18}$ alkyl, $C_2$-$C_{18}$ alkenyl, $C_2$-$C_{18}$ alkynyl, $C_5$-$C_{18}$ alkoxy, $(CH_2)_p O(CH_2)_q$, $C_5$-$C_{10}$ (aryl)$R_{20}$, $C_5$-$C_{10}$ (heteroaryl)$R_{20}$, $C_5$-$C_{10}$ (cycloalkyl)$R_{20}$, $C_5$-$C_{10}$ alkoxy(aryl)$R_{20}$, $C_5$-$C_{10}$ alkoxy(heteroaryl)$R_{20}$ and $C_5$-$C_{10}$ alkoxy(cycloalkyl)$R_{20}$;
wherein $R_{20}$ is H or $C_1$-$C_{10}$ alkyl;
$R_{29}$ is H or halo;
$R_{17}$ is selected from the group consisting of H, halo, $NH_2$, $C_1$-$C_6$ alkyl, $C_1$-$C_6$ alkoxy, $C_1$-$C_6$ alkylamino, $C_1$-$C_6$ alkylcyano and $C_1$-$C_6$ alkylthio;
$R_2$, and $R_{21}$ are both $NH_2$;
$R_3$ is selected from the group consisting of H, $C_1$-$C_6$ alkyl, ($C_1$-$C_4$ alkyl)OH, ($C_1$-$C_4$ alkyl)$NH_2$, ($C_1$-$C_4$ alkyl)aryl ($C_0$-$C_4$ alkyl) and ($C_1$-$C_4$ alkyl)aryloxyaryl($C_0$-$C_4$ alkyl);
$R_{22}$ is selected from the group consisting of $C_1$-$C_6$ alkyl, ($C_1$-$C_4$ alkyl)OH, ($C_1$-$C_4$ alkyl)$NH_2$, ($C_1$-$C_4$ alkyl)aryl ($C_0$-$C_4$ alkyl) and ($C_1$-$C_4$ alkyl)aryloxyaryl($C_0$-$C_4$ alkyl);
$R_{23}$ is selected from the group consisting of H, F, $NH_2$, OH, $CO_2H$, $C_1$-$C_6$ alkyl, ($C_1$-$C_4$ alkyl)OH, and ($C_1$-$C_4$ alkyl)$NH_2$;
$R_{24}$ is selected from the group consisting of H, F, $CO_2H$, OH and $PO_3H_2$, or $R_{23}$ together with $R_{24}$ and the carbon to which they are attached form a carbonyl group;
$R_{25}$, $R_7$ and $R_8$ are independently selected from the group consisting of O, S, $CHR_{26}$, $CR_{26}$, $NR_{26}$, and N;
wherein $R_{26}$ is H or $C_1$-$C_4$ alkyl;
$R_{15}$ is selected from the group consisting of hydroxy, phosphonate, and

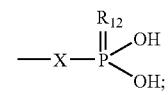

wherein $R_{12}$ is selected from the group consisting of O, NH and S;
X is selected from the group consisting of O, NH and S;
y and m are integers independently ranging from 0 to 4;
p and q are integers independently ranging from 1 to 10;
n is an integer ranging from 0 to 10;
or a pharmaceutically acceptable salt or tautomer thereof, with the proviso that W and Y are not both methylene.

In one embodiment, the present invention is directed to an S1P receptor modulating compound is represented by the formula:

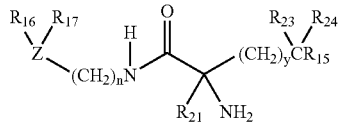

II wherein
Z is $CH_2$, aryl or heteroaryl;

$R_{16}$ is selected from the group consisting of $C_1$-$C_{18}$ alkyl, $C_2$-$C_{18}$ alkenyl, $C_2$-$C_{18}$ alkynyl, $C_5$-$C_{18}$ alkoxy, $(CH_2)_p O(CH_2)_q$, $C_5$-$C_{10}$ (aryl)$R_{20}$, $C_5$-$C_{10}$ (heteroaryl)$R_{20}$, $C_5$-$C_{10}$ (cycloalkyl)$R_{20}$, $C_5$-$C_{10}$ alkoxy(aryl)$R_{20}$, $C_5$-$C_{10}$ alkoxy(heteroaryl)$R_{20}$ and $C_5$-$C_{10}$ alkoxy(cycloalkyl)$R_{20}$, wherein $R_{20}$ is H or $C_1$-$C_{10}$ alkyl;

$R_{17}$ is selected from the group consisting of H, halo, $NH_2$, $C_1$-$C_6$ alkyl, $C_1$-$C_6$ alkoxy, $C_1$-$C_6$ alkylamino, $C_1$-$C_6$ alkylcyano and $C_1$-$C_6$ alkylthio;

$R_{21}$ is selected from the group consisting of $NH_2$, OH, $C_1$-$C_6$ alkyl, ($C_1$-$C_4$ alkyl)OH, ($C_1$-$C_4$ alkyl)$NH_2$, ($C_1$-$C_4$ alkyl)aryl($C_0$-$C_4$ alkyl) and ($C_1$-$C_4$ alkyl)aryloxyaryl ($C_0$-$C_4$ alkyl), with the proviso that $R_2$ or $R_3$ is $NH_2$;

$R_{15}$ is selected from the group consisting of hydroxy, phosphonate, and

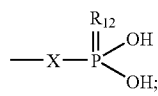

wherein X and $R_{12}$ are independently selected from the group consisting of O and S;

$R_{23}$ is selected from the group consisting of H, F, $NH_2$, OH, $CO_2H$, $C_1$-$C_6$ alkyl, ($C_1$-$C_4$ alkyl)OH, and ($C_1$-$C_4$ alkyl)$NH_2$;

$R_{24}$ is selected from the group consisting of H, F, $CO_2H$, OH and $PO_3H_2$, or $R_{23}$ together with $R_{24}$ and the carbon to which they are attached form a carbonyl group; p and q are integers independently ranging from 1 to 10;

y is an integer ranging from 0 to 4; and n is an integer ranging from 0 to 10;

or a pharmaceutically acceptable salt or tautomer thereof.
In one embodiment the compound of Formula II is provided wherein Z is $CH_2$, y is 0, n is 1-10, and $R_{17}$ is H. In another embodiment, the compound of Formula II is provided wherein Z is $C_5$-$C_6$ aryl or $C_5$-$C_6$ heteroaryl, y is 0, n is 0, $R_{17}$ and $R_{23}$ are each H and $R_{16}$ is selected from the group consisting of $C_5$-$C_{12}$ alkyl, $C_2$-$C_{12}$ alkenyl or $C_5$-$C_{12}$ alkoxy. In another embodiment, the compound of Formula II is provided wherein Z is $C_5$-$C_6$ aryl or $C_5$-$C_6$ heteroaryl, y is 0, n is 0, $R_{17}$, $R_{23}$ and $R_{24}$ are each H, $R_{16}$ is selected from the group consisting of $C_5$-$C_{12}$ alkyl, $C_2$-$C_{12}$ alkenyl or $C_5$-$C_{12}$ alkoxy and $R_{15}$ is hydroxy.

In another embodiment of the present invention, an S1P receptor modulating compound is provided wherein the compound is represented by the formula:

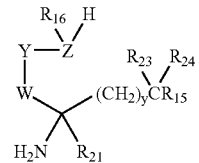

III wherein Z is aryl or heteroaryl;

$R_{16}$ is selected from the group consisting of $C_5$-$C_{18}$ alkyl, $C_5$-$C_{18}$ alkenyl, $C_5$-$C_{18}$ alkynyl and $C_5$-$C_{18}$ alkoxy;

Y is selected from the group consisting of CHOH, $CF_2$, CFH, carbonyl, NH, O and S;

W is $CR_{27}R_{28}$, wherein $R_{27}$ and $R_{28}$ are independently selected from the group consisting of H, halo and hydroxy;

$R_{21}$ is selected from the group consisting of $NH_2$, OH, $C_1$-$C_6$ alkyl, ($C_1$-$C_4$ alkyl)OH, ($C_1$-$C_4$ alkyl)$NH_2$, ($C_1$-$C_4$ alkyl)aryl($C_0$-$C_4$ alkyl) and ($C_1$-$C_4$ alkyl)aryloxyaryl ($C_0$-$C_4$ alkyl);

$R_{23}$ is selected from the group consisting of H, F, $NH_2$, OH, $CO_2H$, $C_1$-$C_6$ alkyl, ($C_1$-$C_4$ alkyl)OH, and ($C_1$-$C_4$ alkyl)$NH_2$;

$R_{24}$ is selected from the group consisting of H, F, $CO_2H$, OH and $PO_3H_2$, or $R_{23}$ together with $R_{24}$ and the carbon to which they are attached form a carbonyl group;

$R_{15}$ is selected from the group consisting of hydroxy, phosphonate, and

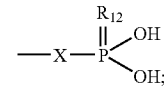

wherein X and $R_{12}$ are independently selected from the group consisting of O and S; and y is an integer ranging from 0 to 4;

or a pharmaceutically acceptable salt or tautomer thereof.
In one embodiment the compound of Formula III is provided wherein Z is $C_5$-$C_6$ aryl or $C_5$-$C_6$ heteroaryl, $R_{23}$ and $R_{24}$ are both H, $R_{21}$ is selected from the group consisting of OH, $C_1$-$C_4$ alkyl, and ($C_1$-$C_3$ alkyl)OH; and y is 0.

In another embodiment, the compound is represented by the formula:

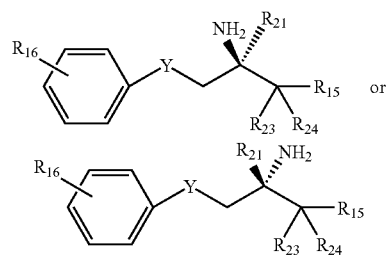

wherein $R_{16}$ is selected from the group consisting of $C_5$-$C_{12}$ alkyl, $C_5$-$C_{12}$ alkenyl and $C_5$-$C_{12}$ alkynyl;

Y is selected from the group consisting of carbonyl, NH and O;

$R_{15}$ is selected from the group consisting of hydroxy, phosphonate, and

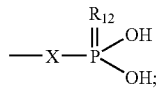

wherein X and $R_{12}$ are independently selected from the group consisting of O and S;

$R_{21}$ is selected from the group consisting of $C_1$-$C_6$ alkyl, ($C_1$-$C_4$ alkyl)OH and ($C_1$-$C_4$ alkyl)NH$_2$;

$R_{23}$ and $R_{24}$ are independently selected from the group consisting of H, OH, F, CO$_2$H or PO$_3$H$_2$ or $R_{23}$ together with $R_{24}$ and the carbon to which they are attached form a carbonyl group, as well as pharmaceutically acceptable salts and tautomers thereof.

In another embodiment, the compound of Formula III is provided wherein Z is $C_5$-$C_6$ aryl;

$R_{16}$ is selected from the group consisting of $C_5$-$C_{18}$ alkyl and $C_5$-$C_{18}$ alkenyl;

Y is selected from the group consisting of CF$_2$, CFH, carbonyl, NH, O and S;

W is CH$_2$;

$R_{21}$ is selected from the group consisting of $C_1$-$C_6$ alkyl, ($C_1$-$C_4$ alkyl)OH and ($C_1$-$C_4$ alkyl)NH$_2$;

$R_{23}$ and $R_{24}$ are both H; y is 0; and $R_{15}$ is selected from the group consisting of hydroxy, phosphonate, and

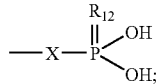

wherein $R_{12}$ is O and S (and in one embodiment $R_{15}$ is OH), or a pharmaceutically acceptable salt or tautomer thereof.

In another embodiment of the present invention a S1P receptor modulating compound is provided wherein the compound is represented by the formula:

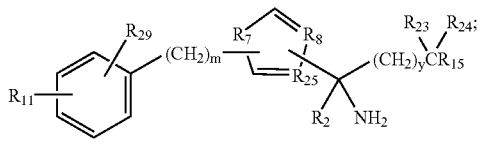

IV

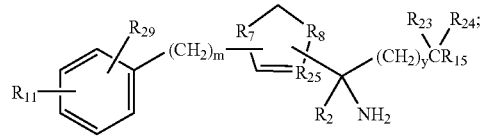

V

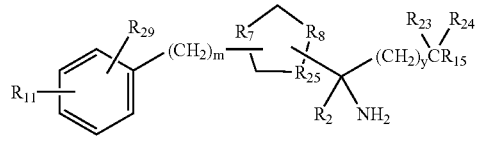

VI wherein $R_{11}$ is selected from the group consisting of $C_5$-$C_{12}$ alkyl, $C_5$-$C_{12}$ alkenyl and $C_5$-$C_{12}$ alkynyl;

$R_{29}$, is H or halo;

$R_{25}$, $R_7$ and $R_8$ are independently selected from the group consisting of O, S, CHR$_{26}$, CR$_{26}$, NR$_{26}$, and N; wherein $R_{26}$ is H, F or $C_1$-$C_4$ alkyl;

$R_2$, is selected from the group consisting of H, NH$_2$, OH, $C_1$-$C_6$ alkyl, ($C_1$-$C_4$ alkyl)OH, ($C_1$-$C_4$ alkyl)NH$_2$, ($C_1$-$C_4$ alkyl)aryl($C_0$-$C_4$ alkyl) and ($C_1$-$C_4$ alkyl)aryloxyaryl ($C_0$-$C_4$ alkyl);

$R_{15}$ is selected from the group consisting of hydroxy, phosphonate, and

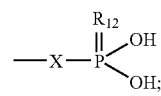

wherein X and $R_{12}$ are independently selected from the group consisting of O and S;

$R_{23}$ and $R_{24}$ are independently selected from the group consisting of H, OH, F, CO$_2$H, $C_1$-$C_3$ alkyl or PO$_3$H$_2$ or $R_{23}$ together with $R_{24}$ and the carbon to which they are attached form a carbonyl group;

m is 1 or 0; and y is an integer ranging from 0 to 4;

or a pharmaceutically acceptable salt or tautomer thereof.

In one embodiment, $R_{29}$ is H or F; m is 0; y is 1 or 0; $R_2$ is selected from the group consisting of H, $C_1$-$C_6$ alkyl and ($C_1$-$C_4$ alkyl)OH; $R_{24}$ is H and $R_{23}$ is $C_1$-$C_3$ alkyl. In accordance with one embodiment of the present invention a compound of Formula IV, V or VI is provided wherein $R_{23}$ and $R_{29}$ are both H; m is 0; $R_{25}$ is CH$_2$ or CH; $R_7$ and $R_8$ are independently selected from the group consisting of O, CH$_2$ or CH, NH, and N; $R_2$, is selected from the group consisting of H, F, $C_1$-$C_4$ alkyl and ($C_1$-$C_4$ alkyl)OH; $R_{24}$ is selected from the group consisting of H, F, $C_1$-$C_3$ alkyl; and y is 1 or 0.

In one embodiment of the present invention, an S1P receptor modulating compound is provided wherein the compound is represented by the formula:

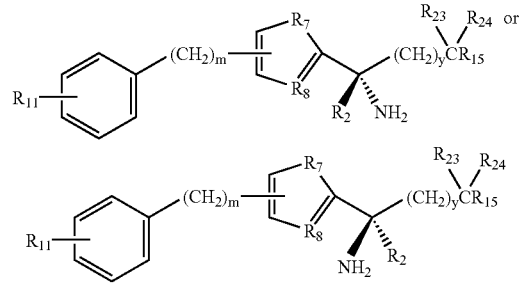

wherein $R_{11}$ is selected from the group consisting of $C_5$-$C_{18}$ alkyl, $C_5$-$C_{18}$ alkenyl and $C_5$-$C_{18}$ alkynyl;

$R_7$ and $R_8$ are independently selected from the group consisting of O, S, NH and N;

$R_2$, is selected from the group consisting of H, $C_1$-$C_6$ alkyl, ($C_1$-$C_4$ alkyl)OH, and ($C_1$-$C_4$ alkyl)NH$_2$;

$R_{15}$ is selected from the group consisting of hydroxy, phosphonate, and

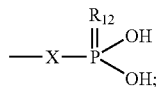

wherein X and $R_{12}$ are independently selected from the group consisting of O and S;

$R_{23}$ is selected from the group consisting of H, F and OH;

$R_{24}$ is selected from the group consisting of H, F, OH and $PO_3H_2$, or $R_{23}$ together with $R_{24}$ and the carbon to which they are attached form a carbonyl group;

m is 0; and y is an integer ranging from 0 to 4;

or a pharmaceutically acceptable salt or tautomer thereof.

In one embodiment of the present invention a S1P receptor modulating compound is provided wherein the compound is represented by the formula:

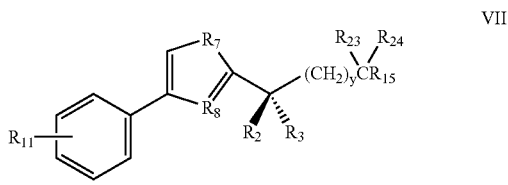

VII wherein $R_{11}$ is selected from the group consisting of $C_5$-$C_{12}$ alkyl, $C_5$-$C_{12}$ alkenyl and $C_5$-$C_{12}$ alkynyl;

$R_7$ and $R_8$ are independently selected from the group consisting of O, S, $CH_2$, CH, NH and N;

$R_2$ and $R_3$ are independently selected from the group consisting of H, $NH_2$, OH, $C_1$-$C_6$ alkyl, ($C_1$-$C_4$ alkyl)OH, ($C_1$-$C_4$ alkyl)$NH_2$, ($C_1$-$C_4$ alkyl)aryl($C_0$-$C_4$ alkyl) and ($C_1$-$C_4$ alkyl)aryloxyaryl($C_0$-$C_4$ alkyl), with the proviso that $R_2$ and $R_3$ are not the same and either $R_2$ or $R_3$ is $NH_2$;

y is 1 or 0

$R_{15}$ is selected from the group consisting of hydroxy, phosphonate, and

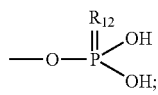

wherein $R_{12}$ is selected from the group consisting of O and S;

$R_{23}$ is selected from the group consisting of H, F, $CO_2H$, $C_1$-$C_4$ alkyl and OH;

$R_{24}$ is selected from the group consisting of H, F, $C_1$-$C_4$ alkyl and $PO_3H_2$, or $R_{23}$ together with $R_{24}$ and the carbon to which they are attached form a carbonyl group; as well as pharmaceutically acceptable salts or tautomers thereof.

In accordance with one embodiment of the present invention, a compound of Formula VII is provided wherein $R_{23}$ is H; $R_{24}$ is selected from the group consisting of H, F, $C_1$-$C_4$ alkyl; and $R_7$ and $R_8$ are independently selected from the group consisting of O, NH and N. In another embodiment, a compound of Formula VII is provided wherein $R_{23}$ is H; $R_2$ is $NH_2$; and $R_3$ is selected from the group consisting of H, $C_1$-$C_4$ alkyl, ($C_1$-$C_4$ alkyl)OH and ($C_1$-$C_4$ alkyl)$NH_2$. Alternatively, in one embodiment a compound of Formula VII is provided wherein $R_{23}$ is H; $R_3$ is $NH_2$; and $R_2$ is selected from the group consisting of H, $C_1$-$C_4$ alkyl, ($C_1$-$C_4$ alkyl)OH and ($C_1$-$C_4$ alkyl)$NH_2$. In another embodiment, a compound of Formula VII is provided wherein $R_{23}$ is H; $R_2$ is $NH_2$; and $R_3$ is selected from the group consisting of H, $C_1$-$C_4$ alkyl, ($C_1$-$C_4$ alkyl)OH and ($C_1$-$C_4$ alkyl)$NH_2$; $R_{24}$ is selected from the group consisting of H, F, $C_1$-$C_4$ alkyl; and $R_7$ and $R_8$ are independently selected from the group consisting of O, NH and N. In another embodiment, a compound of Formula VII is provided wherein $R_{11}$ is selected from the group consisting of $C_5$-$C_{12}$ alkyl or $C_5$-$C_{12}$ alkenyl; $R_7$ and $R_9$ are independently selected from the group consisting of O, NH and N; $R_2$ and $R_3$ are independently selected from the group consisting of H, $NH_2$, $C_1$-$C_6$ alkyl and ($C_1$-$C_4$ alkyl)OH, with the proviso that $R_2$ and $R_3$ are not the same and either $R_2$ or $R_3$ is $NH_2$; y is 0; $R_{15}$ is hydroxy; $R_{23}$ is H; and $R_{24}$ is H, F or $C_1$-$C_4$ alkyl; as well as pharmaceutically acceptable salts or tautomers thereof.

In one embodiment of the present invention, a S1P receptor modulating compound is provided wherein the compound is represented by the formula:

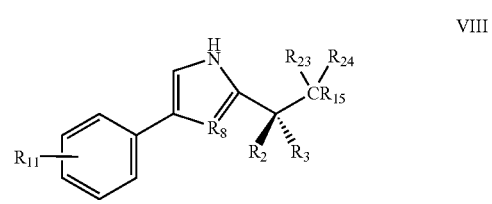

VIII wherein $R_{11}$ is selected from the group consisting of $C_5$-$C_{12}$ alkyl, $C_5$-$C_{12}$ alkenyl and $C_5$-$C_{12}$ alkynyl;

$R_8$ is O or N;

$R_2$ and $R_3$ are independently selected from the group consisting of $NH_2$, $C_1$-$C_6$ alkyl and ($C_1$-$C_4$ alkyl)OH, with the proviso that $R_2$ and $R_3$ are not the same and either $R_2$ or $R_3$ is $NH_2$;

$R_{15}$ is selected from the group consisting of hydroxy, phosphonate, and

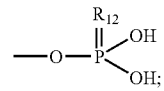

wherein $R_{12}$ is selected from the group consisting of O and S;

$R_{23}$ is H or F; and $R_{24}$ is H, F or $C_1$-$C_4$ alkyl; as well as pharmaceutically acceptable salts or tautomers thereof. In one embodiment the compound of Formula VIII is provided wherein $R_{11}$ is $C_5$-$C_{12}$ alkyl or $C_5$-$C_{12}$ alkenyl; $R_8$ is N; $R_2$ and $R_3$ are independently selected from the group consisting of $NH_2$, $CH_3$ and ($C_1$-$C_3$ alkyl)OH, with the proviso that $R_2$ and $R_3$ are not the same and either $R_2$ or $R_3$ is $NH_2$; and $R_{15}$ is hydroxy; $R_{23}$ is H; and $R_{24}$ is H or $C_1$-$C_4$ alkyl as well as pharmaceutically acceptable salts or tautomers thereof. In another embodiment the compound of Formula VIII is provided wherein $R_{11}$ is $C_5$-$C_{12}$ alkyl or $C_5$-$C_{12}$ alkenyl; $R_8$ is N; $R_2$ and $R_3$ are independently selected from the group consisting of $NH_2$, $CH_3$ and ($C_1$-$C_3$ alkyl)OH, with the proviso that $R_2$ and $R_3$ are not the same and either $R_2$ or $R_3$ is $NH_2$; and $R_{15}$ is hydroxy; $R_{23}$ is H; and $R_{24}$ is H or $CH_3$ as well as pharmaceutically acceptable salts or tautomers thereof.

In one embodiment, a S1P receptor modulating compound is provided wherein the compound is represented by the formula:

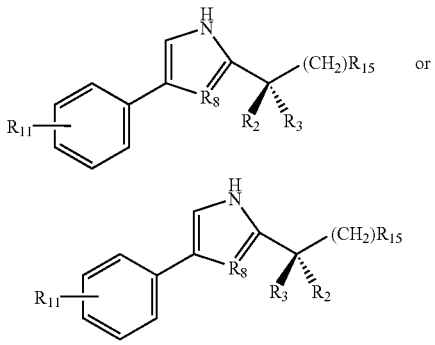

wherein $R_{11}$ is $C_5$-$C_{18}$ alkyl or $C_5$-$C_{18}$ alkenyl;
$R_8$ is N;
$R_2$ is $NH_2$;
$R_3$ is $CH_3$ or $(C_1$-$C_3$ alkyl)OH and $R_{15}$ is hydroxy;
or a pharmaceutically acceptable salt or tautomer thereof.

In accordance with one embodiment, an S1P receptor modulating compound is provided wherein the compound has the general structure:

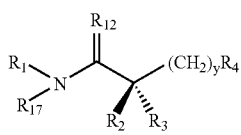
XII wherein $R_1$ is selected from the group consisting of alkyl, alkenyl, alkynyl, alkyl(optionally substituted aryl), alkyl (optionally substituted cycloalkyl), arylalkyl, and arylalkyl(optionally substituted)aryl;
$R_{12}$ is 0, or $R_1$ and $R_{12}$ taken together form an optionally substituted heteroaryl;
$R_{17}$ is H, $C_1$-$C_4$ alkyl or $(CH_2)$aryl;
$R_2$ and $R_3$ are independently selected from the group consisting of H, $NH_2$, OH, $C_1$-$C_6$ alkyl, —$(C_1$-$C_4$ alkyl)OH, and —$(C_1$-$C_4$ alkyl)$NH_2$; y is an integer from 1-10, and $R_4$ is selected from the group consisting of hydroxyl, phosphate, methylene phosphonate, α-substituted methylene phosphonate, phosphate analogs and phosphonate analogs or a pharmaceutically acceptable salt thereof. In one embodiment one of the $R_2$ and $R_3$ substituents of Formula XII is $NH_2$. Examples of pharmaceutically acceptable salts of the compounds of the Formula XII include salts with inorganic acids, such as hydrochloride, hydrobromide and sulfate, salts with organic acids, such as acetate, fumarate, maleate, benzoate, citrate, malate, methanesulfonate and benzenesulfonate salts, and when a carboxy group is present, salts with metals such as sodium, potassium, calcium and aluminium, salts with amines, such as triethylamine and salts with dibasic amino acids, such as lysine. The compounds and salts of the present invention encompass hydrate and solvate forms.

In one embodiment, an S1P modulating compound is provided having the general structure:

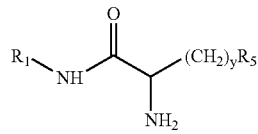

wherein $R_1$ is selected from the group consisting of $C_8$-$C_{22}$ alkyl, $C_8$-$C_{22}$ alkenyl, $C_8$-$C_{22}$ alkynyl and —$(CH_2)_n$-Z-$R_6$;
$R_5$ is selected from the group consisting of hydroxyl, phosphonate, α-substituted methylene phosphonate, phosphate analogs and phosphonate analogs;
y is an integer ranging from 1 to 4;
n is an integer ranging from 0 to 10;
Z is selected from the group consisting of cycloalkyl, aryl and heteroaryl; and
$R_6$ is selected from the group consisting of H, $C_1$-$C_{12}$ alkyl, $C_1$-$C_{20}$ alkoxy, $C_1$-$C_{20}$ alkylthio, and $C_1$-$C_{20}$ alkylamino or a pharmaceutically acceptable salt thereof. When $R_5$ is an alpha substituted phosphonate, the alpha carbon can be mono- or di-substituted, wherein the substitutions are independently selected from the group consisting of H, OH, F, $CO_2H$, $PO_3H_2$, or together with the attached carbon, form a carbonyl. In one embodiment, $R_1$ is $C_8$-$C_{22}$ alkyl, and more preferably $C_{12}$-$C_{16}$ alkyl, y is 1 or 2 and $R_5$ is hydroxy, phosphate or phosphonate. Alternatively, in one embodiment, $R_1$ is —$(CH_2)_n$-Z-$R_6$, wherein n is an integer ranging from 1-4, Z is aryl and $R_6$ is $C_1$-$C_{10}$ alkyl; more preferably, Z is phenyl, $R_5$ is hydroxy, phosphate or phosphonate, and $R_6$ is $C_6$-$C_{10}$ alkyl.

In another embodiment of the present invention, an S1P modulating compound is provided having the general structure:

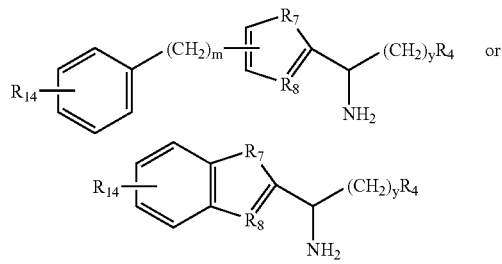

wherein $R_{14}$ is selected from the group consisting of H, hydroxy, $NH_2$, $C_8$-$C_{22}$ alkyl, $C_8$-$C_{22}$ alkenyl, $C_8$-$C_{22}$ alkynyl and —$(CH_2)_n$-Z-$R_6$;
$R_4$ is selected from the group consisting of hydroxyl, phosphate, phosphonate, α-substituted methylene phosphonate, phosphate analogs and phosphonate analogs;
y is an integer ranging from 1 to 4;
m is an integer ranging from 0 to 4;
n is an integer ranging from 0 to 10;
Z is selected from the group consisting of cycloalkyl, aryl and heteroaryl; and
$R_6$ is selected from the group consisting of H, $C_1$-$C_{12}$ alkyl, $C_1$-$C_{20}$ alkoxy, $C_1$-$C_{20}$ alkylthio, and $C_1$-$C_{20}$ alkylamino; and $R_7$ and $R_8$ are independently selected from the group consisting of O, S and N. In one embodiment $R_1$ is selected from the group consisting of $C_8$-$C_{22}$ alkyl, $C_8$-$C_{22}$ alkenyl and $C_8$-$C_{22}$ alkynyl, $R_4$ is hydroxyl, phosphate or phosphonate, y is 1 or 2, m is 0 or 1 and either $R_7$ or $R_8$ is N; more preferably, $R_1$ is $C_4$-$C_{10}$ alkyl, $R_4$ is hydroxyl or phosphate, y is 1, m is 0 and $R_7$ and $R_8$ are both N.

The present invention also encompasses compounds of the general structure:

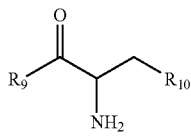

wherein $R_9$ is selected from the group consisting of —$NR_1$, and —$OR_1$;

$R_1$ is selected from the group consisting of $C_8$-$C_{22}$ alkyl and

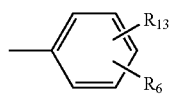

wherein $R_6$ and $R_{13}$ are independently selected from the group consisting of H, $C_1$-$C_{10}$ alkyl and $C_1$-$C_{20}$ alkoxy and $R_{10}$ is hydroxy, phosphonate, methylene phosphonate or phosphate, with the proviso that when $R_9$ is —$NR_1$, $R_{10}$ is not phosphate. In one preferred embodiment, $R_9$ is —$NR_1$, $R_6$ is $C_1$-$C_{10}$ alkyl, $R_{13}$ is H and $R_{10}$ is hydroxy, phosphonate, or methylene phosphonate.

A GTP[γ35 S] binding assay was developed to analyze directly the activation of individual S1P receptors, and thus allow the identification of S1P receptor agonists and antagonists as well as determine the relative efficacies and potencies at each receptor in a common system. The same results were obtained regardless of whether the recombinant receptor used exogenous G proteins (HEK293T cells) or endogenous G proteins (RH7777 cells). In addition, insect Sf9 cells infected with recombinant baculovirus encoding receptors (e.g. LPA and S1P receptors) and G proteins can also serve as the source of membranes for the broken cells used in the GTPgammaS-35 binding assays. The Sf9 cell and HEK293T cell membranes gave similar results. Furthermore, the activities measured in the broken cell assay predicted the responses seen in whole cell assays. Thus the primary assay used in the present invention for determining compound potency and efficacy is a valid measure of activity at the S1P receptors.

The GTP[γ35 S] binding assay has revealed that the compounds of the present invention have the ability to modulate S1P receptor activity (See Examples 2 and 3). More particularly, compounds represented by the following formula display activity as modulators of S1P activity. More particularly, such compounds include those having the structure

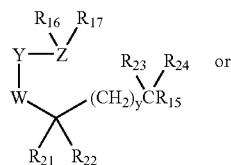

or

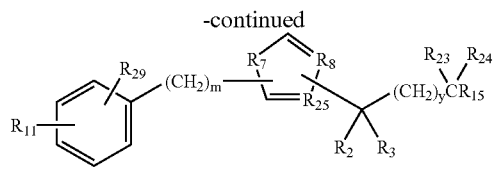

wherein

W is $CR_{27}R_{28}$ or $(CH_2)_nNH(CO)$;

wherein $R_{27}$ and $R_{28}$ are independently selected from the group consisting of H, halo and hydroxy;

Y is selected from the group consisting of a bond, $CR_9R_{10}$, carbonyl, NH, O or S;

wherein $R_9$ and $R_{10}$ are independently selected from the group consisting of H, halo, hydroxy and amino;

Z is $CH_2$, aryl, halo substituted aryl or heteroaryl;

$R_{11}$ and $R_{16}$ are independently selected from the group consisting of $C_1$-$C_{18}$ alkyl, $C_2$-$C_{18}$ alkenyl, $C_2$-$C_{18}$ alkynyl, $C_5$-$C_{18}$ alkoxy, $(CH_2)_pO(CH_2)_q$, $C_5$-$C_{10}$ (aryl)$R_{20}$, $C_5$-$C_{10}$ (heteroaryl)$R_{20}$, $C_5$-$C_{10}$ (cycloalkyl)$R_{20}$, $C_5$-$C_{10}$ alkoxy(aryl)$R_{20}$, $C_5$-$C_{10}$ alkoxy(heteroaryl)$R_{20}$ and $C_5$-$C_{10}$ alkoxy(cycloalkyl)$R_{20}$;

wherein $R_{20}$ is H or $C_1$-$C_{10}$ alkyl;

$R_{29}$ is H or halo;

$R_{17}$ is selected from the group consisting of H, halo, $NH_2$, $C_1$-$C_6$ alkyl, $C_1$-$C_6$ alkoxy, $C_1$-$C_6$ alkylamino, $C_1$-$C_6$ alkylcyano and $C_1$-$C_6$ alkylthio;

$R_2$ and $R_{21}$ are both $NH_2$;

$R_3$ is selected from the group consisting of H, $C_1$-$C_6$ alkyl, $(C_1$-$C_4$ alkyl)OH, and $(C_1$-$C_4$ alkyl)$NH_2$;

$R_{22}$ is selected from the group consisting of $C_1$-$C_6$ alkyl, $(C_1$-$C_4$ alkyl)OH and $(C_1$-$C_4$ alkyl)$NH_2$;

$R_{23}$ is selected from the group consisting of H, F, $CO_2H$, OH, $C_1$-$C_6$ alkyl, $(C_1$-$C_4$ alkyl)OH, and $(C_1$-$C_4$ alkyl)$NH_2$;

$R_{24}$ is selected from the group consisting of H, F and $PO_3H_2$, or $R_{23}$ together with $R_{24}$ and the carbon to which they are attached form a carbonyl group;

$R_{25}$, $R_7$ and $R_8$ are independently selected from the group consisting of O, S, $CHR_{26}$, $CHR_{26}$, $NR_{26}$, and N;

wherein $R_{26}$ is H, F or $C_1$-$C_4$ alkyl;

$R_{15}$ is selected from the group consisting of hydroxy, phosphonate, and

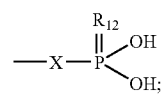

wherein $R_{12}$ is selected from the group consisting of O, NH and S;

X is selected from the group consisting of O, NH and S;

y and m are integers independently ranging from 0 to 4;

p and q are integers independently ranging from 1 to 10;

n is an integer ranging from 0 to 10;

or a pharmaceutically acceptable salt or tautomer thereof, with the proviso that W and Y are not both methylene.

As described in Example 2 compounds having the general structure

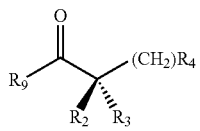

wherein $R_9$ is selected from the group consisting of —$NR_1$, and —$OR_1$, $R_1$ is $C_8$-$C_{22}$ alkyl, $R_2$ and $R_3$ are independently selected from the group consisting of H and $NH_2$, wherein at least one of $R_2$ and $R_3$ is $NH_2$ and $R_4$ is phosphate all display significant agonist activity at the S1P receptors tested (S1P1, S1P2, S1P3, S1P5), although none were as potent as S1P itself (See Table 1 of Example 2). However, one compound, VPC22135 (wherein $R_2$ is H, $R_3$ is $NH_2$, $R_4$ is phosphate and $R_9$ is —$N(CH_2)_{13}CH_3$), approached the potency of S1P at both the human S1P1 and human S1P3 receptors. In accordance with one embodiment of the present invention, compound VPC22135 is used as a selective agonist of human S1P1 and human S1P3 receptors. Curiously, this compound has the amino group in the unnatural (R) configuration. Its enantiomer, VPC22053, was more than 1 log order less potent at both the S1P1 and S1P3 receptors.

An additional series of compounds have shown activity in modulating S1P receptor activity, however these compounds also displayed selectivity for certain S1P receptor subtypes (See Example 3 and FIGS. 1-5). Each of these compounds (VPC 23019, 23031, 23065, 23069, 23087, 23089, 23075, 23079) are inactive at the S1P2 receptor. Compounds VPC23031, 23019, 23089 are inverse agonists (antagonists of the S1P3) receptor, but this inverse agonism becomes agonism when the alkyl chain length is 9 carbons (VPC23079) or 10 (VPC23069). In accordance with one embodiment of the present invention an antagonist of S1P activity is provided. In particular, a compound having the general structure:

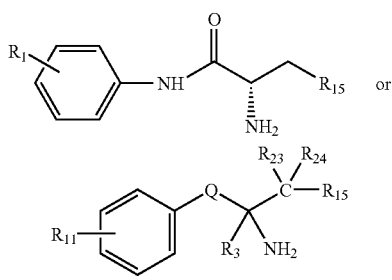

wherein $R_1$ and $R_{11}$ is $C_4$-$C_{12}$ alkyl and located in the meta or ortho position, Q is selected from the group consisting of $C_3$-$C_6$ optionally substituted cycloalkyl, $C_3$-$C_6$ optionally substituted heterocyclic, $C_3$-$C_6$ optionally substituted aryl and $C_3$-$C_6$ optionally substituted heteroaryl;

$R_3$ is selected from the group consisting of H, $C_1$-$C_4$ alkyl and ($C_1$-$C_4$ alkyl)OH;

$R_{23}$ is selected from the group consisting of H, F, $CO_2H$, OH, $C_1$-$C_6$ alkyl, ($C_1$-$C_4$ alkyl)OH, and ($C_1$-$C_4$ alkyl)$NH_2$;

$R_{24}$ is selected from the group consisting of H, F and $PO_3H_2$, or $R_{23}$ together with $R_{24}$ and the carbon to which they are attached form a carbonyl group; and $R_{15}$ is selected from the group consisting of hydroxy, phosphonate, and

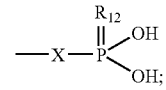

wherein X and $R_{12}$ is selected from the group consisting of O and S;

or a pharmaceutically acceptable salt or tautomer thereof are anticipated to have antagonist activity at the S1P3 receptor. In accordance with one embodiment, the $R_1$ substituent is located in the ortho position on the phenyl ring, and in one embodiment, the $R_1$ substituent is located in the meta position on the phenyl ring.

However compounds of the general structure

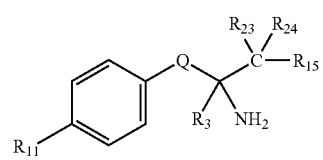

XI (wherein $R_{11}$ is located in the para-position) have exhibited activity as agonists of S1P activity. In particular compounds of Formula XI are provided as S1P agonists wherein $R_{11}$ is $C_5$-$C_{18}$ alkyl or $C_5$-$C_{18}$ alkenyl;

Q is selected from the group consisting of $C_3$-$C_6$ optionally substituted cycloalkyl, $C_3$-$C_6$ optionally substituted heterocyclic, $C_3$-$C_6$ optionally substituted aryl and $C_3$-$C_6$ optionally substituted heteroaryl;

$R_3$ is selected from the group consisting of H, $C_1$-$C_4$ alkyl and ($C_1$-$C_4$ alkyl)OH;

$R_{23}$ is selected from the group consisting of H, F, $CO_2H$, OH, $C_1$-$C_6$ alkyl, ($C_1$-$C_4$ alkyl)OH, and ($C_1$-$C_4$ alkyl)$NH_2$;

$R_{24}$ is selected from the group consisting of H, F and $PO_3H_2$, or $R_{23}$ together with $R_{24}$ and the carbon to which they are attached form a carbonyl group; and $R_{15}$ is selected from the group consisting of hydroxy, phosphonate, and

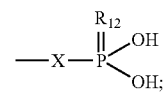

wherein X and $R_{12}$ are independently selected from the group consisting of O and S;

or a pharmaceutically acceptable salt or tautomer thereof and a pharmaceutically acceptable carrier. In one embodiment, a compound represented by Formula XI is provided as an S1P agonist wherein $R_{11}$ is $C_5$-$C_{18}$ alkyl or $C_5$-$C_{18}$ alkenyl;

Q is —NH(CO)—,

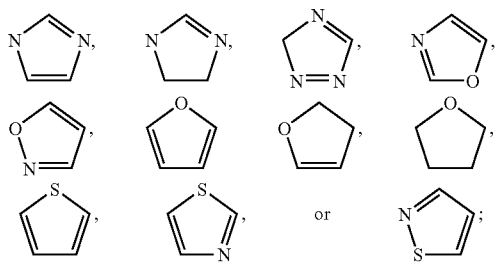

$R_3$ is selected from the group consisting of H, $C_1$-$C_4$ alkyl and ($C_1$-$C_4$ alkyl)OH;

$R_{24}$ is H;

$R_{23}$ is H or $C_1$-$C_4$ alkyl, and $R_{15}$ is selected from the group consisting of hydroxy, phosphonate, and

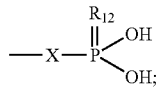

wherein X and $R_{12}$ are independently selected from the group consisting of O and S.

Compounds VPC23065, VPC23087 and VPC23075 are primary alcohols, i.e. $R_4$ of formula XII is hydroxy. These compounds demonstrate significant agonist activity at various S1P receptors. In particular, the S1P4 receptor binds to the primary alcohol S1P analogs with an $EC_{50}$ within a log order of the phosphorylated compounds. Since S1P4 is present on lymphocytes, the use of the primary alcohol analogs may be used for immuno-suppression. In addition, it is also hypothesized that the hydroxy moiety of the primary alcohols may be converted to phosphates in vivo. Therefore the primary alcohol S1P analogs of the present invention are all anticipated to serve as prodrug forms of active S1P receptor modulating compounds.

S1P is metabolized by a variety of conceivable routes including phosphatases, esterases or transported into cells. The S1P signal at receptors might be prolonged if the routes of degradation could be evaded or inhibited by S1P structural analogs. The S1P analogs of the present invention can be used, in accordance with one embodiment, to inhibit or evade endogenous S1P metabolic pathways including phosphotases, esterases, transporters and S1P acyl transferases. For example, those S1P analogs that lack an ester bond would be resistant to degradation by endogenous esterases. One embodiment of the present invention is directed to compounds that function as a S1P receptor agonists and antagonists that are resistant to hydrolysis by lipid phosphate phosphatases (LPPs) or are sub-type selective inhibitors of LPPs, and in particular are resistant to hydrolysis by sphingosine 1-phosphate phosphohydrolase. Previously described S1P mimetics contain a phosphate group, and thus are likely susceptible to hydrolysis by LPPs.

Alpha hydroxy phosphonates are well known phosphate mimetics. For example, the compounds used clinically to treat osteoporosis (pamidronate, alendronate) are alpha hydroxy bisphosphonates that are analogs of pyrophosphate. S1P analogs can be prepared wherein the phosphate moiety is replaced by an alpha substituted phosphonate, wherein the substituents are selected from the group consisting of H, OH, F, $CO_2H$, $PO_3H_2$ or double bonded oxygen. Accordingly, one aspect of the present invention is directed to lipid phosphate phosphatase resistant S1P analogs having the general structures:

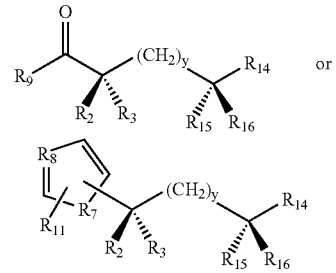

wherein $R_9$ is selected from the group consisting of —$NR_1$, and —$OR_1$;

$R_1$ is selected from the group consisting of $C_8$-$C_{22}$ alkyl, $C_8$-$C_{22}$ alkenyl, $C_8$-$C_{22}$ alkynyl and —$(CH_2)_n$-Z-$R_6$;

$R_{11}$ is —$(CH_2)_n$-Z-$R_6$; wherein n is an integer ranging from 0 to 10, Z is selected from the group consisting of aryl and heteroaryl and $R_6$ is selected from the group consisting of H, $C_1$-$C_{10}$ alkyl, $C_1$-$C_{20}$ alkoxy, $C_1$-$C_{20}$ alkylthio, and $C_1$-$C_{20}$ alkylamino;

$R_2$ and $R_3$ are independently selected from the group consisting of H, $NH_2$, OH, $C_1$-$C_6$ alkyl, —($C_1$-$C_4$ alkyl)OH, —($C_1$-$C_4$ alkyl)$NH_2$, —($C_1$-$C_4$ alkyl)aryl($C_0$-$C_4$ alkyl) and —($C_1$-$C_4$ alkyl)aryloxyaryl($C_0$-$C_4$ alkyl), wherein $R_2$ and $R_3$ are not the same and $R_2$ or $R_3$ is $NH_2$ y is an integer from 0-10;

$R_{14}$ is selected from the group consisting of

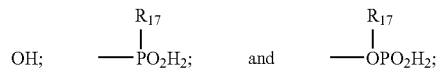

$R_{15}$ is selected from the group consisting of H, hydroxy, amino, COOH, halo, $PO_2H_2$; or $R_{15}$ and $R_{16}$ taken together form a keto group or a methylene group;

$R_{16}$ is selected from the group consisting of hydroxy, amino, COOH, halo, $PO_2H_2$; or $R_{15}$ and $R_{16}$ taken together with the carbon to which they are bound form a carbonyl or a methylene group; and $R_{17}$ is selected from the group consisting of O, S and NH. In one preferred embodiment, $R_9$ is —$NR_1$, wherein $R_1$ is $C_8$-$C_{22}$ alkyl or —$(CH_2)_n$-Z-$R_6$, y is 0 or 1, $R_{15}$ and $R_{16}$ are independently H, $C_1$-$C_4$ alkyl or hydroxyl, and $R_{14}$ is OH. In an alternative preferred embodiment, the compound has the general structure:

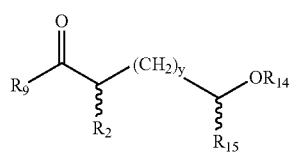

wherein $R_9$ is selected from the group consisting of —$NR_1$, and —$OR_1$;

$R_1$ is selected from the group consisting of $C_8$-$C_{22}$ alkyl, $C_8$-$C_{22}$ alkenyl, $C_8$-$C_{22}$ alkynyl and —$(CH_2)_n$-Z-$R_6$, wherein n is an integer ranging from 0 to 10, Z is selected from the group consisting of aryl and heteroaryl and $R_6$ is selected from the group consisting of H, $C_1$-$C_{10}$ alkyl, $C_1$-$C_{20}$ alkoxy, $C_1$-$C_{20}$ alkylthio, and $C_1$-$C_{20}$ alkylamino;

$R_2$ is $NH_2$ or OH;

y is an integer from 0-10;

$R_{14}$ is H or

$R_{15}$ is $NH_2$ or OH; and $R_{17}$ is selected from the group consisting of O, S and NH. In one preferred embodiment, $R_9$ is $-NR_1$, wherein $R_1$ is $C_8$-$C_{22}$ alkyl or $-(CH_2)_n$-Z-$R_6$, y is 0 or 1, and $R_{17}$ is O.

Lysophospholipids such as S1P and LPA, and their phosphate-containing analogs, are probably degraded by membrane bound lipid ectophosphohydrolases. This activity can be evaded by substituting phosphonate, α-substituted phosphonate, phosphothionate or other phosphate analogs as phosphate surrogates. Such compounds might also function as lipid ectophosphohydrolase inhibitors. Further, substitution of small alkyl groups (e.g. $C_1$-$C_4$ alkyl, $C_1$-$C_3$ alkylalcohol) at C-1 or C-2 might retard lipid ectophosphohydrolase cleavage by steric hindrance.

In accordance with one embodiment, an S1P receptor modulating compound is provided wherein the compound has the general structure:

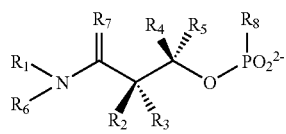

wherein $R_1$ is selected from the group consisting of alkyl, alkenyl, alkynyl, alkyl (optionally substituted aryl), alkyl (optionally substituted cycloalkyl), arylalkyl and arylalkyl (optionally substituted aryl) $R_7$ is H, O, or $R_1$ and $R_7$ taken together form an optionally substituted $C_3$-$C_6$ heteroaryl or optionally substituted $C_3$-$C_6$ heterocyclic group; $R_6$ is H, $C_1$-$C_4$ alkyl or $(CH_2)$aryl; $R_2$ and $R_3$ are independently selected from the group consisting of H, $NH_2$, OH, $C_1$-$C_6$ alkyl, $-(C_1$-$C_4$ alkyl)OH, and $-(C_1$-$C_4$ alkyl)$NH_2$; $R_4$ and $R_5$ are independently selected from the group consisting of H, $NH_2$, OH, $C_1$-$C_6$ alkyl, $-(C_1$-$C_4$ alkyl)OH, and $-(C_1$-$C_4$ alkyl)$NH_2$; $R_8$ is O, NH or S. In one embodiment, one of the $R_2$ and $R_3$ substituents is $NH_2$ while the other is $CH_3$ and $R_6$ is H. In another embodiment, one of the $R_2$ and $R_3$ substituents is $NH_2$ while the other is H and one of the $R_4$ and $R_5$ substituents is $CH_3$ while the other is H, and $R_6$ is H.

In accordance with one embodiment of the invention, a compound is provided that could be converted by phosphorylation to an S1P receptor modulating compound. The compound has the general structure:

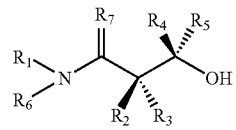

wherein $R_1$ is selected from the group consisting of alkyl, alkenyl, alkynyl, alkyl (optionally substituted aryl), alkyl (optionally substituted cycloalkyl), arylalkyl and arylalkyl (optionally substituted aryl) $R_7$ is H, O, or $R_1$ and $R_7$ taken together form an optionally substituted $C_3$-$C_6$ heteroaryl or optionally substituted $C_3$-$C_6$ heterocyclic group; $R_6$ is H, $C_1$-$C_4$ alkyl or $(CH_2)$aryl; $R_2$ and $R_3$ are independently selected from the group consisting of H, $NH_2$, OH, $C_1$-$C_6$ alkyl, $-(C_1$-$C_4$ alkyl)OH, and $-(C_1$-$C_4$ alkyl)$NH_2$; $R_4$ and $R_5$ are independently selected from the group consisting of H, $NH_2$, OH, $C_1$-$C_6$ alkyl, $-(C_1$-$C_4$ alkyl)OH, and $-(C_1$-$C_4$ alkyl)$NH_2$. In one embodiment, one of the $R_2$ and $R_3$ substituents is $NH_2$ while the other is $CH_3$ and $R_6$ is H. In another embodiment, one of the $R_2$ and $R_3$ substituents is $NH_2$ while the other is H and one of the $R_4$ and $R_5$ substituents is $CH_3$ while the other is H, and $R_6$ is H.

In accordance with one embodiment, an S1P receptor modulating compound is provided wherein the compound has the general structure:

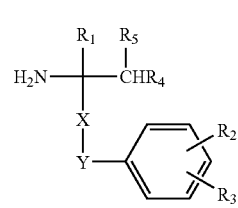

wherein $R_1$ is selected from the group consisting of $C_1$-$C_6$ alkyl, $C_1$-$C_6$ alkenyl, $C_1$-$C_6$ alkynyl, or $C_1$-$C_6$ alkyl, $C_1$-$C_6$ alkenyl, $C_1$-$C_6$ alkynyl optionally substituted with OH;

$R_2$ is $C_5$-$C_{10}$ alkyl, $C_5$-$C_{10}$ alkoxy, $(CH_2)_nO(CH_2)_m$, $C_5$-$C_{10}$ (optionally substituted aryl), $C_5$-$C_{10}$ (optionally substituted heteroaryl), $C_5$-$C_{10}$ (optionally substituted cycloalkyl), $C_5$-$C_{10}$ alkoxy (optionally substituted aryl), $C_5$-$C_{10}$ alkoxy (optionally substituted heteroaryl) and $C_5$-$C_{10}$ alkoxy (optionally substituted cycloalkyl);

$R_3$ is selected from the group consisting of H, halo, $C_1$-$C_6$ alkoxy, $C_1$-$C_6$ alkyl, $(CH_2)_yNH_2$, $(CH_2)_y$cyano and $C_1$-$C_6$ alkylthio;

$R_4$ is selected from the group consisting of hydroxy, phosphate, methylene phosphonate, α-substituted methylene phosphonate, thiophosphate, thiophosphonate and other phosphate analogs and phosphonate analogs or a pharmaceutically acceptable salt thereof;

$R_5$ is selected from the group consisting of H, halo, $C_1$-$C_4$ alkyl and haloalkyl;

X is $CR_8R_9$;

Y is selected from the group consisting of $CR_8R_9$, carbonyl, NH, O or S;

$R_8$ and $R_9$ are independently selected from the group consisting of H, halo and hydroxy;

n and m are integers independently ranging from 5-10, and y is an integer ranging from 0-10 with the proviso that X and Y are not both methylene. In one embodiment, a compound of the Formula IX is provided wherein $R_5$ is selected from the group consisting of H, F, methyl and ethyl. In another embodiment, a compound of the Formula IX is provided wherein X is selected from the group consisting of $CH_2$, CHF, $CF_2$, and CHOH. In a further embodiment, a compound of the Formula IX is provided wherein $R_1$ is selected from the group consisting of $CH_3$, $CH_2CH_3$, $CH_2OH$, $CH_2CH_2OH$ and $CH_2CH_2CH_2OH$;

$R_2$ is $C_5$-$C_{10}$ alkyl, $C_5$-$C_{10}$ alkoxy, $(CH_2)_nO(CH_2)_m$, $C_5$-$C_{10}$ (optionally substituted aryl), $C_5$-$C_{10}$ (optionally substituted heteroaryl) and $C_5$-$C_{10}$ (optionally substituted cycloalkyl);

$R_3$ and $R_5$ are H;

$R_4$ is selected from the group consisting of hydroxy, phosphate and methylene phosphonate;

X is $CH_2$;

Y is selected from the group consisting of carbonyl, NH, O and S; and n and m are integers independently ranging from 5-10. In one embodiment a compound of Formula IX is provided wherein $R_1$ is —$CH_3$, or —$CH_2CH_3$; $R_2$ is $C_5$-$C_{10}$ alkyl; $R_3$ and $R_5$ are H; $R_4$ is hydroxy or phosphate X is $CH_2$; and Y is selected from the group consisting of carbonyl, NH and O.

The present invention also encompasses the pharmaceutically acceptable salts of the compounds of the Formula IX including salts with inorganic acids, such as hydrochloride, hydrobromide and sulfate, salts with organic acids, such as acetate, fumarate, maleate, benzoate, citrate, malate, methanesulfonate and benzenesulfonate salts, and when a carboxy group is present, salts with metals such as sodium, potassium, calcium and aluminium, salts with amines, such as triethylamine and salts with dibasic amino acids, such as lysine. The compounds and salts of the present invention encompass hydrate and solvate forms.

In one embodiment, an S1P modulating compound is provided having the general structure:

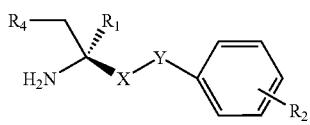

wherein $R_1$ is methyl or ethyl;

$R_2$ is selected from the group consisting of $C_5$-$C_{10}$ alkyl, $(CH_2)_nO(CH_2)_m$, $C_5$-$C_{10}$ (optionally substituted aryl), $C_5$-$C_{10}$ (optionally substituted heteroaryl), $C_5$-$C_{10}$ (optionally substituted cycloalkyl), $C_5$-$C_{10}$ alkoxy (optionally substituted aryl), $C_5$-$C_{10}$ alkoxy (optionally substituted heteroaryl) and $C_5$-$C_{10}$ alkoxy (optionally substituted cycloalkyl);

$R_4$ is $OPO_3H_2$ or OH;

n and m are integers independently ranging from 0 to 10;

X is a methylene group optionally substituted with one or two fluorine atoms or a secondary alcohol in either stereoconfiguration;

Y is a carbonyl group, —O—, —NH— or a methylene group that is optionally substituted with one or two fluorine atoms, or a secondary alcohol in either stereoconfiguration, with the proviso that X and Y are not both methylene. In one embodiment, the compound of Formula X is provided wherein $R_1$ is methyl or ethyl; $R_2$ is $C_5$-$C_{10}$ alkyl or $(CH_2)_nO(CH_2)_m$; $R_4$ is $OPO_3H_2$ or OH; X is methylene; Y is a carbonyl group, —O— or —NH—; and n and m are integers independently ranging from 0 to 10. More particularly, in one embodiment, compounds of Formula X are provided wherein $R_1$ is methyl; $R_2$ is $C_5$-$C_8$ alkyl and located in the para position; $R_4$ is $OPO_3H_2$ or OH; X is methylene; and Y is a carbonyl group or —NH—.

In accordance with one embodiment, compounds suitable for use in accordance with the present invention include:

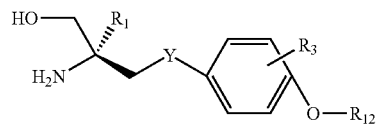

wherein $R_1$ is selected from the group consisting of —$CH_3$, —$CH_2CH_3$, $CH_2OH$, $CH_2CH_2OH$; $R_3$ is selected from the group consisting of H, $C_1$-$C_6$ alkoxy and $C_1$-$C_6$ alkyl; Y is selected from the group consisting of CHOH, $CF_2$, CFH, carbonyl, NH, O and S; and $R_{12}$ is H, $C_1$-$C_6$ alkoxy or $C_1$-$C_6$ alkyl. More particularly, suitable compounds include the following compounds:

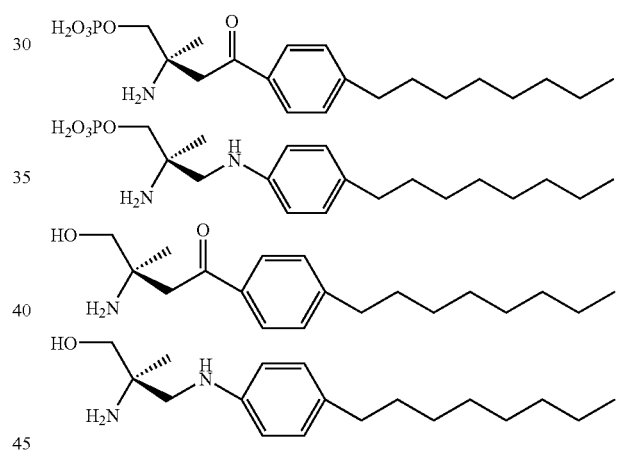

The present invention also encompasses compounds general structure:

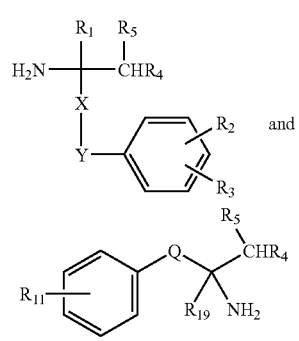

wherein $R_1$ and $R_1$ are independently selected from the group consisting of $C_1$-$C_{12}$ alkyl, $C_2$-$C_{12}$ alkenyl, $C_2$-$C_{12}$ alkynyl;

$R_{1g}$ is selected from the group consisting of $C_1$-$C_6$ alkyl and ($C_1$-$C_6$ alkyl)OH;

Q is

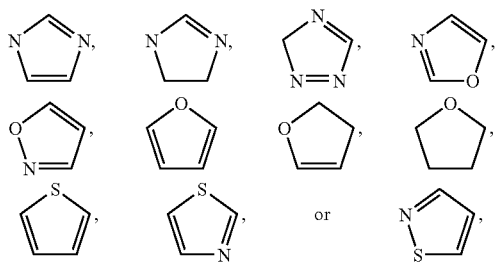

$R_2$ is $C_5$-$C_{12}$ alkyl, $C_2$-$C_{12}$ alkenyl $(CH_2)_nO(CH_2)_m$, $C_5$-$C_{10}$ (optionally substituted aryl), $C_5$-$C_{10}$ (optionally substituted heteroaryl) and $C_5$-$C_{10}$ (optionally substituted cycloalkyl);

$R_3$ is selected from the group consisting of H, halo, $C_1$-$C_6$ alkoxy, $C_1$-$C_6$ alkyl, $(CH_2)_nNH_2$, $(CH_2)$, cyano and $C_1$-$C_6$ alkylthio;

$R_4$ is selected from the group consisting of hydroxy,

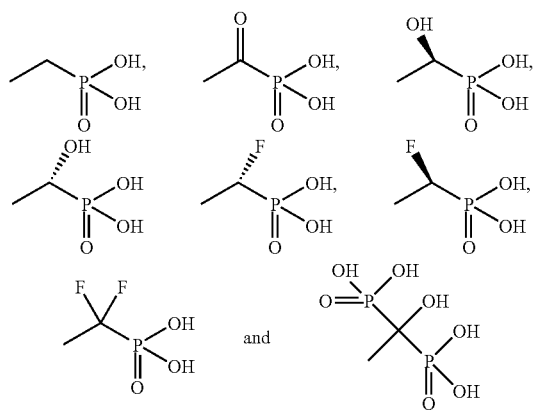

$R_5$ is selected from the group consisting of H, F, methyl or ethyl;

X is $CH_2$, CHF, $CF_2$ or CHOH;

Y is selected from the group consisting of CHF, $CF_2$, CHOH, carbonyl, NH, O or S;

n and m are integers independently ranging from 0-10, with the proviso that X and Y are not both methylene. In one embodiment, $R_1$ is methyl or ethyl, $R_2$ is $C_5$-$C_{10}$ alkyl, $C_5$-$C_{10}$ aryl or $C_5$-$C_{10}$ alkoxy, $R_3$ is H, $C_1$-$C_6$ alkoxy or $C_1$-$C_6$ alkyl, $R_4$ is as defined immediately above, $R_5$ is H, X is methylene and Y is a carbonyl group, —O— or —NH—; or a pharmaceutically acceptable salt or tautomer thereof. In another embodiment, Q is

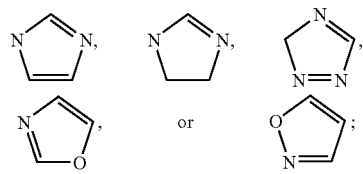

$R_2$ and $R_1$ are independently selected from the group consisting of $C_5$-$C_{12}$ alkyl and $C_2$-$C_{12}$ alkenyl and $R_{15}$ is OH.

The compounds of the present invention are anticipated to be high affinity agonists (or antagonists) at various sphingosine I-phosphate receptors of the 'Edg' family. The compounds of the present invention are also expected to evoke lymphopenia when introduced into rodents or humans. Thus the compounds of the invention are immune modulators and are useful in treatment or prophylaxis of pathologies mediated by lymphocyte actions including acute or chronic rejection of tissue grafts such as organ transplants or graft vs. host disease as well as autoimmune diseases. Autoimmunue diseases that could be treated with compounds of the invention include, but are not limited to: systemic lupus erythematosus, multiple sclerosis, rheumatoid arthritis, inflammatory bowel diseases including Crohn's disease and ulcerative colitis, type I diabetes, uveitis, psoriasis and myasthenia gravis. The compounds of the invention are useful also in treating inflammatory disorders such as atopic asthma, inflammatory glomerular injury and ischemia-reperfusion injury.

Compounds of formula XII wherein $R_{15}$ is hydroxy are primary alcohols. It is hypothesized that the hydroxy moiety of the primary alcohols is converted to phosphates in vivo. Therefore, the primary alcohol S1P analogs of the present invention are expected to serve as prodrug forms of active S1P receptor modulating compounds. Therefore, in accordance with one embodiment pharmaceutical compositions comprising the primary alcohol S1P analogs of the present invention are administered to treat patients for a variety of ailments or conditions, including the use of the compounds for immunomodulation to prevent or diminish tissue graft rejection.

S1P is metabolized by a variety of conceivable routes including phosphatases, esterases or transported into cells. The S1P signal at receptors might be prolonged if the routes of degradation could be evaded or inhibited by S1P structural analogs. The S1P analogs of the present invention can be used, in accordance with one embodiment, to inhibit or evade endogenous S1P metabolic pathways including phosphotases, esterases, transporters and S1P acyl transferases. For example, those S1P analogs that lack an ester bond would be resistant to degradation by endogenous esterases. One embodiment of the present invention is directed to compounds that function as a S1P receptor agonists and antagonists that are resistant to hydrolysis by lipid phosphate phosphatases (LPPs) or are sub-type selective inhibitors of LPPs, and in particular are resistant to hydrolysis by sphingosine 1-phosphate phosphohydrolase. Previously described S1P mimetics contain a phosphate group, and thus are likely susceptible to hydrolysis by LPPs.

Alpha hydroxy phosphonates are well known phosphate mimetics. For example, the compounds used clinically to treat osteoporosis (pamidronate, alendronate) are alpha hydroxy bisphosphonates that are analogs of pyrophosphate. S1P analogs can be prepared wherein the phosphate moiety is replaced by an alpha hydroxy phosphonate. Accordingly, one aspect of the present invention is directed to lipid phosphate phosphatase resistant S1P analogs having the general structures of Formula IX or I wherein $R_4$ or $R_{15}$, respectively, are selected from the group consisting of

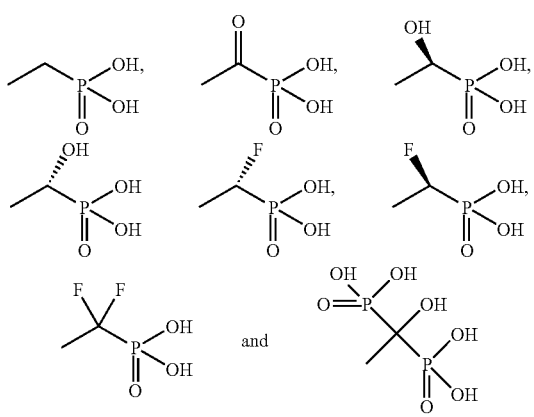

The compounds of the present invention can be used for immuno-modulation as well as in anti-angiogenesis therapy, most particularly as applied in therapy of neoplastic disease. In another embodiment, the SP1 analogs of the present invention are used in the protection of female gonads during radiation therapy such as applied to the abdomen in the course of treatment of neoplastic diseases.

Lysophospholipids, sphingosine-1-phosphate (S1P) and lysophosphatidic acid (LPA), stimulate cellular proliferation and affect numerous cellular functions by signaling through G protein-coupled endothelial differentiation gene-encoded (S1P) receptors. Accordingly, the S1P receptor agonists disclosed in the present invention are anticipated to have utility in a variety of clinical settings including but not limited to the acceleration of wound healing (including corneal wounds), the promotion of myelination (oligodendrocyte cell function) and for immuno-modulation. In particular, LPA has been reported (Balazs et al. *Am J Physiol Regul Integr Comp Physiol*, 2001 280(2):R466-472) as having activity in accelerating wound closing and increasing neoepithelial thickness.

In accordance with one embodiment of the present invention, a pharmaceutical composition comprising one or more of the S1P receptor agonists of the present invention is administered to a mammalian species (including humans) to enhance wound repair, improve neuronal function or enhance an immune response of that species. It has also been reported that S1P inhibits fibrosis in various organs. Accordingly, the S1P receptor agonists of the present invention can be used to prevent/treat diseases associated with fibrosis of organs such as pulmonary fibrosis, interstitial pneumonia, chronic hepatitis, hepatic cirrhosis, chronic renal insufficiency or kidney glomerular sclerosis. In one embodiment, a composition comprising an S1P receptor agonist of the present invention is used to treat wounds, including burns, cuts, lacerations, surgical incisions, bed sores, and slow-healing ulcers such as those seen in diabetics. Typically the composition is administered locally as a topical formulation, however other standard routes of administration are also acceptable.

In addition, it is believed that the S1P analogs of the present invention mobilize lymphocytes and increase their homing to secondary lymphoid tissues. Thus, the present analogs can be used to direct lymphocytes away from transplanted organs (allografts) or healthy cells (e.g. pancreatic islets (type I diabetes), myelin sheathing (multiple sclerosis)), or other tissues that may be subjected to an undesirable immuno response and thus decrease damage to such tissues from the immune system.

In another embodiment, the S1P receptor modulating compounds of the present invention are administered to a subject to treat or prevent a disorder of abnormal cell growth and differentiation as well as inflammatory diseases. These disorders include, but are not limited to, Alzheimer's disease, aberrant corpus luteum formation, osteoarthritis, osteoporosis, anovulation, Parkinson's disease, multiple sclerosis, rheumatoid arthritis and cancer. In accordance with one embodiment, an S1P antagonist is administered to a patient to treat a disease associated with abnormal growth. In one embodiment, a composition comprising a compound of the general structure:

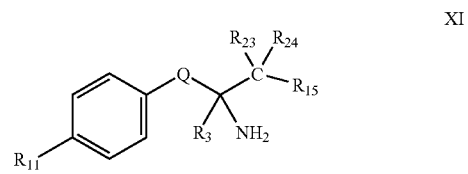

XI wherein $R_{11}$ is $C_5$-$C_{18}$ alkyl or $C_5$-$C_{18}$ alkenyl located in the meta or para position;

Q is selected from the group consisting of $C_3$-$C_6$ optionally substituted cycloalkyl, $C_3$-$C_6$ optionally substituted heterocyclic, $C_3$-$C_6$ optionally substituted aryl $C_3$-$C_6$ optionally substituted heteroaryl, $CH_2CH_2$ and —NH(CO)—;

$R_3$ is selected from the group consisting of H, $C_1$-$C_4$ alkyl and ($C_1$-$C_4$ alkyl)OH;

$R_{23}$ is selected from the group consisting of H, F, $CO_2H$, OH, $C_1$-$C_6$ alkyl, ($C_1$-$C_4$ alkyl)OH, and ($C_1$-$C_4$ alkyl)$NH_2$;

$R_{24}$ is selected from the group consisting of H, F and $PO_3H_2$, or $R_{23}$ together with $R_{24}$ and the carbon to which they are attached form a carbonyl group; and $R_{15}$ is selected from the group consisting of hydroxy, phosphonate, and

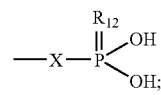

wherein X and $R_{12}$ is selected from the group consisting of O and S;

or a pharmaceutically acceptable salt or tautomer thereof and a pharmaceutically acceptable carrier is administered to treat a patient suffering from a disease associated with abnormal cell growth.

In one embodiment, the compound of Formula XI is administered to treat a patient suffering from a disease associated with abnormal cell growth wherein Q is —NH(CO)—,

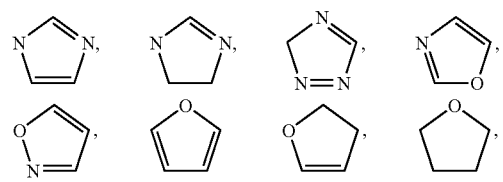

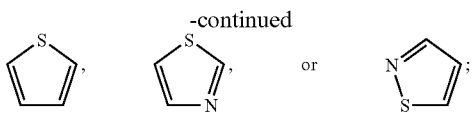

$R_{24}$ is H;
$R_{23}$ is H or $C_1$-$C_4$ alkyl;
$R_{15}$ is selected from the group consisting of hydroxy and

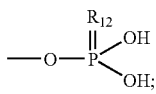

wherein $R_{12}$ is O or S, and in a further embodiment Q is

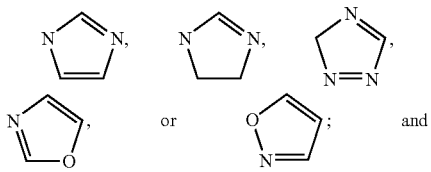

$R_{15}$ is OH;
or a pharmaceutically acceptable salt or tautomer thereof.

In addition, it is believed that the S1P analogs of the present invention mobilize lymphocytes and increase their homing to secondary lymphoid tissues. Thus, the present analogs can be used to direct lymphocytes away from transplanted organs (allografts) or healthy cells (e.g., pancreatic islets (type I diabetes), myelin sheathing (multiple sclerosis)), or other tissues that may be subjected to an undesirable immuno response and thus decrease damage to such tissues from the immune system.

In accordance with one embodiment, the S1P analogs of the present invention are used for immuno-modulation, wherein immuno-modulation refers to an affect on the functioning of the immune system and includes lymphocyte trafficking. In accordance with one embodiment, an S1P analog of the present invention that exhibits potent agonist activity at S1P1 is administered to a warm blooded vertebrate, including a human, to induce immuno-modulation in a patient in need thereof. In one embodiment the S1P analog is specific or has enhanced activity at the S1P1 receptor subtype relative to one or more of the other S1P receptor subtypes.

In one embodiment of the present invention, the S1P analogs of the present invention are used as immuno-modulators to alter immune system activities and prevent damage to healthy tissue that would otherwise occur in autoimmune diseases and in organ transplantation. In particular, the compounds can be administered to patients as part of the treatment associated with organ transplantation, including pancreas, pancreatic islets, kidney, heart and lung transplantations. The S1P analogs can be administered alone or in combo with known immuno-suppressants such as cyclosporine, tacrolimus, rapamycin, azathioprine, cyclophosphamide, methotrexate and corticosteroids such as cortisolo, cortisone, desoxymetasone, betametasone, desametasone, flunisolide, prednisolone, prednisone, amcinomide desonide, methylprednisolone, triamcinolone, and alclometasone.

Additionally, the S1P analogs of the present invention can be administered to patients suffering from an autoimmune disease to treat that disease. Examples of diseases considered to be autoimmune in nature are: type I diabetes, systemic lupus erythematosus, multiple sclerosis, rheumatoid arthritis, inflammatory bowel disease including colitis and Crohn's disease, glomerulonephritis, uveitis, Hashimoto's thyroiditis, myasthenia gravis, autoimmune hemolytic anemia, autoimmune thrombocytopenic purpura, autoimmune hepatitis and Wegner's granuloma.

In accordance with one embodiment, an immuno-modulation therapy is provided for treating mammals, including humans, in need thereof. The method comprises the steps of administering to said mammal an effective amount of a compound represented by the formula:

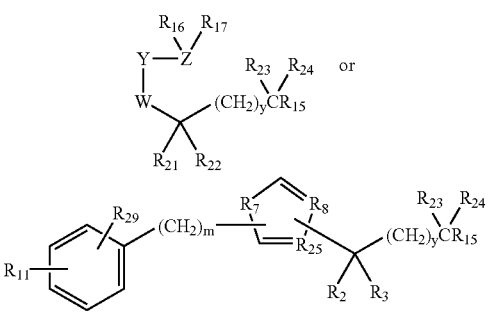

wherein
W is $CR_{27}R_{28}$ or $(CH_2)_n NH(CO)$;
wherein $R_{27}$ and $R_{28}$ are independently selected from the group consisting of H, halo and hydroxy;
Y is selected from the group consisting of a bond, $CR_9R_{10}$, carbonyl, NH, O or S;
wherein $R_9$ and $R_{10}$ are independently selected from the group consisting of H, halo, hydroxy and amino;
Z is $CH_2$, aryl, halo substituted aryl or heteroaryl;
$R_{11}$ and $R_{16}$ are independently selected from the group consisting of $C_1$-$C_{18}$ alkyl, $C_2$-$C_{18}$ alkenyl, $C_2$-$C_{18}$ alkynyl, $C_5$-$C_{18}$ alkoxy, $(CH_2)_pO(CH_2)_q$, $C_5$-$C_{10}$ (aryl)$R_{20}$, $C_5$-$C_{10}$ (heteroaryl)$R_{20}$, $C_5$-$C_{10}$ (cycloalkyl)$R_{20}$, $C_5$-$C_{10}$ alkoxy(aryl)$R_{20}$, $C_5$-$C_{10}$ alkoxy(heteroaryl)$R_{20}$ and $C_5$-$C_{10}$ alkoxy(cycloalkyl)$R_{20}$;
wherein $R_{20}$ is H or $C_1$-$C_{10}$ alkyl;
$R_{29}$ is H or halo;
$R_{17}$ is selected from the group consisting of H, halo, $NH_2$, $C_1$-$C_6$ alkyl, $C_1$-$C_6$ alkoxy, $C_1$-$C_6$ alkylamino, $C_1$-$C_6$ alkylcyano and $C_1$-$C_6$ alkylthio;
$R_2$ and $R_{21}$ are both $NH_2$;
$R_3$ is selected from the group consisting of H, $C_1$-$C_6$ alkyl, ($C_1$-$C_4$ alkyl)OH, and ($C_1$-$C_4$ alkyl)$NH_2$;
$R_{22}$ is selected from the group consisting of $C_1$-$C_6$ alkyl, ($C_1$-$C_4$ alkyl)OH and ($C_1$-$C_4$ alkyl)$NH_2$;
$R_{23}$ is selected from the group consisting of H, F, $CO_2H$, OH, $C_1$-$C_6$ alkyl, ($C_1$-$C_4$ alkyl)OH, and ($C_1$-$C_4$ alkyl)$NH_2$;
$R_{24}$ is selected from the group consisting of H, F and $PO_3H_2$, or $R_{23}$ together with $R_{24}$ and the carbon to which they are attached form a carbonyl group;
$R_{25}$, $R_7$ and $R_8$ are independently selected from the group consisting of O, S, $CHR_{26}$, $CHR_{26}$, $NR_{26}$, and N;
wherein $R_{26}$ is H, F or $C_1$-$C_4$ alkyl;
$R_{15}$ is selected from the group consisting of hydroxy, phosphonate, and

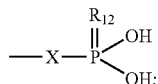

wherein $R_{12}$ is selected from the group consisting of O, NH and S;
X is selected from the group consisting of O, NH and S;
y and m are integers independently ranging from 0 to 4;
p and q are integers independently ranging from 1 to 10;
n is an integer ranging from 0 to 10;
or a pharmaceutically acceptable salt or tautomer thereof, with the proviso that W and Y are not both methylene. In one embodiment, the compound has the general structure of Formula II-VII as described herein to treat a patient by suppressing the immune system and diminishing damage to healthy tissue that would otherwise occur in autoimmune diseases and in organ transplantation.

In one embodiment, the immuno-modulating compound has the general structure:

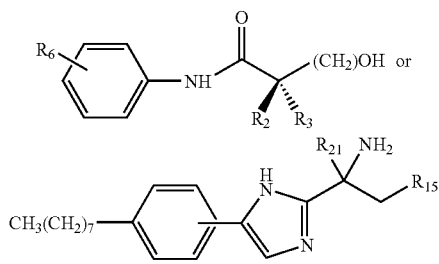

wherein $R_6$ is selected from the group consisting of $C_1$-$C_{10}$ alkyl and $R_2$ and $R_3$ are independently selected from the group consisting of H, and $NH_2$ with the proviso that $R_2$ and $R_3$ are not the same, and either $R_2$ or $R_3$ is $NH_2$; $R_{21}$ is selected from the group consisting of $C_1$-$C_6$ alkyl, ($C_1$-$C_4$ alkyl)OH and ($C_1$-$C_4$ alkyl)$NH_2$; and $R_{15}$ is selected from the group consisting of hydroxy, phosphonate, and

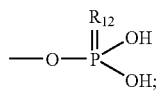

wherein $R_{12}$ is selected from the group consisting of O, NH and S; as well as pharmaceutically acceptable salts or tautomers of such compounds.

The dosage to be used is, of course, dependent on the specific disorder to be treated, as well as additional factors including the age, weight, general state of health, severity of the symptoms, frequency of the treatment and whether additional pharmaceuticals accompany the treatment. The dosages are in general administered several times per day and preferably one to three times per day. The amounts of the individual active compounds are easily determined by routine procedures known to those of ordinary skill in the art.

S1P also acts as a survival factor in many cell types. In particular, S1P receptor agonists are anticipated to have activity in protecting cells and tissues from hypoxic conditions. In accordance with one embodiment, the S1P antagonists of the present invention are administered to treat cells and tissues exposed to hypoxic conditions, including injury sustained as a result of ischemia. In accordance with one embodiment, the S1P analogs exhibiting S1P receptor antagonist activity can be used to treat ischemia reperfusion type injury. Interference with the supply of oxygenated blood to tissues is defined as ischemia. The effects of ischemia are known to be progressive, such that over time cellular vitality continues to deteriorate and tissues become necrotic. Total persistent ischemia, with limited oxygen perfusion of tissues, results in cell death and eventually in coagulation-induced necrosis despite reperfusion with arterial blood. A substantial body of evidence indicates that a significant proportion of the injury associated with ischemia is a consequence of the events associated with reperfusion of ischemic tissues, hence the term reperfusion injury.

The present invention is also directed to pharmaceutical compositions comprising the S1P receptor modulating compounds of the present invention. More particularly, such S1P receptor agonists and antagonists can be formulated as pharmaceutical compositions using standard pharmaceutically acceptable carriers, fillers, solublizing agents and stabilizers known to those skilled in the art. Pharmaceutical compositions comprising the S1P receptor agonists and/or antagonists are administered to an individual in need thereof by any number of routes including, but not limited to, topical, oral, intravenous, intramuscular, intra-arterial, intramedullary, intrathecal, intraventricular, transdermal, subcutaneous, intraperitoneal, intranasal, enteral, topical, sublingual, or rectal means. The oral route is typically employed for most conditions requiring the compounds of the invention. Preference is given to intravenous injection or infusion for the acute treatments. For maintenance regimens the oral or parenteral, e.g. intramuscular or subcutaneous, route is preferred. In accordance with one embodiment, a composition is provided that comprises an S1P analog of the present invention and albumin, more particularly, the composition comprises an S1P analog of the present invention, a pharmaceutically acceptable carrier and 0.1-1.0% albumin. Albumin functions as a buffer and improves the solubility of the compounds.

The invention also provides a pharmaceutical pack or kit comprising one or more containers filled with one or more of the ingredients of the pharmaceutical compositions of the invention. In accordance with one embodiment, a kit is provided for treating a patient in need of immuno-modulation. In this embodiment the kit comprises one or more of the S1P analogs of the present invention and may also include one or more known immuno-supressants. These pharmaceuticals can be packaged in a variety of containers, e.g., vials, tubes, microtiter well plates, bottles, and the like. Other reagents can be included in separate containers and provided with the kit; e.g., positive control samples, negative control samples, buffers, cell culture media, etc. Preferably, the kits will also include instructions for use.

The present invention is also directed to methods for discovering agonists and antagonists of the interaction between S1P and the S1P receptor. Such compounds are identified by using an assay for detecting S1P receptor activity (such as the [Y-35 S]GTP binding assay) and assaying for activity in the presence of S1P and the test compound. More particularly, in the method described by Traynor and Nahorski, 1995, Mol. Pharmacol. 47: 848-854, incorporated herein by reference, G-protein coupling to membranes can be evaluated by measuring the binding of labeled GTP.

For example, samples comprising membranes isolated from cells expressing an S1P polypeptide can be incubated in a buffer promoting binding of the polypeptide to ligand (i.e.

S1P), in the presence of radiolabeled GTP and unlabeled GDP (e.g., in 20 mM HEPES, pH 7.4, 100 mM NaCl, and 10 mM MgCl$_2$, 80 pM $^{35}$S-GTPγS and 3 μM GDP), with and without a candidate modulator. The assay mixture is incubated for a suitable period of time to permit binding to and activation of the receptor (e.g., 60 minutes at 30° C.), after which time unbound labeled GTP is removed (e.g., by filtration onto GF/B filters). Bound, labeled GTP can be measured by liquid scintillation counting. A decrease of 10% or more in labeled GTP binding as measured by scintillation counting in a sample containing a candidate modulator, relative to a sample without the modulator, indicates that the candidate modulator is an inhibitor of S1P receptor activity.

A similar GTP-binding assay can be performed without the presence of the ligand (i.e. S1P) to identify agents that act as agonists. In this case, ligand-stimulated GTP binding is used as a standard. An agent is considered an agonist if it induces at least 50% of the level of GTP binding induced by S1P when the agent is present at 10 uM or less, and preferably will induce a level which is the same as or higher than that induced by ligand.

GTPase activity can be measured by incubating cell membrane extracts containing an S1P receptor with $\gamma^{32}$P-GTP. Active GTPase will release the label as inorganic phosphate, which can be detected by separation of free inorganic phosphate in a 5% suspension of activated charcoal in 20 mM H$_3$PO$_4$, followed by scintillation counting. Controls would include assays using membrane extracts isolated from cells not expressing an S1P receptor (e.g., mock-transfected cells), in order to exclude possible non-specific effects of the candidate modulator. In order to assay for the effect of a candidate modulator on S1P-regulated GTPase activity, cell membrane samples can be incubated with a ligand (e.g., S1P), with and without the modulator, and a GTPase assay can be performed as described above. A change (increase or decrease) of 10% or more in the level of GTP binding or GTPase activity relative to samples without modulator is indicative of S1P modulation by a candidate modulator.

Identified S1P receptor agonists and antagonists can be used to treat a variety of human diseases and disorders, including, but not limited to the treatment of infections such as bacterial, fungal, protozoan and viral infections, particularly infections caused by HIV-1 or HIV-2; pain; cancers; diabetes, obesity; anorexia; bulimia; asthma; Parkinson's disease; acute heart failure; hypotension; hypertension; urinary retention; osteoporosis; angina pectoris; myocardial infarction; stroke; ulcers; asthma; allergy; benign prostatic hypertrophy; migraine; vomiting; psychotic and neurological disorders, including anxiety, schizophrenia, manic depression, depression, delirium, dementia, and severe mental retardation.

EXAMPLE 1

Chemical Syntheses of S1P Analogs

To develop good mimetics for S1P, a synthetic route was designed that had several aspects in mind (Scheme 1). First, butoxycarbonyl protected L-serine was chosen as starting material primarily because it retrosynthetically resembled the linker region of S1P. In addition, the starting material is a cheap and commercially available protected amino acid. Secondly, chemodivergence was taken into consideration. Coupling of the long chain was performed late in the synthesis so that several chain lengths could be prepared from a common intermediate. Another important issue to address was the overwhelming insolubility of the final compounds. Due to this insolubility, the target molecules could not be purified by chromatography or crystallization methods, nor could they tolerate a simple workup. It was therefore necessary to design a final step that quantitatively generated only the target product, and allowed for removal of excess reagents under vacuum. This was accomplished by employing trifluoroacetic acid deprotection at the end of the route.

The syntheses of the S1P analogs described in the synthetic schemes of Example 1 were accomplished using solvents purified by filtration through alumina (activity J) and unless otherwise indicated all reactions were conducted at room temperature. All reactions were performed under an inert atmosphere and all products were purified using 230-400 mesh silica gel. Each product was analyzed by thin layer chromatography (single spot) and spectroscopic methods including $^1$H NMR, $^{13}$C NMR, and mass spectrometry. The assigned structures of the S1P analogs were consistent with all spectral data obtained. All final products were obtained as the TFA salts.

Synthesis of (2S) S1P Analogs VPC22041, 51, 53, and 63

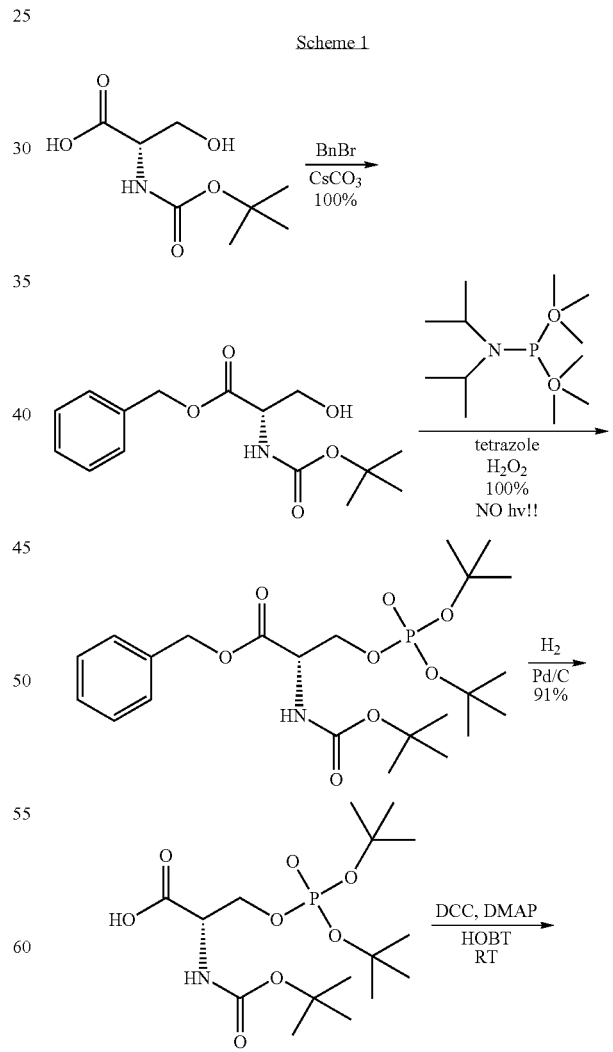

Scheme 1

-continued

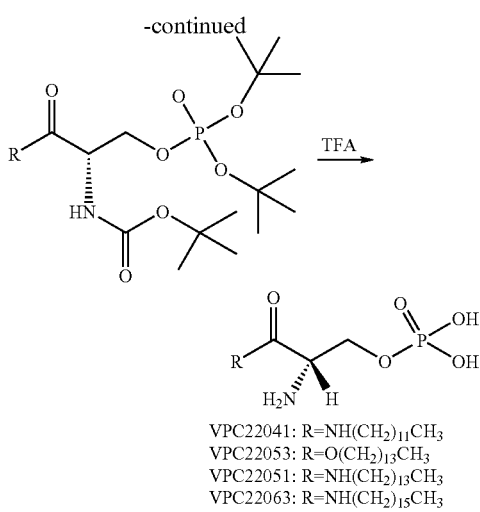

VPC22041: R=NH(CH$_2$)$_{11}$CH$_3$
VPC22053: R=O(CH$_2$)$_{13}$CH$_3$
VPC22051: R=NH(CH$_2$)$_{13}$CH$_3$
VPC22063: R=NH(CH$_2$)$_{15}$CH$_3$

| Compound | R | % Yields | | | | |
|---|---|---|---|---|---|---|
| | | A | B | C | D | E |
| VPC22041 | n-C$_{12}$H$_{25}$NH | 100 | 100 | 91 | 33 | 100 |
| VPC22051 | n-C$_{14}$H$_{29}$NH | 100 | 100 | 91 | 41 | 96 |
| VPC22053 | n-C$_{14}$H$_{29}$O | 100 | 100 | 91 | 15 | 100 |
| VPC22063 | n-C$_{16}$H$_{33}$NH | 100 | 100 | 91 | 26 | 100 |

Benzyl protection of N-Boc serine. To a stirring solution of N-Boc-(L)-Serine (4.87 mmol) in DMF (100 mL) was added cesium carbonate (5.11 mmol) and stirring was continued 30 min. Benzyl bromide (5.84 mmol) was then added and the resulting solution was stirred 12 h. The reaction mixture was then diluted with ethyl acetate (25 mL), washed with lithium bromide (3×15 mL), sodium bicarbonate (2×15 mL), and brine (2×15 mL). The organic layer was dried over sodium sulfate. The solvent was then removed under reduced pressure and the resulting tan oil was purified by flash chromatography, using 1:1 petroleum ether/diethyl ether, to afford the product (100%) as a white solid. R$_f$=0.26 (1:1 petroleum ether/diethyl ether).

Phosphorylation of resulting alcohol. For phosphorylation, reaction is performed in the absence of light, work up and columns are completed with as little light as possible. To a solution of the benzyl protected serine (1.98 mmol) in 1:1 CH$_2$Cl$_2$/THF (50 mL) was added tetrazole (3.96 mmol) and the resulting mixture was stirred 30 min. Di-tert-butyl-diisopropylphosphoramidite (3.96 mmol) was then added and the resulting reaction mixture was stirred 15 h. Hydrogen peroxide (7.92 mmol) was then added and the resulting mixture was stirred 3 h, cooled to 0° C., and quenched by addition of aqueous Na$_2$S$_2$O$_5$. The resulting solution was diluted with ethyl acetate (100 mL) and extracted with 50% aqueous Na$_2$S$_2$O$_5$ (2×20 mL). The organic layer was dried over sodium sulfate and the solvent was removed under reduced pressure to afford a tan oil. Flash chromatography, using 90:10 CHCl$_3$/acetone, provided the product (97%) as a clear oil. R$_f$=0.67 (90:10 CHCl$_3$/acetone).

Debenzylation of phosphorylated serine. To a solution of the phosphorylated serine (1.55 mmol) in 200 proof ethanol (25 mL) was added a catalytic amount of palladium on activated carbon. To the resulting solution was applied a positive pressure of hydrogen gas and the reaction mixture was stirred 12 h. The reaction mixture was then filtered through a plug of celite eluting with methanol and the solvent was removed under reduced pressure to yield the product (91%) as a slightly yellow oil. R$_f$=0 (90:10 CHCl$_3$/methanol).

Coupling of long chain amine with phosphorylated acid. A solution of the acid (0.252 mmol), a catalytic amount of 4-dimethylaminopyridine, 1-hydroxybenzotriazole hydrate (0.277 mmol), the long chain amine or alcohol (0.252 mmol), and 15 mL of CH$_2$Cl$_2$ was cooled to 0° C. with stirring. To the resulting solution at 0° C. was added dicyclohexylcarbodiimide (0.277 mmol) and the mixture was allowed to return to rt. with stirring continuing for 12 h. The reaction mixture was then recooled to 0° C. and filtered. The filtrate washed with sodium bicarbonate (3×10 mL), ammonium chloride (3×10 mL), and the organic layers were dried over sodium sulfate. The solvent was then removed under reduced pressure and the resulting yellow oil was purified by flash chromatography to afford the product.

VPC22041: 33%, white solid, R$_f$=0.78 (90:10 CHCl$_3$/methanol).

VPC22051: 41%, white solid, R$_f$=0.80 (90:10 CHCl$_3$/methanol).

VPC22053: 15%, white solid, R$_f$=0.20 (95:5 CHCl$_3$/acetone).

VPC22063: 26%, white solid, R$_f$=0.79 (90:10 CHCl$_3$/methanol).

Deprotection of N-Boc and phosphate groups. To a stirred solution of the protected final product (0.072 mmol) in CH$_2$Cl$_2$ (1 mL) was added trifluoroacetic acid (12.98 mmol) and stirring was continued 4 h. Under reduced pressure, solvent and excess trifluoroacetic acid were removed affording a brown oil. The oil was rinsed with ether and the solvent was removed under vacuum 5 times to afford the product.

VPC22041: 100%, white solid, R$_f$=0 (90:10 CHCl$_3$/methanol).

VPC22051: 96%, white solid, R$_f$=0 (90:10 CHCl$_3$/methanol).

VPC22053: 100%, white solid, R$_f$=0 (90:10 CHCl$_3$/methanol).

VPC22063: 100%, white solid, R$_f$=0 (90:10 CHCl$_3$/methanol).

For S1P analog VPC22051 the PyBOP coupling procedure (as used in VPC22135) was used in place of DCC coupling. The product was obtained in 15% yield as a clear oil.

Synthesis of (2R) S1P Analog VPC22135

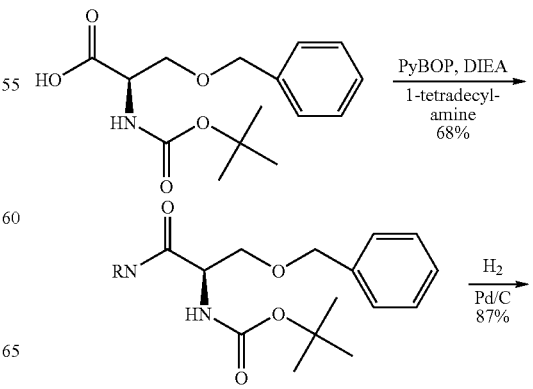

Scheme 2

-continued

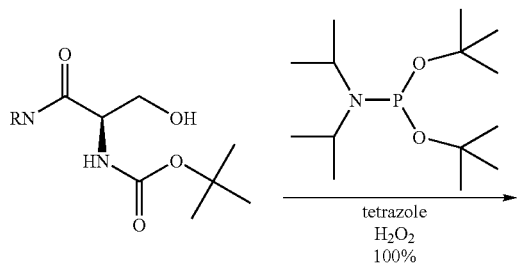

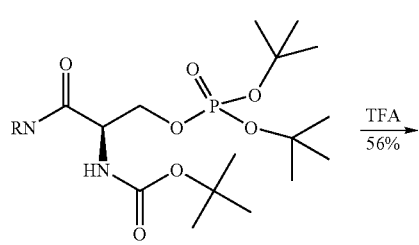

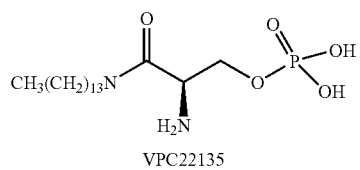

R = (CH2)13CH3

Coupling of long chain amine with protected serine. To a stirring solution of N-Boc-(D)-Serine-OBn (0.847 mmol) in CH$_2$Cl$_2$ (20 mL) was added PyBOP (0.847 mmol) followed by diisopropylethylamine (0.847 mmol). After 5 min. of stirring, 1-tetradecylamine (0.847 mmol) was added and stirring was continued for 1 h after which time more 1-tetradecylamine was added (0.254 mmol). Stirring was continued for another 3 h and then the reaction mixture was diluted with ethyl acetate (20 mL) and washed with sodium bicarbonate (3×15 mL), ammonium chloride (2×15 mL), and the organic layer was dried over sodium sulfate. Solvents were removed under reduced pressure to afford a clear gelatinous solid, which was purified by flash chromatography, using 95:5 CHCl$_3$/methanol, to afford the product (68%) as a white solid. R$_f$=0.78 (95:5 CHCl$_3$/methanol).

Benzyl deprotection of coupled product. To a solution of the coupled product (0.579 mmol) in 200 proof ethanol (15 mL) was added a catalytic amount of palladium on activated carbon. To the resulting solution was applied a positive pressure of hydrogen gas and the reaction mixture was stirred 12 h. The reaction mixture was then filtered through a plug of celite eluting with methanol and then the solvent was removed under reduced pressure to yield the product (87%) as a clear oil. R$_f$=0.5 (95:5 CHCl$_3$/methanol).

Phosphorylation of resulting alcohol. For phosphorylation, reaction is performed in the absence of light, work up and columns are completed with as little light as possible. To a solution of the alcohol (0.474 mmol) in 1:1 CH$_2$Cl$_2$/THF (20 mL) was added tetrazole (0.948 mmol) and the resulting mixture was stirred 30 min. Di-tert-butyl-di-isopropylphosphoramidite (0.948 mmol) was then added and the resulting reaction mixture was stirred 15 h. Hydrogen peroxide (1.896 mmol) was then added and the resulting mixture was then stirred 24 h, cooled to 0° C., and quenched by addition of aqueous Na$_2$S$_2$O$_5$. The resulting solution was diluted with ethyl acetate (50 mL) and washed with sodium bicarbonate (2×15 mL), water (1×15 mL), and finally brine (1×15 mL). The organic layer was dried over sodium sulfate and the solvent was removed under reduced pressure to afford a clear oil. Flash chromatography, using 90:10 CHCl$_3$/acetone, provided the product (100%) as a clear oil. R$_f$=0.23 (90:10 CHCl$_3$/acetone).

Deprotection of N-Boc and phosphate groups. To a stirred solution of the protected product (0.071 mmol) in CH$_2$Cl$_2$ (1 mL) was added trifluoroacetic acid (12.98 mmol) and stirring was continued 4 h. Under reduced pressure, solvent and excess trifluoroacetic acid were removed affording a brown oil. Rinsed oil with ether and removed under vacuum 5 times to afford the product (56%) as a white solid. R$_f$=0 (90:10 CHCl$_3$/methanol).

Synthesis of (2R) S1P Analog VPC22157, 173, 199, and 211

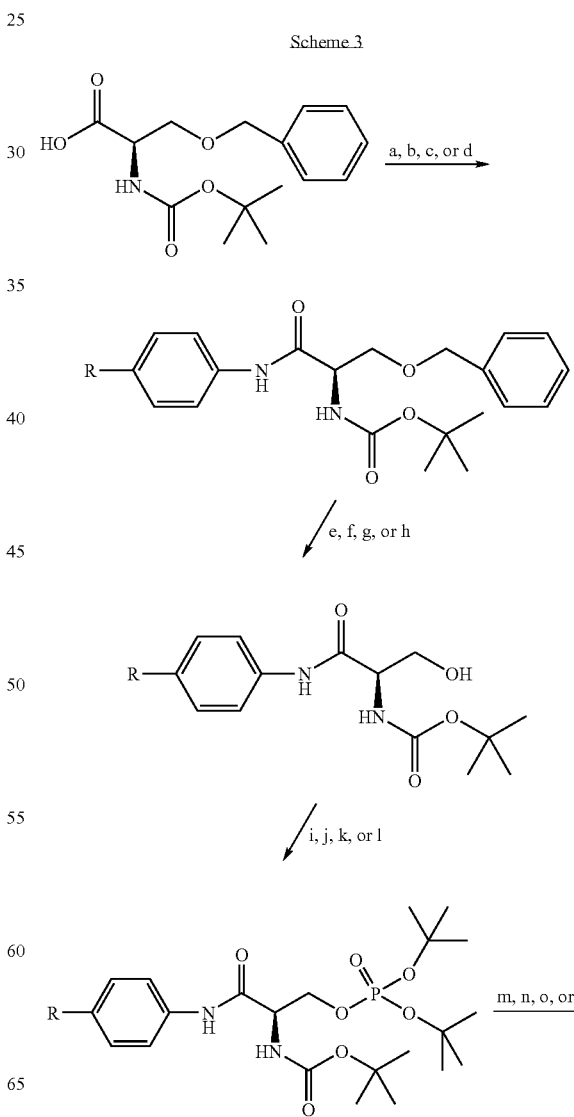

-continued

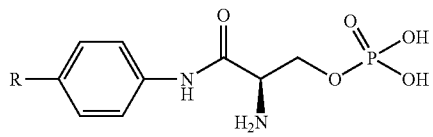

VPC22157: R=(CH$_2$)$_5$CH$_3$ (a, e, i, m)
VPC22173: R=(CH$_2$)$_7$CH$_3$ (b, f, j, n)
VPC22199: R=(CH$_2$)$_9$CH$_3$ (c, g, k, o)
VPC22211: R=(CH$_2$)$_{11}$CH$_3$ (d, h, l, p)

a) PyBOP, DIEA, 4-hexylaniline, 77%
b) PyBOP, DIEA, 4-octylaniline, 73%
c) PyBOP, DIEA, 4-decylaniline, 65%
d) PyBOP, DIEA, 4-dodecylaniline, 71%
e) Di$^t$Bu-di$^i$Pr-phosphoramidite, tetrazole, H$_2$O$_2$, 85%
f) Di$^t$Bu-di$^i$Pr-phosphoramidite, tetrazole, H$_2$O$_2$, 60%
g) Di$^t$Bu-di$^i$Pr-phosphoramidite, tetrazole, H$_2$O$_2$, 70%
h) Di$^t$Bu-di$^i$Pr-phosphoramidite, tetrazole, H$_2$O$_2$, 9%
i) H$_2$, Pd/C, 84%
j) H$_2$, Pd/C, 96%
k) H$_2$, Pd/C, 87%
l) H$_2$, Pd/C, 90%
m) TFA, 100%
n) TFA, 58%
o) TFA, 75%
p) TFA, 100%

Coupling of long chain aniline with protected serine. To a stirring solution of N-Boc-(D)-Serine-OBn (0.339 mmol) in CH$_2$Cl$_2$ (10 mL) was added PyBOP (0.339 mmol) followed by diisopropylethylamine (0.339 mmol). After 5 min. of stirring, the aniline (0.339 mmol) was added and stirring was continued for 4 h. The reaction mixture was then diluted with ethyl acetate (10 mL) and washed with sodium bicarbonate (3×10 mL), ammonium chloride (2×10 mL), and the organic layer was dried over sodium sulfate. Solvents were removed under reduced pressure to afford a clear gelatinous solid, which was purified by flash chromatography to afford the product.

VPC22157: 77%, white solid, R$_f$=0.80 (90:10 CHCl$_3$/acetone).
VPC22173: 73%, white solid, R$_f$=0.78 (90:10 CHCl$_3$/acetone).
VPC22199: 65%, white solid, R$_f$=0.79 (90:10 CHCl$_3$/acetone).
VPC22211: 71%, white solid, R$_f$=0.80 (90:10 CHCl$_3$/acetone).

Benzyl deprotection of coupled product. To a solution of the coupled product (0.260 mmol) in 200 proof ethanol (10 mL) was added a catalytic amount of palladium on activated carbon. To the resulting solution was applied a positive pressure of hydrogen gas and the reaction mixture was stirred 12 h. The reaction mixture was then filtered through a plug of celite eluting with methanol and then the solvent was removed under reduced pressure to yield the product.

VPC22157: 85%, clear oil, R$_f$=0.50 (95:5 CHCl$_3$/methanol).
VPC22173: 60%, clear oil, R$_f$=0.55 (95:5 CHCl$_3$/methanol).
VPC22199: 70%, clear oil, R$_f$=0.48 (95:5 CHCl$_3$/methanol).
VPC22211: 9%, clear oil, R$_f$=0.53 (95:5 CHCl$_3$/methanol).

Phosphorylation of resulting alcohol. For phosphorylation, reaction is performed in the absence of light, work up and columns are completed with as little light as possible. To a solution of the alcohol (0.220 mmol) in 1:1 CH$_2$Cl$_2$/THF (10 mL) was added tetrazole (0.400 mmol) and the resulting mixture was stirred 30 min. Di-tert-butyl-di-isopropylphosphoramidite (0.400 mmol) was then added and the resulting reaction mixture was stirred 15 h. Hydrogen peroxide (0.800 mmol) was then added and the resulting mixture was then stirred 24 h, cooled to 0° C., and quenched by addition of aqueous Na$_2$S$_2$O$_5$. The resulting solution was diluted with ethyl acetate (25 mL) and washed with sodium bicarbonate (2×10 mL), water (1×10 mL), and finally brine (1×10 mL). The organic layer was dried over sodium sulfate and the solvent was removed under reduced pressure to afford a clear oil. Flash chromatography provided the product as a clear oil.

VPC22157: 84%, clear oil, R$_f$=0.23 (90:10 CHCl$_3$/acetone).
VPC22173: 96%, clear oil, R$_f$=0.30 (90:10 CHCl$_3$/acetone).
VPC22199: 87%, clear oil, R$_f$=0.72 (80:20 CHCl$_3$/acetone).
VPC22211: 90%, clear oil, R$_f$=0.58 (80:20 CHCl$_3$/acetone).

Deprotection of N-Boc and phosphate groups. To a stirred solution of the protected product (0.162 mmol) in CH$_2$Cl$_2$ (2 mL) was added trifluoroacetic acid (25.96 mmol) and stirring was continued 4 h. Under reduced pressure, solvent and excess trifluoroacetic acid were removed affording a brown oil. Rinsed oil with ether and removed under vacuum 5 times to afford the product.

VPC22157: 100%, white solid, R$_f$=0 (90:10 CHCl$_3$/methanol).
VPC22173: 58%, white solid, R$_f$=0 (90:10 CHCl$_3$/methanol).
VPC22199: 75%, white solid, R$_f$=0 (90:10 CHCl$_3$/methanol).
VPC22211: 100%, white solid, R$_f$=0 (90:10 CHCl$_3$/methanol).

Synthesis of (2S) S1P Analogs VPC22179 and 181

Scheme 4

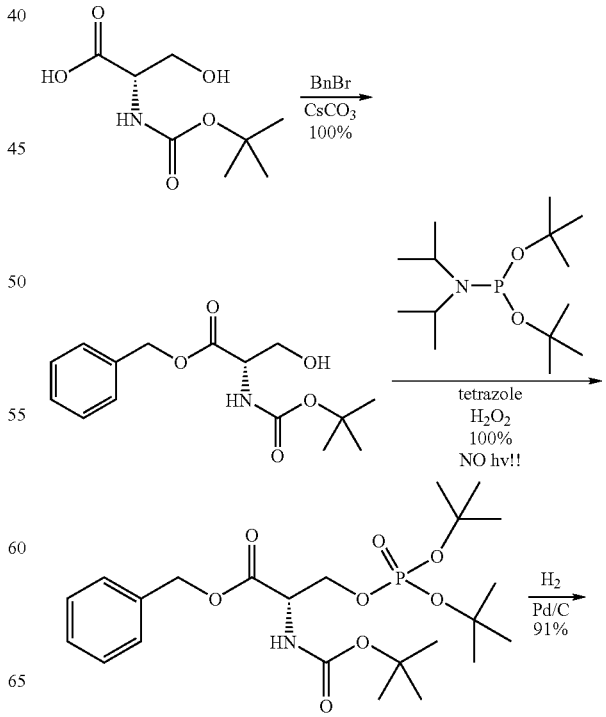

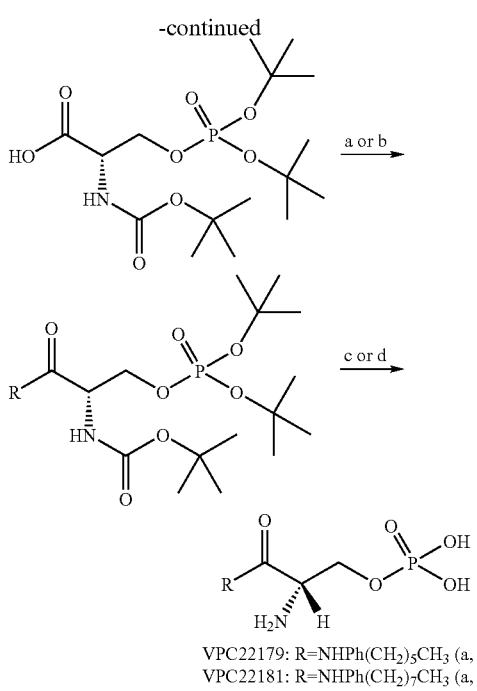

a) PyBOP, DIEA, 4-hexylaniline, 43%
b) PyBOP, DIEA, 4-octylaniline, 60%
c) TFA, 100%
d) TFA, 100%

Benzyl protection of N-Boc serine. To a stirring solution of N-Boc-(L)-Serine (2.44 mmol) in DMF (50 mL) was added cesium carbonate (2.56 mmol) and stirring was continued 30 min. Benzyl bromide (2.92 mmol) was then added and the resulting solution was stirred 12 h. The reaction mixture was then diluted with ethyl acetate (15 mL), washed with lithium bromide (3×10 mL), sodium bicarbonate (2×10 mL), and brine (2×10 mL). The organic layer was dried over sodium sulfate. The solvent was then removed under reduced pressure and the resulting tan oil was purified by flash chromatography, using 1:1 petroleum ether/diethyl ether, to afford the product (100%) as a white solid. $R_f$=0.26 (1:1 petroleum ether/diethyl ether).

Phosphorylation of resulting alcohol. For phosphorylation, reaction is performed in the absence of light, work up and columns are completed with as little light as possible. To a solution of the benzyl protected serine (2.22 mmol) in 1:1 CH$_2$Cl$_2$/THF (100 mL) was added tetrazole (4.43 mmol) and the resulting mixture was stirred 30 min. Di-tert-butyl-diisopropylphosphoramidite (4.43 mmol) was then added and the resulting reaction mixture was stirred 15 h. Hydrogen peroxide (8.86 mmol) was then added and the resulting mixture was stirred 3 h, cooled to 01 C, and quenched by addition of aqueous Na$_2$S$_2$O$_5$. The resulting solution was diluted with ethyl acetate (100 mL) and extracted with 50% aqueous Na$_2$S$_2$O$_5$ (2×20 mL). The organic layer was dried over sodium sulfate and the solvent was removed under reduced pressure to afford a tan oil. Flash chromatography, using 90:10 CHCl$_3$/acetone, provided the product (97%) as a clear oil. $R_f$=0.67 (90:10 CHCl$_3$/acetone).

Debenzylation of phosphorylated serine. To a solution of the phosphorylated serine (1.55 mmol) in 200 proof ethanol (25 mL) was added a catalytic amount of palladium on activated carbon. To the resulting solution was applied a positive pressure of hydrogen gas and the reaction mixture was stirred 12 h. The reaction mixture was then filtered through a plug of celite eluting with methanol and the solvent was removed under reduced pressure to yield the product (91%) as a slightly yellow oil. $R_f$=0 (90:10 CHCl$_3$/methanol).

Coupling of long chain aniline with phosphorylated acid. To a stirring solution of the phosphorylated acid (0.252 mmol) in CH$_2$Cl$_2$ (10 mL) was added PyBOP (0.252 mmol) followed by diisopropylethylamine (0.252 mmol). After 5 min. of stirring, the aniline (0.252 mmol) was added and stirring was continued for 4 h. The reaction mixture was then diluted with ethyl acetate (10 mL) and washed with sodium bicarbonate (3×10 mL), ammonium chloride (2×10 mL), and the organic layer was dried over sodium sulfate. Solvents were removed under reduced pressure to afford the product.

VPC22179: 43%, white solid, $R_f$=0.40 (90:10 CHCl$_3$/acetone).
VPC22181: 60%, white solid, $R_f$=0.35 (90:10 CHCl$_3$/acetone).

Deprotection of N-Boc and phosphate groups. To a stirred solution of the protected final product (0.117 mmol) in CH$_2$Cl$_2$ (1.5 mL) was added trifluoroacetic acid (19.48 mmol) and stirring was continued 4 h. Under reduced pressure, solvent and excess trifluoroacetic acid were removed affording a brown oil. The oil was rinsed with ether and the solvent was removed under vacuum 5 times to afford the product.

VPC22179: 100%, white solid, $R_f$=0 (90:10 CHCl$_3$/methanol).
VPC22181: 100%, white solid, $R_f$=0 (90:10 CHCl$_3$/methanol).

Synthesis of (2R) S1P Analog VPC22277

Scheme 5

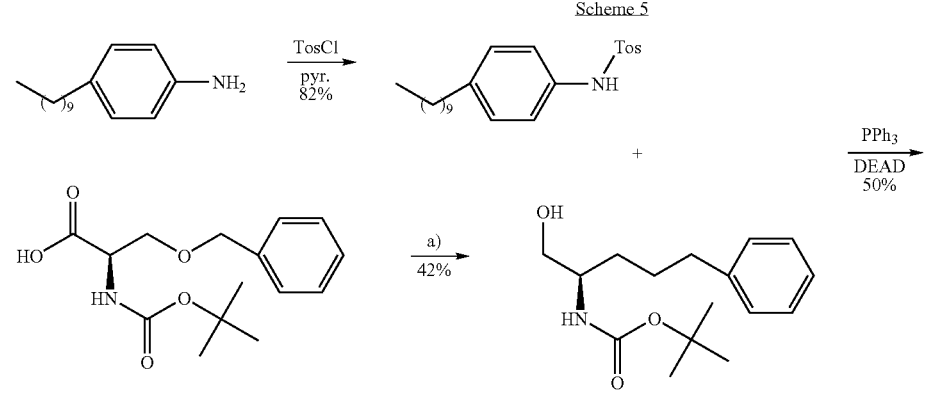

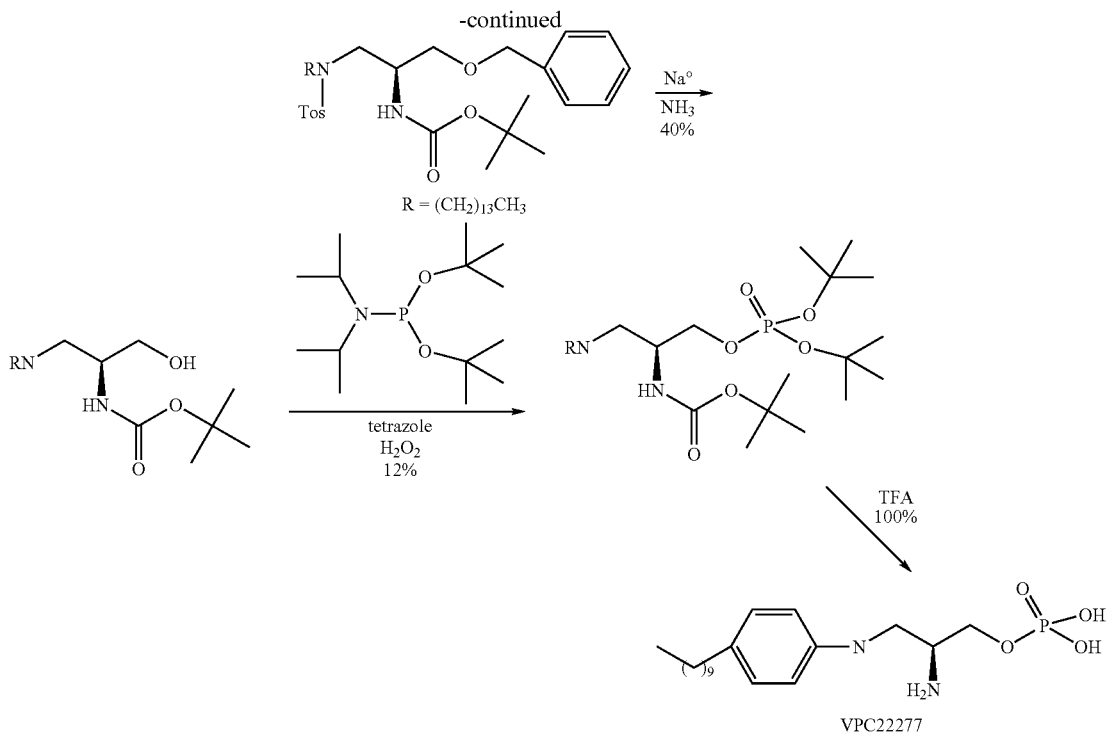

a): 1.) DIEA, isobutylchloroformate
2.) NaBH₄, H₂O, -10° C. ⟶ rt

Tosyl protection of the long chain aniline. To a stirring solution of the 4-decylaniline (0.428 mmol) in pyridine (3 mL) under inert atmosphere at 0° C. was added tosyl chloride (0.428 mmol). The reaction mixture was warmed to r.t. After 20 min., the reaction mixture was diluted with water (10 mL) and ethyl acetate (10 mL). The aqueous layer was discarded and the organic layer washed with 1N HCl (3×10 mL), sat. sodium bicarbonate (3×10 mL) and brine (2×10 mL). The organic layer was dried over sodium sulfate and the solvent was removed under reduced pressure to yield the product (81%) as pink crystals, which needed no further purification. $R_f$=0.82 (90:10 CHCl₃/acetone).

Reduction of protected amino acid. At −10° C., under inert atmosphere, N-Boc-(D)-Ser-OBz (0.678 mmol) and diisopropylethylamine (0.678 mmol) were added to stirring THF (3 mL). Isobutylchloroformate (0.745 mmol) was then slowly added. The reaction mixture was allowed to stir for 1 h until a precipitate was observed. The reaction mixture was then filtered and the filtrate was re-cooled to −10° C. Meanwhile, sodium borohydride (1.36 mmol) was dissolved in stirring water (0.5 mL) under inert atmosphere and this mixture was cooled to −10° C. The original reaction mixture was then cannulated into the sodium borohydride mixture slowly and the newly formed reaction mixture was brought to r.t. and stirred 1 h. The reaction mixture was then quenched by addition of sat. ammonium chloride (5 mL), diluted with ethyl acetate (15 mL) and the aqueous layer was discarded. The organic layer was then washed with sat. ammonium chloride (3×10 mL), sat. sodium bicarbonate (3×10 mL) and finally brine (1×10 mL). The organic layer was dried over sodium sulfate and the solvent was removed under reduced pressure to yield the crude product as a white solid. The crude product was purified by flash chromatography, using 80:20 CHCl₃/acetone, to afford the product (42%) as a white solid. $R_f$=0.48 (80:20 CHCl₃/acetone).

Coupling of aniline with alcohol. To a stirring solution of the aniline (0.209 mmol) in THF (3 mL) under an inert atmosphere was added triphenylphospine (0.254 mmol), the alcohol (0.105 mmol), and finally DEAD (0.209 mmol). The reaction mixture was stirred 12 h and then concentrated to a clear oil. Petroleum ether was added to the clear oil and solid triphenylphosphine oxide was allowed to settle on the bottom of the flask. The clear petroleum ether layer was then pipetted off and concentrated to a clear oil. The crude product was then subjected to flash chromatography, using 1:1 petroleum ether/ether, to afford the final product (50%) as a white solid. $R_f$=0.83 (1:1 petroleum ether/ether).

Tosyl deprotection of the coupled product. Ammonia (20 mL) was condensed in a 2-neck round bottom flask equipped with a stirbar and cold finger that was cooled to −70° C. under an inert atmosphere. Sodium metal (4.27 mmol) was then added to the reaction mixture followed by the tosyl protected amine (0.427 mmol) in THF (8 mL). The dark blue reaction mixture was stirred for 1 h at −70° C. and was then quenched with ethanol until the solution was clear/white and the reaction mixture was then stirred at r.t. overnight. The reaction mixture was then diluted with ethyl acetate (20 mL) and washed with sat. ammonium chloride (3×20 mL), sat. sodium bicarbonate (3×20 mL), and finally brine (1×20 mL). The organic layer was dried over sodium sulfate and the solvent was removed under reduced pressure to yield the crude product as a clear oil. The crude product was purified by flash chromatography, using 1:1 ethyl acetate/hexanes, to afford the product (40%) as a white solid. $R_f$=0.42 (1:1 ethyl acetate/hexanes).

Phosphorylation of resulting alcohol. For phosphorylation, reaction is performed in the absence of light, work up and columns are completed with as little light as possible. To a solution of the alcohol (0.130 mmol) in 1:1 CH$_2$Cl$_2$/THF (5 mL) was added tetrazole (0.130 mmol) and the resulting mixture was stirred 30 min. Di-tert-butyl-di-isopropylphosphoramidite (0.130 mmol) was then added and the resulting reaction mixture was stirred 15 h. Hydrogen peroxide (30%, 0.044 mL) was then added and the resulting mixture was then stirred 24 h, cooled to 0° C., and quenched by addition of aqueous Na$_2$S$_2$O$_5$. The resulting solution was diluted with ethyl acetate (10 mL) and washed with sodium bicarbonate (2×10 mL), water (1×10 mL), and finally brine (1×10 mL). The organic layer was dried over sodium sulfate and the solvent was removed under reduced pressure to afford a clear oil. Flash chromatography, using 1:1 ethyl acetate/hexanes, provided the product (12%) as a clear oil. R$_f$=0.41 (1:1 ethyl acetate/hexanes).

Deprotection of N-Boc and phosphate groups. To a stirred solution of the protected final product (0.016 mmol) in CH$_2$Cl$_2$ (0.5 mL) was added trifluoroacetic acid (6.49 mmol) and stirring was continued 4 h. Under reduced pressure, solvent and excess trifluoroacetic acid was removed affording a brown oil. The oil was rinsed with ether and the solvent was removed under vacuum 5 times to afford the product (100%) as a white solid. R$_f$=0 (90:10 CHCl$_3$/methanol).

Synthesis of (2R) S1P Analog VPC23031, 19, 65, 69, 75 and 79

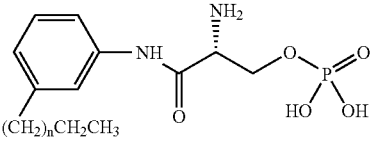

VPC23031
VPC23069
VPC23079

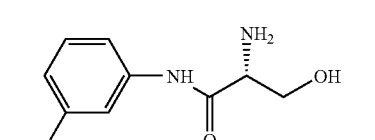

VPC23019
VPC23065
VPC23075

| Compound(s) | n | % Yields | | | | | | |
|---|---|---|---|---|---|---|---|---|
| | | A | B | C | D | E | F | G |
| VPC23031 | 4 | 24 | 66 | 52 | 100 | X | 90 | 100 |
| VPC23019 | 6 | 100 | 85 | 90 | 95 | X | 56 | 92 |
| VPC23065, 69 | 8 | 34 | 84 | 84 | 89 | 100 | 89 | 86 |
| VPC23075, 79 | 7 | 66 | 100 | 100 | 27 | 93 | 77 | 100 |

Coupling of aryl halide with terminal alkyne. All starting materials were thoroughly flushed with nitrogen before the Scheme 6

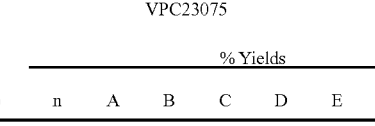

reaction. To a stirring solution of the aryl halide (2.01 mmol), bis(dibenzylideneacetone) palladium (0.04 mmol), triphenylphosphine (0.10 mmol), and copper iodide (0.04 mmol) in THF (10 mL) under inert atmosphere was added the terminal alkyne (2.21 mmol) followed by diisopropylethylamine (8.04 mmol). The reaction mixture was then stirred at r.t. for 12 h. The reaction mixture was then diluted with ethyl acetate (15 mL) and washed with sodium bicarbonate (3×15 mL), ammonium chloride (3×15 mL) and finally brine (1×15 mL). The organic layer was then dried over sodium sulfate. Solvents were removed under reduced pressure to afford a tan oil. Flash chromatography provided the final product.

VPC23031: 24%, yellow oil, $R_f$=0.61 (90:10 hexanes/ether).
VPC23019: 100%, yellow oil, $R_f$=0.55 (90:10 hexanes/ether).
VPC23065, 69: 66%, yellow oil, $R_f$=0.75 (90:10 hexanes/ether).
VPC23075, 79: 34%, yellow oil, $R_f$=0.75 (90:10 hexanes/ether).

Reduction of the coupled product. To a solution of the coupled product (1.68 mmol) in 200 proof ethanol (10 mL) was added a catalytic amount of palladium on activated carbon. To the resulting solution was applied a positive pressure of hydrogen gas and the reaction mixture was stirred 12 h. The reaction mixture was then filtered through a plug of celite eluting with methanol and then the solvent was removed under reduced pressure to yield the crude product.

VPC23031: 66%, yellow solid, $R_f$=0.53 (95:5 CHCl$_3$/acetone).
VPC23019: 85%, yellow solid, $R_f$=0.55 (95:5 CHCl$_3$/acetone).
VPC23065, 69: 84%, yellow solid, $R_f$=0.79 (95:5 CHCl$_3$/acetone).
VPC23075, 79: 100%, yellow solid, $R_f$=0.80 (95:5 CHCl$_3$/acetone).

Coupling of long chain aniline with protected serine. To a stirring solution of N-Boc-(D)-Serine-OBn (0.740 mmol) in CH$_2$Cl$_2$ (20 mL) was added PyBOP (0.740 mmol) followed by diisopropylethylamine (0.740 mmol). After 5 min. of stirring, the aniline (0.740 mmol) was added and stirring was continued for 4 hours. The reaction mixture was then diluted with ethyl acetate (20 mL) and washed with 1 N HCl (3×20 mL), sodium bicarbonate (3×20 mL), and finally brine (1×20 mL), and the organic layer was dried over sodium sulfate. Solvents were removed under reduced pressure to afford a clear oil, which was purified by flash chromatography to afford the product.

VPC23031: 52%, clear oil, $R_f$=0.35 (dichloromethane).
VPC23019: 90%, clear oil, $R_f$=0.61 (70:30 hexanes/ethyl acetate).
VPC23065, 69: 84%, clear oil, $R_f$=0.82 (90:10 CHCl$_3$/acetone).
VPC23075, 79: 100%, clear oil, $R_f$=0.92 (90:10 CHCl$_3$/acetone).

Benzyl deprotection of coupled product. To a solution of the coupled product (0.667 mmol) in 200 proof ethanol (15 mL) was added a catalytic amount of palladium on activated carbon. To the resulting solution was applied a positive pressure of hydrogen gas and the reaction mixture was stirred 12 h. The reaction mixture was then filtered through a plug of celite eluting with methanol and then the solvent was removed under reduced pressure to yield the product.

VPC23031: 100%, clear oil, $R_f$=0.27 (70:30 hexanes/ethyl acetate).
VPC23019: 95%, clear oil, $R_f$=0.28 (70:30 hexanes/ethyl acetate).
VPC23065, 69: 89%, clear oil, $R_f$=0.62 (1:1 hexanes/ethyl acetate).
VPC23075, 79: 27%, clear oil, $R_f$=0.43 (1:1 hexanes/ethyl acetate).

Deprotection to afford free alcohol. To a stirred solution of the N-Boc protected alcohol (0.143 mmol) in CH$_2$Cl$_2$ (2 mL) was added trifluoroacetic acid (25.96 mmol) and stirring was continued 4 h. Under reduced pressure, solvent and excess trifluoroacetic acid were removed affording a brown oil. The oil was rinsed with ether and the solvent was removed under vacuum 5 times to afford the product.

VPC23065: 100%, white solid, $R_f$=0.2 (90:10 CHCl$_3$/methanol).
VPC23075: 93%, white solid, $R_f$=0.2 (90:10 CHCl$_3$/methanol).

Phosphorylation of N-Boc protected alcohol. For phosphorylation, the reaction is performed in the absence of light, work up and columns are completed with as little light as possible. To a solution of the alcohol (0.247 mmol) in 1:1 CH$_2$Cl$_2$/THF (15 mL) was added tetrazole (0.495 mmol) and the resulting mixture was stirred 30 min. Di-tert-butyl-diisopropylphosphoramidite (0.495 mmol) was then added and the resulting reaction mixture was stirred 15 h. Hydrogen peroxide (0.989 mmol) was then added and the resulting mixture was then stirred 24 h, cooled to 0° C., and quenched by addition of aqueous Na$_2$S$_2$O$_5$. The resulting solution was diluted with ethyl acetate (25 mL) and washed with sodium bicarbonate (3×15 mL), ammonium chloride (3×15 mL), and finally brine (1×15 mL). The organic layer was dried over sodium sulfate and the solvent was removed under reduced pressure to afford a clear oil. Flash chromatography provided the product.

VPC23031: 90%, clear oil, $R_f$=0.80 (80:20 ether/ethyl acetate).
VPC23019: 56%, clear oil, $R_f$=0.82 (80:20 ether/ethyl acetate).
VPC23069: 89%, clear oil, $R_f$=0.85 (90:10 ether/ethyl acetate).
VPC23079: 77%, clear oil, $R_f$=0.85 (90:10 ether/ethyl acetate).

Deprotection of N-boc and phosphate groups. To a stirred solution of the protected product (0.162 mmol) in CH$_2$Cl$_2$ (2 mL) was added trifluoroacetic acid (25.96 mmol) and stirring was continued 4 h. Under reduced pressure, solvent and excess trifluoroacetic acid were removed affording a brown oil. Rinsed oil with ether and removed under vacuum 5 times to afford the product.

VPC23031: 100%, clear oil, $R_f$=0 (90:10 CHCl$_3$/methanol).
VPC23019: 92%, clear oil, $R_f$=0 (90:10 CHCl$_3$/methanol).
VPC23069: 86%, clear oil, $R_f$=0 (90:10 CHCl$_3$/methanol).
VPC23079: 100%, clear oil, $R_f$=0 (90:10 CHCl$_3$/methanol).

Synthesis of (2R)S1P Analog VPC23087 and 89:

Scheme 7

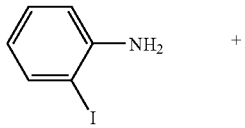

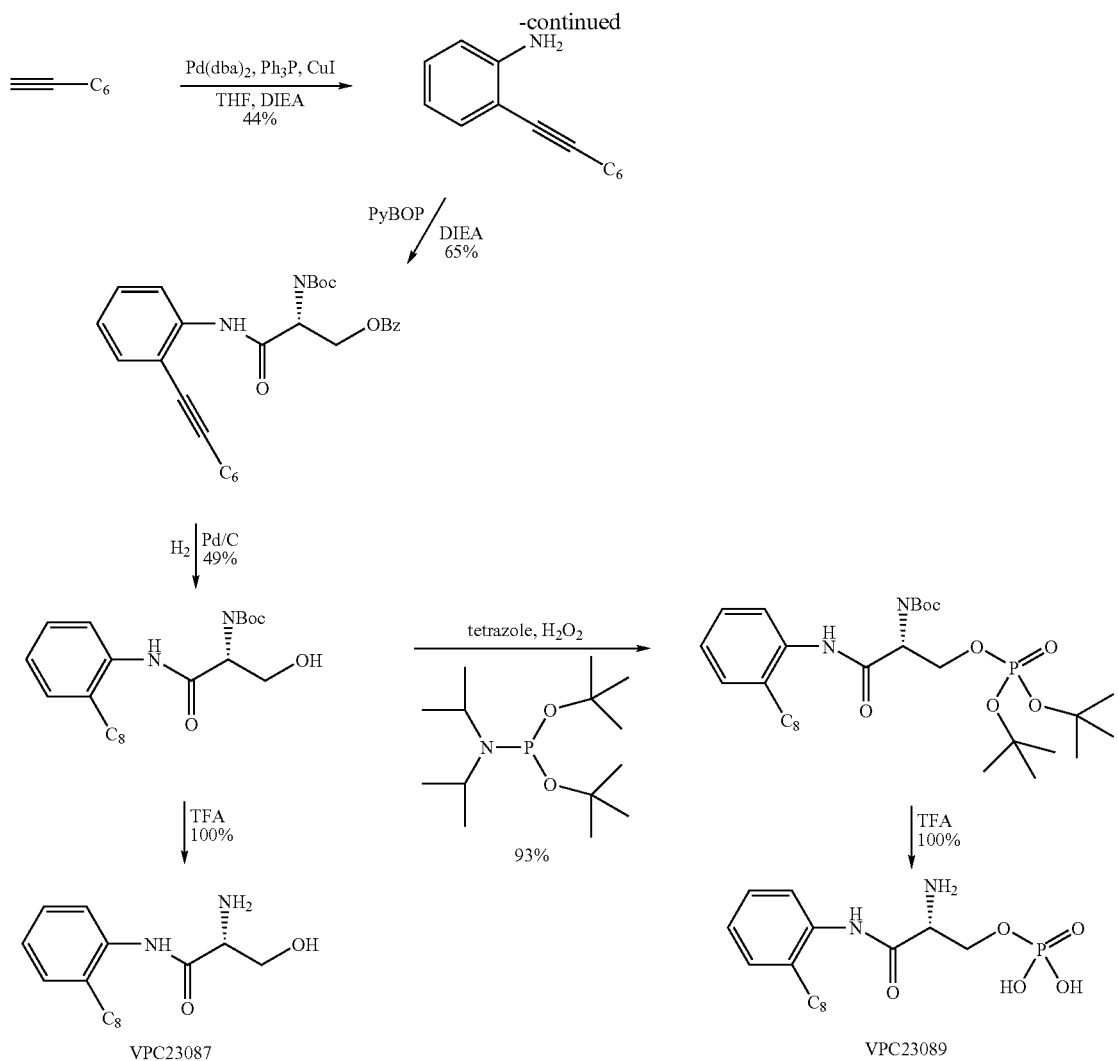

VPC23087

VPC23089

Coupling of aryl halide with terminal alkyne. All starting materials were thoroughly flushed with nitrogen before the reaction. To a stirring solution of the aryl halide (2.01 mmol), bis(dibenzylideneacetone) palladium (0.04 mmol), triphenylphosphine (0.10 mmol), and copper iodide (0.04 mmol) in THF (10 mL) under inert atmosphere was added the terminal alkyne (2.21 mmol) followed by diisopropylethylamine (8.04 mmol). The reaction mixture was then stirred at r.t. for 12 h. The reaction mixture was then diluted with ethyl acetate (15 mL) and washed with sodium bicarbonate (3×15 mL), ammonium chloride (3×15 mL) and finally brine (1×15 mL). The organic layer was then dried over sodium sulfate. Solvents were removed under reduced pressure to afford a tan oil. Flash chromatography, using 70:30 hexanes/ethyl acetate provided the final product (44%) as a yellow solid. $R_f$=0.79 (70:30 hexanes/ethyl acetate).

Coupling of long chain aniline with protected serine. To a stirring solution of N-boc-(D)-Serine-OBn (0.288 mmol) in $CH_2Cl_2$ (10 mL) was added PyBOP (0.288 mmol) followed by diisopropylethylamine (0.288 mmol). After 5 min. of stirring, the aniline (0.288 mmol) was added and stirring was continued for 4 hours. The reaction mixture was then diluted with ethyl acetate (10 mL) and washed with 1 N HCl (3×10 mL), sodium bicarbonate (3×10 mL), and finally brine (1×10 mL), and the organic layer was dried over sodium sulfate. Solvents were removed under reduced pressure to afford a clear oil. Flash chromatography, using 70:30 hexanes/ethyl acetate provided the final product (65%) as a clear oil. $R_f$=0.64 (70:30 hexanes/ethyl acetate).

Benzyl deprotection and reduction of coupled product. To a solution of the coupled product (0.188 mmol) in 200 proof ethanol (10 mL) was added a catalytic amount of palladium on activated carbon. To the resulting solution was applied a positive pressure of hydrogen gas and the reaction mixture was stirred 12 h. The reaction mixture was then filtered through a plug of celite eluting with methanol and then the solvent was removed under reduced pressure to yield the crude product as a clear oil. Flash chromatography, using 1:1 hexanes/ethyl acetate provided the final product (49%) as a clear oil. $R_f$=0.51 (1:1 hexanes/ethyl acetate).

Deprotection to afford free alcohol. To a stirred solution of the N-Boc protected alcohol (0.025 mmol) in $CH_2Cl_2$ (1 mL) was added trifluoroacetic acid (12.98 mmol) and stirring was continued 4 h. Under reduced pressure, solvent and excess trifluoroacetic acid were removed affording a brown oil. The oil was rinsed with ether and the solvent was removed under vacuum 5 times to afford the product (100%) as a white solid. $R_f$=0.2 (90:10 $CHCl_3$/methanol).

Phosphorylation of N-Boc protected alcohol. For phosphorylation, reaction is performed in the absence of light, work up and columns are completed with as little light as possible. To a solution of the alcohol (0.092 mmol) in 1:1 $CH_2Cl_2$/THF (10 mL) was added tetrazole (0.183 mmol) and the resulting mixture was stirred 30 min. Di-tert-butyl-di-isopropylphosphoramidite (0.183 mmol) was then added and the resulting reaction mixture was stirred 15 h. Hydrogen peroxide (0.367 mmol) was then added and the resulting mixture was then stirred 24 h, cooled to 0° C., and quenched by addition of aqueous $Na_2S_2O_5$. The resulting solution was diluted with ethyl acetate (15 mL) and washed with sodium bicarbonate (3×15 mL), ammonium chloride (3×15 mL), and finally brine (1×15 mL). The organic layer was dried over sodium sulfate and the solvent was removed under reduced pressure to afford a clear oil. Flash chromatography, using 90:10 ethyl acetate/ether provided the final product (93%) as a clear oil. $R_f$=0.85 (90:10 ethyl acetate/ether).

Deprotection of N-Boc and phosphate groups. To a stirred solution of the protected product (0.063 mmol) in $CH_2Cl_2$ (2 mL) was added trifluoroacetic acid (25.96 mmol) and stirring was continued 4 h. Under reduced pressure, solvent and excess trifluoroacetic acid were removed affording a brown oil. The oil was rinsed with ether and the solvent was removed under vacuum 5 times to afford the product (100%) as a white solid. $R_f$=0 (90:10 $CHCl_3$/methanol).

Synthesis of (2R) Benzimidazole Compound:

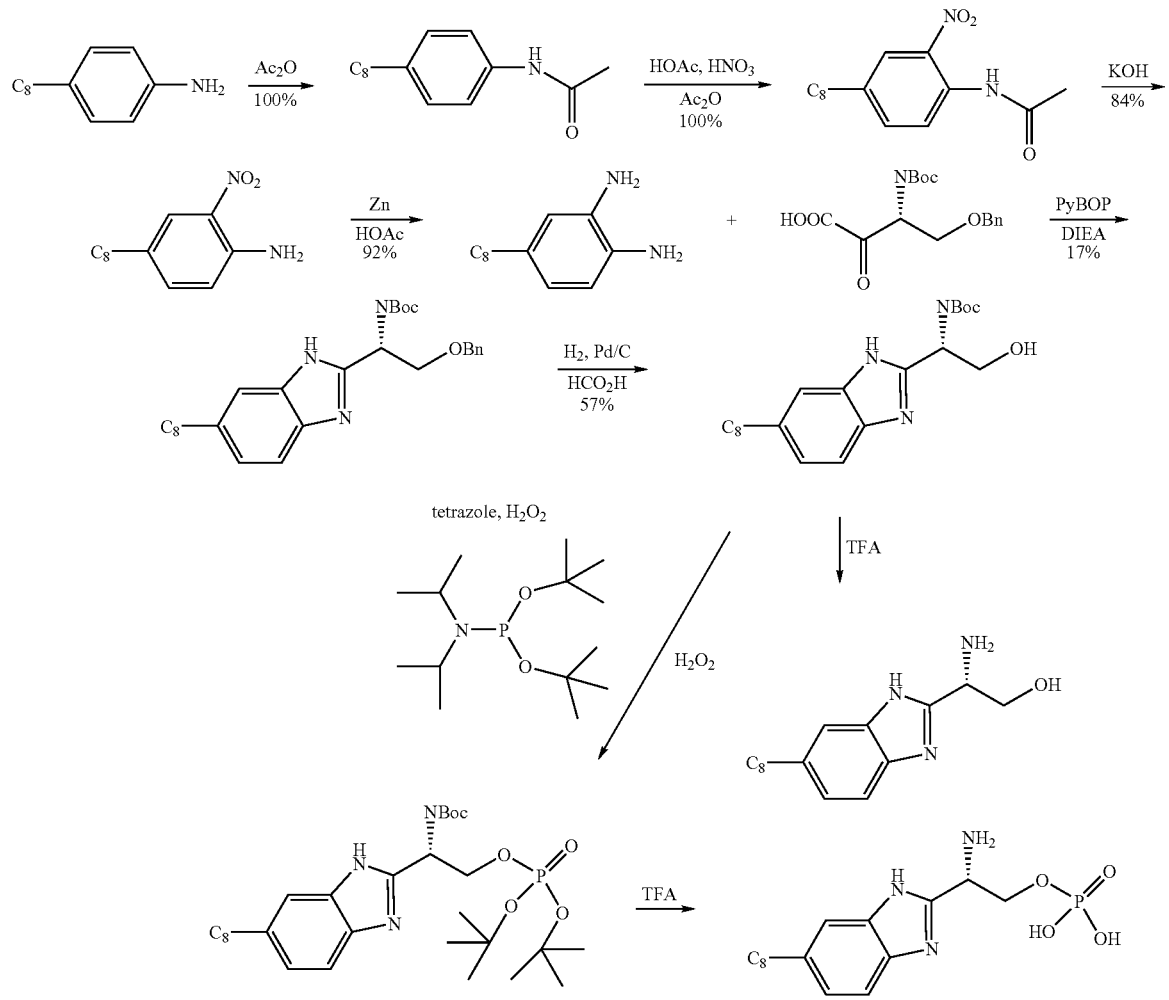

Scheme 8

Acetylation of the aniline. To a stirring solution of acetic anhydride (10 mL) under inert atmosphere was added octyl aniline (0.738 mmol) and stirring was continued for 1 h. Sat. aqueous sodium bicarbonate was then added to neutralize and acetic acid present. The aqueous solution was then extracted with ethyl acetate (3×15 mL) and the combined organic extracts were dried over sodium sulfate and concentrated to afford the final product (100%) as a yellow solid that was used without further purification. $R_f$=0.48 (90:10 $CHCl_3$/acetone).

Nitration of the acetylated aniline. To a stirring solution of acetic acid (1.08 mL), acetic anhydride (0.73 mL), and nitric acid (0.20 mL) at −15° C. under an inert atmosphere was added the acetylated aniline (0.91 mmol) in approx. 1 mL of acetic acid over a period of 3 h. Reaction mixture was periodically warmed to 0° C. to avoid freezing. The reaction mixture was stirred for an additional hour and was then diluted with ethyl acetate (10 mL) and neutralized using 1M NaOH and sat. aqueous sodium bicarbonate. The organic layer was removed and the aqueous portion washed twice more with ethyl acetate (10 mL each). The organic layers were combined and dried over sodium sulfate and then concentrated to a yellow solid. Flash chromatography, using 95:5 CHCl$_3$/acetone provided the final product (100%) as a yellow solid. $R_f$=0.68 (95:5 CHCl$_3$/acetone).

Deacetylation of the aniline. To a stirring solution of the nitrated, acetylated aniline (0.62 mmol) in ethanol (2.5 mL) under an inert atmosphere was added 40% KOH (0.13 mL). The reaction mixture was then heated to reflux for 1 h. The solution was then cooled in ice and brought to pH=6 using conc. HCl. This mixture was then concentrated to an orange solid and redissolved in ether (10 mL) and washed with sat. aqueous sodium bicarbonate (2×10 mL) and brine (1×10 mL). The organic layer was then dried over sodium sulfate and concentrated to afford the final product (84%) as an orange solid that was used without further purification. $R_f$=0.82 (95:5 CHCl$_3$/acetone).

Reduction of the nitro group. To a stirring solution of the nitrated aniline (0.248 mmol) in acetic acid (5 mL) was added a catalytic amount of zinc dust and stirring was continued overnight under an inert atmosphere. The reaction mixture was then diluted with ether and filtered through a plug of celite under and inert atmosphere using ether to elute. Care was taken not to expose the ether solution to air. The solution was then concentrated to afford the final product (92%) as a reddish-brown oil which was used directly in the next step without further purification. $R_f$=0.05 (95:5 CHCl$_3$/acetone).

Coupling of the diamine with protected serine. A solution of N-boc-(D)-Serine-OBn (0.999 mmol), PyBOP (0.999 mmol), diisopropylethylamine (0.999 mmol) in CH$_2$Cl$_2$ (25 mL) was stirred 5 min. under an inert atmosphere and then cannulated into a flask containing the diamine (0.999 mmol). This reaction mixture was then stirred 12 h. The reaction mixture was then diluted with ethyl acetate (30 mL) and washed with sat. aqueous sodium bicarbonate (3×3 mL), ammonium chloride (3×30 mL), and finally brine (1×30 mL), and the organic layer was dried over sodium sulfate. Solvents were removed under reduced pressure to afford a brown oil. Flash chromatography, using 90:10 CHCl$_3$/acetone provided the final product (17%) as a brown oil. $R_f$=0.52 (90:10 CHCl$_3$/acetone).

Benzyl deprotection of coupled product. To a solution of the coupled product (0.167 mmol) in 200 proof ethanol (10 mL) and a catalytic amount of formic acid was added a catalytic amount of palladium on activated carbon. To the resulting solution was applied a positive pressure of hydrogen gas and the reaction mixture was stirred 12 h. The reaction mixture was then filtered through a plug of celite eluting with methanol and then the solvent was removed under reduced pressure to yield the crude product as a tan oil. Prep. plate thin layer chromatography, using 90:10 CHCl$_3$/acetone provided the final product (57%) as a tan/white solid. $R_f$=0.08 (90:10 CHCl$_3$/acetone).

Deprotection to afford free alcohol. To a stirring solution of the N-Boc protected alcohol (0.008 mmol) in CH$_2$Cl$_2$ (0.5 mL) was added trifluoroacetic acid (0.5 mL) and stirring was continued 4 h. Under reduced pressure, solvent and excess trifluoroacetic acid were removed affording a brown oil. The oil was rinsed with ether and the solvent was removed under vacuum 5 times to afford the product (100%) as a tan solid. $R_f$=0.2 (90:10 CHCl$_3$/methanol).

Phosphorylation of N-Boc protected alcohol. For phosphorylation, reaction is performed in the absence of light, work up and columns are completed with as little light as possible. To a solution of the alcohol (0.085 mmol) in 1:1 CH$_2$Cl$_2$/THF (5 mL) was added tetrazole (0.170 mmol) and the resulting mixture was stirred 30 min. Di-tert-butyl-di-isopropylphosphoramidite (0.170 mmol) was then added and the resulting reaction mixture was stirred 15 h. Hydrogen peroxide (0.340 mmol) was then added and the resulting mixture was then stirred 4 h, cooled to 0° C., and quenched by addition of aqueous Na$_2$S$_2$O$_5$. The resulting solution was diluted with ethyl acetate (10 mL) and washed with sodium bicarbonate (3×10 mL), ammonium chloride (3×10 mL), and finally brine (1×10 mL). The organic layer was dried over sodium sulfate and the solvent was removed under reduced pressure to afford the product.

Deprotection of N-Boc and phosphate groups. To a stirring solution of the protected product in CH$_2$Cl$_2$ was added trifluoroacetic acid and stirring was continued 4 h. Under reduced pressure, solvent and excess trifluoroacetic acid were removed affording a brown oil. The oil was rinsed with ether and the solvent was removed under vacuum 5 times to afford the product.

EXAMPLE 2

All reactions for the synthetic schemes of Example 2 were accomplished using solvents purified by filtration through alumina (activity I) immediately prior to use. All reactions were performed under an inert atmosphere of nitrogen unless otherwise noted. All reagents were purchased from either Aldrich (Milwaukee, Wis.), Sigma (St. Louis, Mo.), Acros (Pittsburgh, Pa.), Advanced ChemTech (Louisville, Ky.), or Novabiochem (La Jolla, Calif.). Merck silica gel F-254 precoated, aluminum backed plates were used for thin layer chromatography (TLC) analysis. Analtech Silica Gel GF 500 or 1000 μm precoated, glass backed plates were used for preparative TLC. Silicycle Ultra Pure Silica Gel (230-400 mesh) or Fisher Scientific Silica Gel 60 Sorbent (230-400 mesh) was used for column chromatography. Each product was analyzed by TLC (single spot) and spectroscopic methods including $^1$H NMR, $^{13}$C NMR, and mass spectrometry. The nuclear magnetic resonance spectra were collected using a General Electric QE300 spectrometer at 300 MHz and chemical shifts are reported in ppm. The assigned structures of the S1P analogs were consistent with all spectral data obtained.

Synthesis of Imidiazole Analog

Scheme 9

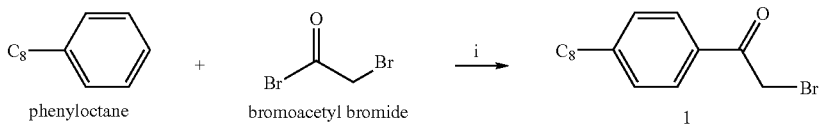

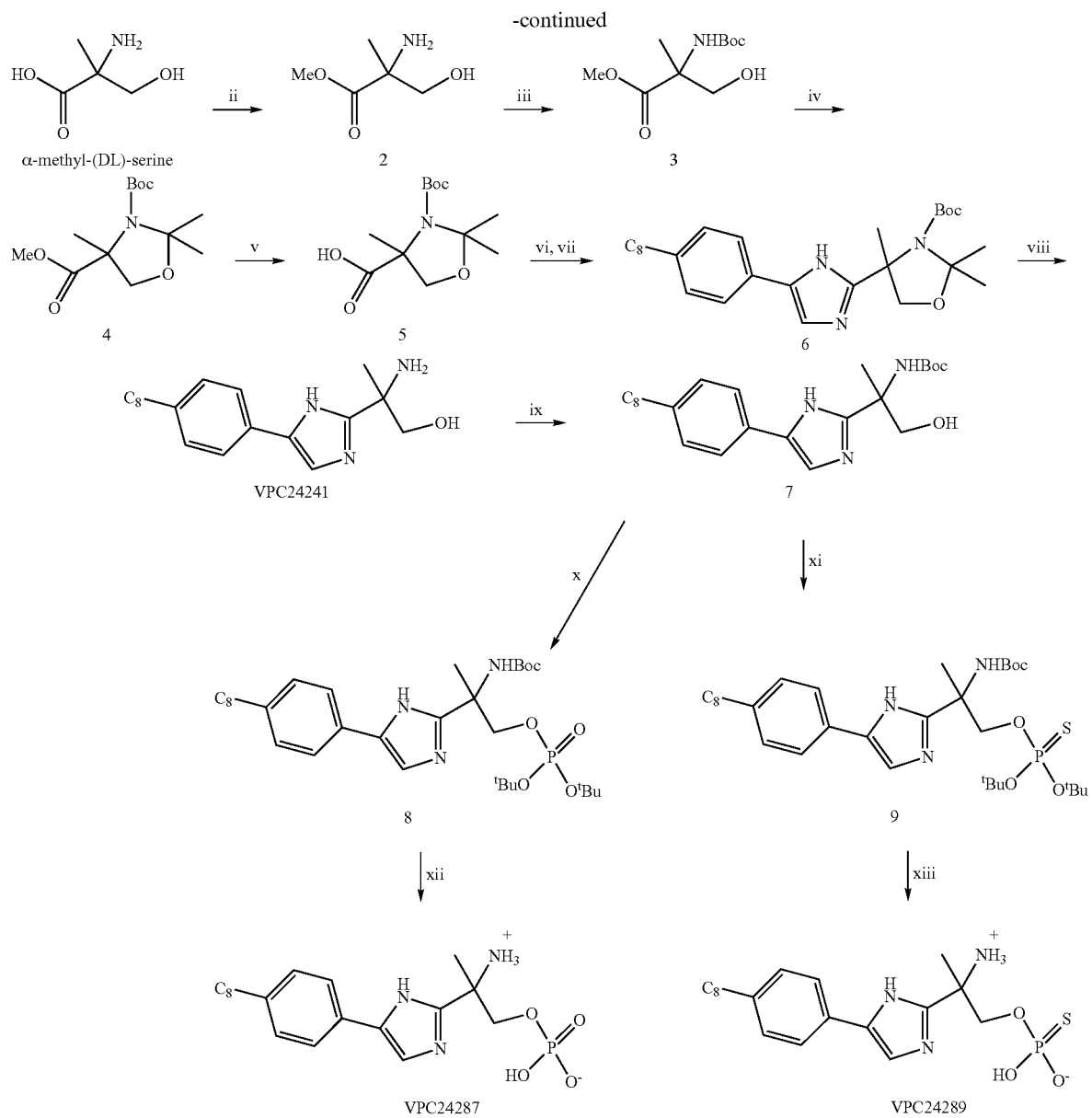

Reagents and Conditions: (i) NaH, THF 0° to R.T. 45 min., then Selectfluor 0° to R.T., overnight, 53%; (ii) SOCl$_2$, MeOH, R.T., 4-6 h.; (iii) Boc$_2$O, TEA, CH$_2$Cl$_2$, R.T., 4 h.; (iv) 2,2-dimethoxypropane, p-toluenesulfonic acid, CH$_2$Cl$_2$, R.T., 2 h., 62% (3 steps) (v) LiCl, NaBH$_4$, EtOH/THF (3:2), 0° to R.T., 4 h, 89%; (vi) PCC, CH$_2$Cl$_2$, R.T., 6 h.; (vii) DBU, LiCl, CH$_3$CN, R.T., overnight, 40% (2 steps); (viii) Dowex 50×8, EtOH, R.T. 24 h., 80%; (ix) PCC, CH$_2$Cl$_2$, R.T., 6 h. (x) NaClO$_2$, NaH$_2$PO$_4$.H$_2$O, t-butanol, 2-methyl-2-butene; (xi) p-octyl aniline, PyBOP, DIEA, CH$_2$Cl$_2$, R.T., overnight; (xii) H$_2$, 10% Pd/C, EtOH, R.T. overnight; (xiii) TMSBr, CH$_2$Cl$_2$, R.T., 4 h., then 95% CH$_3$OH in H$_2$O, R.T., 1 h.

2-Bromo-1-(4-octyl-phenyl)-ethanone (1). To a flame dried round bottom flask equipped with a magnetic stirbar under an inert atmosphere was added AlCl$_3$ (5.47 g; 41 mmol) followed by 1,2-dichloroethane (22 mL). The stirring suspension was then brought to 0° C. and 1-phenyloctane (7.99 mL, 36 mmol) was added in one portion. Bromoacetyl bromide (3.75 mL, 43 mmol) was then added dropwise over a period of 10 minutes. Upon completing addition of the acid bromide, the reaction mixture was brought to rt and stirred for 2 h. The reaction mixture was then quenched carefully by slow addition of H$_2$O (36 mL) without ever letting the reaction mixture exceed 45° C. producing a suspension of solid white precipitate. The aqueous layer of the quenched reaction mixture was discarded and the organic phase washed once with 10% HCl (10 mL), washed once with H$_2$O (10 mL), and dried over magnesium sulfate. The dried organic phase was then concentrated in vacuo to a green/brown oil. Recrystallization from MeOH/H$_2$O provided the product 1 (6.36 g, 57%) as white needles in three crops. R$_f$=0.21 (1:19 EtOAc/hexanes).

2-Amino-3-hydroxy-2-methyl-propionic acid methyl ester (2). A stirring solution of α-methyl-DL-Serine (1 g, 8.39 mmol) in MeOH (40 mL) in a flame dried round bottom flask under an inert atmosphere was cooled to 0° C. and SOCl$_2$ (1.84 mL, 25.19 mmol) was slowly added. After addition of the SOCl$_2$ was complete, the reaction mixture was stirred 12 h at rt and then concentrated in vacuo to a white solid that was used directly in the next reaction.

2-tert-Butoxycarbonylamino-3-hydroxy-2-methyl-propionic acid methyl ester (3). To the crude product obtained in the above reaction was slowly added sat. aq. NaHCO$_3$ (12.5 mL) followed by solid NaHCO$_3$ (500 mg) and the reaction mixture was stirred 30 min under an inert atmosphere. THF (12.5 mL) was then added to the reaction mixture followed by di-tert-butyl dicarbonate (1.83 g, 8.39 mmol) and stirring at rt was continued for 12 h. The reaction mixture was then diluted with H$_2$O (20 mL) and extracted with EtOAc (3×20 mL). The combined EtOAc extracts were dried over sodium sulfate and concentrated in vacuo to a thick white paste. To this paste was added hexanes which produced 3 (630 mg, 32% for 2 steps) as a white precipitate which was collected by filtration. R$_f$=0.35 (1:1 EtOAc/hexanes).

2,2,4-Trimethyl-oxazolidine-3,4-dicarboxylic acid 3-tert-butyl ester 4-methyl ester (4). To a stirring solution of 3 (9.342 g, 40 mmol) in acetone (115 mL) in a flame dried round bottom flask under an inert atmosphere was added 2,2-dimethoxypropane (66 mL). To this solution was added BF$_3$.OEt$_2$ (0.30 mL, cat.) and stirring was continued at rt for 2 h. The reaction mixture was then concentrated in vacuo to an orange oil which was purified by flash chromatography to provide 4 (9.392 g, 85%) as a white solid. R$_f$=0.55 (1:3 EtOAc/hexanes). Compound was observed as an uneven mixture of rotomers.

2,2,4-Trimethyl-oxazolidine-3,4-dicarboxylic acid 3-tert-butyl ester (5). To a stirring solution of 4 (9.392 g, 34 mmol) in THF (65 mL) and H$_2$O (35 mL) under an inert atmosphere was added solid LiOH.H$_2$O (1.426 g, 34 mmol) in one portion. The reaction mixture was heated to 90° C. and stirred 8 h at which point the reaction mixture was cooled to rt. The crude reaction mixture washed with Et$_2$O (3×50 mL) and the Et$_2$O extracts were discarded. The aqueous solution was then acidified with 2M KHSO$_4$ until a white precipitate began to form on addition, pH=5. The acid was added dropwise until the precipitate persisted and the aqueous solution was extracted with Et$_2$O (50 mL). After extraction, two addition drops of acid were added to the aqueous layer and it was again extracted with Et$_2$O (25 mL). The Et$_2$O extracts were combined and quickly back extracted with 1M NaOH (15 mL). The organic phase was then dried over sodium sulfate and concentrated in vacuo to give 5 (7.458 g, 85%) as a white solid which was used without further purification. Compound was observed as an uneven mixture of rotomers.

2,2,4-Trimethyl-4-[5-(4-octyl-phenyl)-1H-imidazol-2-yl]-oxazolidine-3-carboxylic acid tert-butyl ester (6). To a flame dried round bottom flask equipped with a magnetic stirbar under an inert atmosphere was added 5 (3.00 g, 11.6 mmol) followed by absolute EtOH (33 mL) and Cs$_2$CO$_3$ (1.93 g, 5.9 mmol). This mixture was then shaken 30 min at which time all of the suspended Cs$_2$CO$_3$ had disappeared. The reaction mixture was then concentrated in vacuo to a white solid at which time DMF (60 mL) was added. To the stirring solution was added a solution of 1 (3.60 g, 11.6 mmol) in DMF (5 mL). The resulting solution was stirred 4 h and concentrated to a light brown solid. To the light brown solid was added EtOAc (50 mL) and the suspended CsBr was filtered off and washed with EtOAc. The filtrate was then concentrated to a light brown foam which was subsequently dissolved in xylenes (195 mL) in a round bottom flask equipped with a Dean-Stark trap (filled with xylenes) and a reflux condenser. To this solution was added NH$_4$OAc (1.74 g, 22.6 mmol) and the reaction mixture was brought to 105° C. and stirred 3 h at which time the reaction would progress no further. The crude reaction mixture was then concentrated in vacuo to a red oil. To the oil was added EtOAc (200 mL) and this solution washed with sat. aq. NaHCO$_3$ (3×50 mL) followed by brine solution (1×50 mL). The organic phase was then dried over sodium sulfate and concentrated to a red oil which was subjected to flash chromatography to give 6 (1.074 g, 20%) as a white solid. R$_f$=0.45 (6:4 Et$_2$O/petroleum ether).

2-Amino-2-[5-(4-octyl-phenyl)-1H-imidazol-2-yl]-propan-1-ol (VPC24241). To a flame dried round bottom flask equipped with a magnetic stirbar under an inert atmosphere was added 6 (973 mg, 2.07 mmol) followed by MeOH (20 mL) and p-TsOH.H$_2$O (1.22 g, 6.42 mmol). This mixture was then heated to reflux, stirred 3 h, cooled to 0° C., and quenched by slow addition of sat. aq. NaHCO$_3$ (20 mL). This solution was then diluted with EtOAc (30 mL) and the aqueous layer was discarded. The organic phase washed with sat. aq. NaHCO$_3$ (1×20 mL), washed with 1M NaOH (1×20 mL), dried over sodium sulfate, and concentrated to an orange oil. To this oil was added Et$_2$O which produced VPC24241 (408 mg, 60%) as a white precipitate which was collected by filtration.

{2-Hydroxy-1-methyl-1-[5-(4-octyl-phenyl)-1H-imidazol-2-yl]-ethyl}-carbamic acid tert-butyl ester (7). To a vigorously stirring solution of VPC24241 (70 mg, 0.213 mmol) in THF (4 mL) and H$_2$O (2 mL) was added Na$_2$CO$_3$ (198 mg, 1.87 mmol) followed by di-tert-butyl dicarbonate (214 mg, 0.98 mmol) and the resulting solution was stirred 12 h at rt. The reaction mixture was then diluted with EtOAc (20 mL) and washed with saturated aq. NaHCO$_3$ (2×15 mL). The organic phase was dried over sodium sulfate and concentrated in vacuo to a clear oil which solidified to a white solid under vacuum. This white solid was then subjected to flash chromatography to produce 7 (52 mg, 57%) as a white solid. R$_f$=0.50 (1:1 EtOAc/hexanes).

{2-(Di-tert-butoxy-phosphoryloxy)-1-methyl-1-[5-(4-octyl-phenyl)-1H-imidazol-2-yl]-ethyl}-carbamic acid tert-butyl ester (8). To a solution of 7 (33 mg, 0.077 mmol) in 1:1 CH$_2$Cl$_2$/THF (3 mL) was added a 3% solution of tetrazole in acetonitrile (0.44 mL, 0.154 mmol) and the resulting mixture was stirred 30 min. Di-tert-butyl-di-isopropylphosphoramidite (0.05 mL, 0.154 mmol) was then added and the resulting reaction mixture was stirred 12 h. To this solution was added 30% hydrogen peroxide (0.04 mL, 0.308 mmol) and the resulting mixture was stirred 3 h, cooled to 0° C., and quenched by addition of aqueous Na$_2$S$_2$O$_5$. The resulting solution was diluted with ethyl acetate (10 mL) and washed with saturated aq. NaHCO$_3$ (2×5 mL). The organic layer was dried over sodium sulfate and the solvent was removed under reduced pressure to afford a clear oil. Flash chromatography, using 1:1 EtOAc/hexanes, provided 8 (22 mg, 46%) as a clear oil. R$_f$=0.45 (1:1 EtOAc/hexanes).

{2-(Di-tert-butoxy-thiophosphoryloxy)-1-methyl-1-[5-(4-octyl-phenyl)-1H-imidazol-2-yl]-ethyl}-carbamic acid tert-butyl ester (9). To a solution of 7 (19 mg, 0.044 mmol) in 1:1 CH$_2$Cl$_2$/THF (2 mL) was added a 3% solution of tetrazole in acetonitrile (0.26 mL, 0.089 mmol) and the resulting mixture was stirred 30 min. Di-tert-butyl-di-isopropylphosphoramidite (0.03 mL, 0.089 mmol) was then added and the resulting reaction mixture was stirred 12 h. To this solution was added elemental sulfur (excess) and the resulting mixture was stirred 12 h. The resulting solution was diluted with ethyl acetate (7 mL) and washed with saturated aq. NaHCO$_3$ (2×3 mL). The organic layer was dried over sodium sulfate and the solvent was removed under reduced pressure to afford a clear oil with yellow tint. Flash chromatography, using 1:3 EtOAc/hexanes, provided 9 (13 mg, 46%) as a clear oil. R$_f$=0.40 (1:3 EtOAc/hexanes).

Phosphoric acid mono-{2-amino-2-[5-(4-octyl-phenyl)-1H-imidazol-2-yl]-propyl}ester (VPC24287). To a stirring solution of 8 (22 mg, 0.035 mmol) in CH$_2$Cl$_2$ (1 mL) was added trifluoroacetic acid (1 mL) and stirring was continued 4 h. Solvent and excess trifluoroacetic acid were removed in vacuo to afford a brown oil. The oil was diluted with ether and concentrated in vacuo 5 times on a rotary evaporator to afford a white solid which was placed in a fritted funnel and washed with cold ether producing VPC24287 (13 mg, 91%) as a powdery white solid. R$_f$=0 (4:1 CHCl$_3$/methanol).

Thiophosphoric acid O-{2-amino-2-[5-(4-octyl-phenyl)-1H-imidazol-2-yl]-propyl}ester (VPC24289). To a stirring solution of 9 (13 mg, 0.020 mmol) in CH$_2$Cl$_2$ (1 mL) was added benzenethiol (0.042 mL, 0.40 mmol) followed by bromotrimethyl silane (0.05 mL, 0.40 mmol) and finally trifluoroacetic acid (1 mL) and stirring was continued 6 h. To quench the reaction mixture, water (0.5 mL) was added and the resulting solution was stirred 30 min. Solvent and excess reagents were removed in vacuo to afford a brown oil. The oil was diluted with ether and concentrated in vacuo 5 times on a rotary evaporator to afford a light tan solid which was placed in a fritted funnel and washed with cold ether and a small amount of cold water producing VPC24289 (8 mg, 94%) as a powdery white solid. R$_f$=0 (4:1 CHCl$_3$/metha.

Synthetic Scheme for Synthesis of Additional Imidizole Compounds

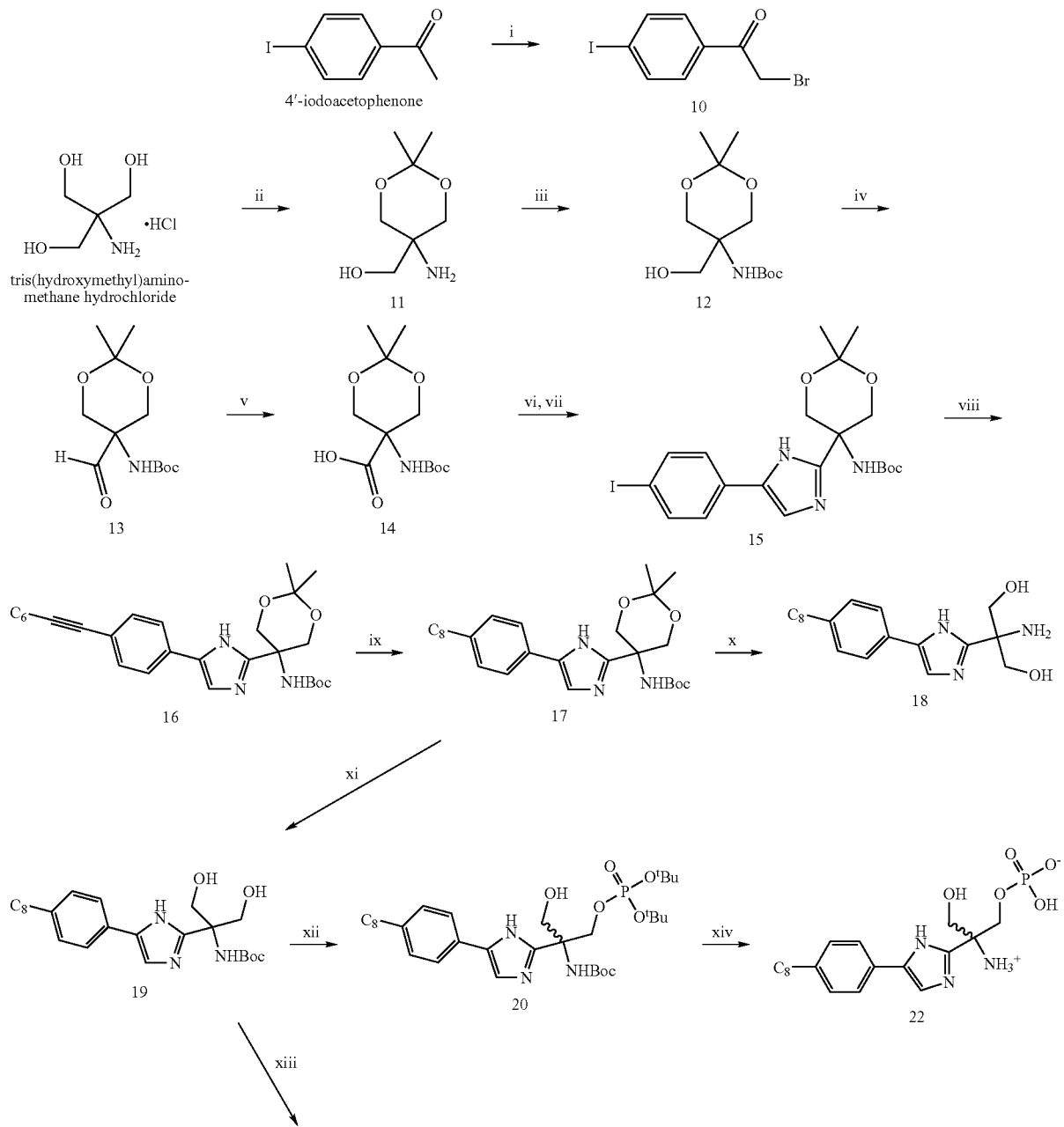

-continued

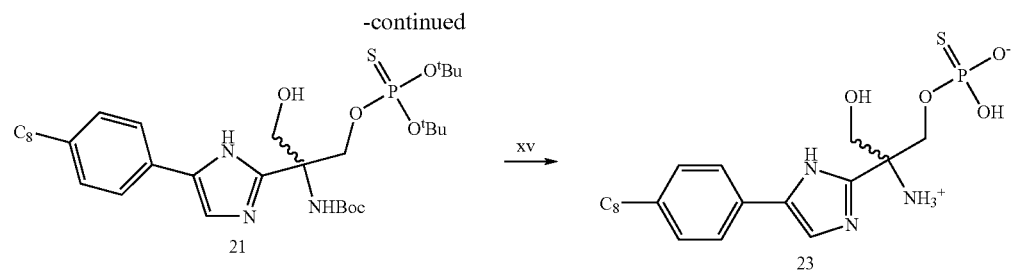

Reagents and Conditions: (i) Br$_2$, 1:1 dioxane/ether, CH$_2$Cl$_2$, rt, 1 h, 66%; (ii) 2,2-DMP, p-TsOH, DMF, rt, 12 h, TEA, rt, 10 min; (iii) (Boc)$_2$O, NaHCO$_3$, THF/H$_2$O, rt, 12 h, 69% (2 steps); (iv) (COCl)$_2$, DMSO, TEA, CH$_2$Cl$_2$, −78° C. to rt, 4 h, 74%; (v) NaClO$_2$, NaH$_2$PO$_4$·H$_2$O, 2-methyl-2-butene, $^t$BuOH/H$_2$O, rt, 1 h, 95%; (vi) Cs$_2$CO$_3$, EtOH, rt, 1 h; 1, DMF, rt, 12 h; (vii) NH$_4$OAc, xylenes, 110° C., 12 h, 36% (2 steps); (viii) Pd(dba)$_2$, Ph$_3$P, CuI, DIEA, THF, rt, 12 h, 68%; (ix) H$_2$, 10% Pd/C, EtOH, rt, 12 h; (x) 1:1 TFA/CH$_2$Cl$_2$, rt, 6 h; (xi) DOWEX 50×8, EtOH, rt, 12 h; (xii) tetrazole, di-tert-butyl diisopropylphosphoramidite, CH$_2$Cl$_2$/THF, rt, 12 h; H$_2$O$_2$, rt, 3 h; (xiii) tetrazole, di-tert-butyl diisopropylphosphoramidite, CH$_2$Cl$_2$/THF, rt, 12 h; S$_8$, rt, 3 h; (xiv) 1:1 TFA/CH$_2$Cl$_2$, rt, 4 h; (xv) benzenethiol, TMSBr, 1:1 TFA/CH$_2$Cl$_2$, rt, 4 h.

Synthetic Scheme for Synthesis of Alpha Substituted Phosphonate Compounds

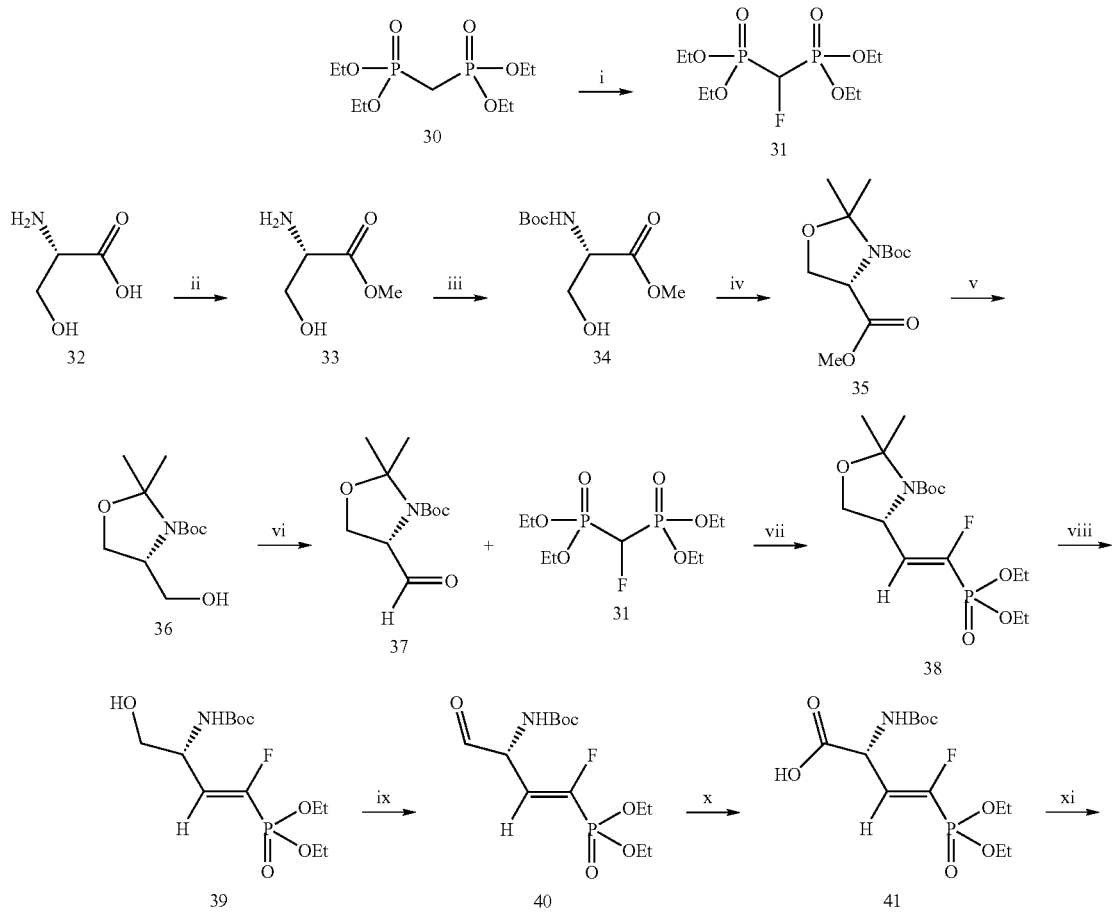

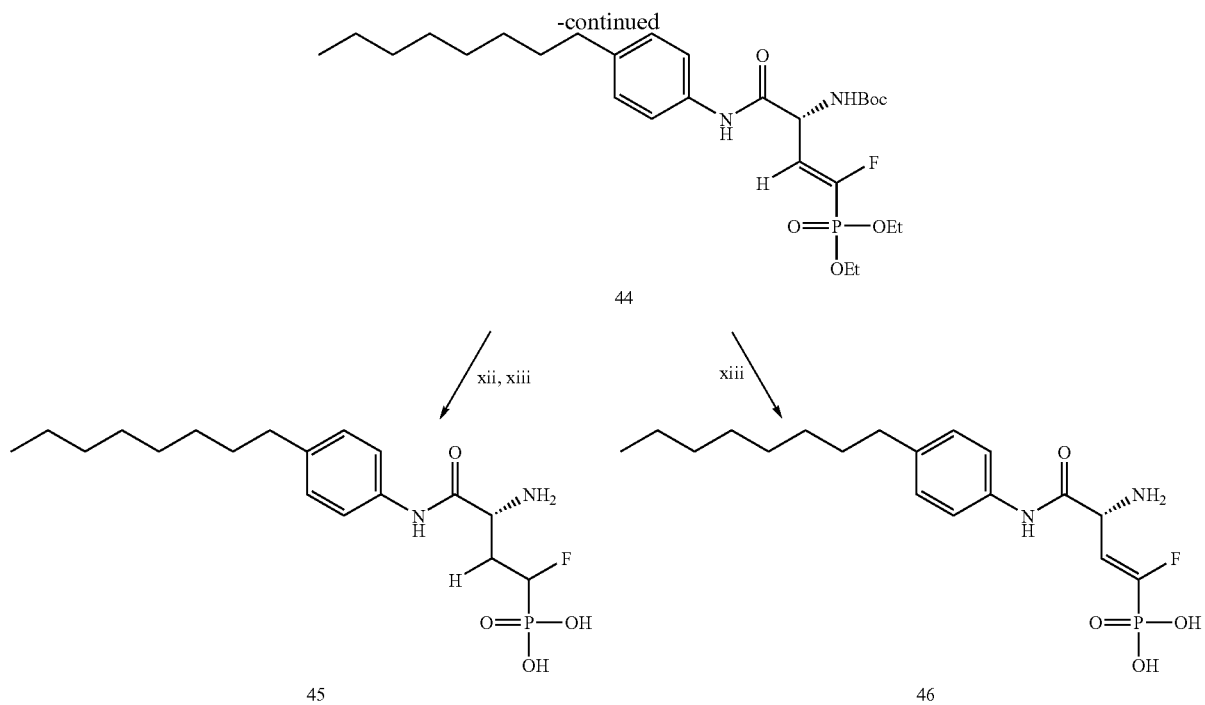

Reagents and Conditions: (i) NaH, THF 0° to R.T. 45 min., then Selectfluor 0° to R.T., overnight, 53%; (ii) SOCl$_2$, MeOH, R.T., 4-6 h.; (iii) Boc$_2$O, TEA, CH$_2$Cl$_2$, R.T., 4 h.; (iv) 2,2-dimethoxypropane, p-toluenesulfonic acid, CH$_2$Cl$_2$, R.T., 2 h., 62% (3 steps) (v) LiCl, NaBH$_4$, EtOH/THF (3:2), 0° to R.T., 4 h, 89%; (vi) PCC, CH$_2$Cl$_2$, R.T., 6 h.; (vii) DBU, LiCl, CH$_3$CN, R.T., overnight, 40% (2 steps); (viii) Dowex 50×8, EtOH, R.T. 24 h., 80%; (ix) PCC, CH$_2$Cl$_2$, R.T., 6 h. (x) NaClO$_2$, NaH$_2$PO$_4$·H$_2$O, t-butanol, 2-methyl-2-butene; (xi) p-octyl aniline, PyBOP, DIEA, CH$_2$Cl$_2$, R.T., overnight; (xii) H$_2$, 10% Pd/C, EtOH, R.T. overnight; (xiii) TMSBr, CH$_2$Cl$_2$, R.T., 4 h., then 95% CH$_3$OH in H$_2$O, R.T., 1 h.

[(Diethoxy-phosphoryl)-fluoro-methyl]-phosphonic acid diethyl ester (31). To a slurry of 95% NaH (9 mg, 0.375 mmol) in THF (1.5 mL) was added tetraethyl methylene diphosphonate, (30) (100 mg, 0.347 mmol) at 0° C. The mixture was allowed to warm to room temperature and stirred for 45 minutes. The mixture was subsequently cooled to 0° C. and Selectfluor (153 mg, 0.432 mmol) was added in one portion. The mixture was allowed to warm to room temperature and stirred for 1 hr. The reaction mixture was concentrated in vacuo and purified by column chromatography on SiO$_2$ (3% MeOH in EtOAc) to yield 56 mg (53%) of a clear liquid.

2-Amino-3-hydroxy-propionic acid methyl ester (33). To a solution of D-serine (5 g, 47.58 mmol) in methanol (100 mL), stirring under N$_2$ $_{(g)}$ at 0° C., was added thionyl chloride (20.8 mL, 285.5 mmol) dropwise. The reaction mixture was allowed to warm to room temperature, stirred for 4-6 hours, then concentrated under reduced pressure. The crude material was reconstituted in Et$_2$O and concentrated, in the same manner. This was repeated numerous times until SOCl$_2$ could not be detected. The crude material was confirmed by NMR experiments and carried on to the following step.

2-tert-Butoxycarbonylamino-3-hydroxy-propionic acid methyl ester (34). To a solution of the crude methyl ester serine (33) in CH$_2$Cl$_2$ (100 mL), stirring under N$_2$ $_{(g)}$, was added di-tert-butyl pyrocarbonate (11.420 g, 52.34 mmol) and triethyl amine (16.6 mL, 118.95 mmol). The reaction mixture was allowed to stir at room temperature for 4 hours, then poured over NH$_4$Cl at 0° C. The organic layer was extracted with 10% HCl (2×), then NaHCO$_3$ and brine. The organic layer was then dried over anhydrous Na$_2$SO$_4$, filtered and concentrated under reduced pressure. The crude material was again carried on to the following step.

2,2-Dimethyl-oxazolidine-3,4-dicarboxylic acid 3-tert-butyl ester 4-methyl ester (35). To a solution of (34) in CH$_2$Cl$_2$, stirring under nitrogen at 0° C., was added 2,2-dimethoxypropane (29.5 mL, 237.9 mmol) and p-toluene sulfonic acid monohydrate (9.050 g, 47.58 mmol). The mixture was removed from the ice bath after 15 minutes and stirred at room temperature for 1.5 hours. The reaction mixture was poured into 50 mL of saturated NaHCO$_3$ $_{(aq)}$ and extracted with diethyl ether (3×50). The organic layer was extracted with NaHCO$_3$ and brine, then dried over anhydrous MgSO$_4$, filtered and concentrated under reduced pressure. The crude material was purified by flash chromatography on SiO$_2$ (1:1 EtOAc/Hexanes) to yield 7.659 g (62%, 3 steps) of a clear liquid.

4-Hydroxymethyl-2,2-dimethyl-oxazolidine-3-carboxylic acid tert-butyl ester (36). To a mixture of NaBH$_4$ (2.247 g, 59.08 mmol) and LiCl (2.505 g, 59.08 mmol) in EtOH (42 mL), stirring under nitrogen at 0° C., was added (35) (7.659 g, 29.54 mmol) in THF (30 mL) dropwise. This mixture was allowed to warm to room temperature and continued stirring for 48 hours. The precipitate was filtered and washed with ethanol. The washings were concentrated and extracted with EtOAc. The organic layer was then washed with brine and dried over anhydrous Na$_2$SO$_4$. Column chromatography on SiO$_2$ (1:1 EtOAc/Hexanes) was utilized to purify 6.101 g (89%) of the title compound as a white solid.

4-Formyl-2,2-dimethyl-oxazolidine-3-carboxylic acid tert-butyl ester (37). To a solution of (36) (80 mg, 0.346 mmol) stirring in CH$_2$Cl$_2$ (2 mL), under a nitrogen atmosphere, was added pyridinium chlorochromate (150 mg, 0.694 mmol). The reaction mixture was allowed to stir overnight then filtered through a plug of silica gel. The crude aldehyde was carried on to the following step.

4-[2-(Diethoxy-phosphoryl)-2-fluoro-vinyl]-2,2-dimethyl-oxazolidine-3-carboxylic acid tert-butyl ester (38). To a stirred suspension of LiCl (18 mg, 0.416 mmol) in dry acetonitrile (3.5 mL), under nitrogen at room temperature, were added diphosphonate (31) (127 mg, 0.416 mmol), DBU (0.05 mL, 0.347 mmol) and garner's aldehyde (37) (80 mg, 0.347 mmol). The reaction mixture was allowed to stir overnight then concentrated in vacuo. The crude material was isolated by column chromatography on $SiO_2$, (1:1 EtOAc/Hexanes) to yield 47 mg (40%, two steps) of a clear liquid.

(3-tert-Butoxycarbonylamino-1-fluoro-4-hydroxy-but-1-enyl)phosphonic acid diethyl ester (39). To compound (38) (47 mg, 0.123 mmol) stirring in EtOH (1 mL) was added Dowex 50×8 (150 mg), which washed with EtOH and dried. The reaction was allowed to stir under nitrogen and at room temperature for 24 hours. The reaction mixture was filtered and the precipitate washed with excess EtOH, then concentrated in vacuo. The crude material was purified by column chromatography on $SiO_2$ (1:1 EtOAc/Hexanes) to yield 34 mg of the expected product.

EXAMPLE 3

[γ-35 S]GTP Binding Assay for Measuring S1P Activity

Transient Expression in HEK293T Cells.

Human or mouse S1P5 DNA was mixed with an equal amount of DNA encoding a rat Gi2R protein as well as DNAs encoding cow β1 and γ2 proteins and used to transfect monolayers of HEK293T cells using the calcium phosphate precipitate method. After 60 h, cells were harvested, and microsomes were prepared, aliquoted, and stored at −70° C. until use.

[γ-35 S]GTP Binding.

Briefly, 5 ug of membranes from S1P expressing HEK293T cells was incubated in 0.1 mL of binding buffer (in mM: HEPES 50, NaCl 100, $MgCl_2$ 5), pH 7.5, containing 5 ug of saponin, 10 uM GDP, 0.1 nM [γ-35 S]GTP (1200 Ci/mmol), and test lipid. After incubating for 30 min at 30° C., bound radionuclide was separated from free by filtration through Whatman GF/C paper using a Brandel Cell Harvester (Gaithersburg, Md.).

Stable Expression in RH7777 Cells.

Rat hepatoma RH7777 cell monolayers were transfected with human or mouse S1P5/pCR3.1 DNA using the calcium phosphate precipitate method, and clonal populations expressing the neomycin *phosphotransferase* gene were selected by addition of Ge-neticin (G418) to the culture medium. The RH7777 cells were grown in monolayers at 37° C. in a 5% $CO_2$/95% air atmosphere in growth medium consisting of 90% MEM, 10% fetal bovine serum, 2 mM glutamine, and 1 mM sodium pyruvate.

Measurement of cAMP Accumulation.

Assay of cAMP accumulation was performed as described previously (See Im et al., J. Biol. Chem. 275, 14281-14286 (2000), the disclosure of which is incorporated herein). Assays were conducted on populations of $5 \times 10^5$ cells stimulated with 1 uM forskolin in the presence of the phosphodiesterase inhibitor isomethylbutylxanthine (IBMX, 1 mM) for 15 min. cAMP was measured by automated radioimmunoassay. The GTPγS studies were performed using zebrafish S1P1 overexpressed rat RH-7777 and human hS1P1, hS1P2, hS1P3 and hS1P5 overexpressed human HEK293 cells. Table 1 shows the $EC_{50}$ values for each of the S1P analogs at S1P receptors: S1P1, S1P2, S1P3 and S1P5. In addition to testing the human S1P receptors (hS1P1, hS1P2, hS1P3 and hS1P5), a zebrafish S1P receptor (zS1P1) and mouse S1P (mS1P5) were also tested.

TABLE 1

| $EC_{50}$ Values (nM) for S1P Analogues at Recombinant S1P Receptors | | | | | |
|---|---|---|---|---|---|
| | $zS1P_1$ | $hS1P_1$ | $hS1P_3$ | $hS1P_2$ | $hS1P_5$ | $mS1P_5$ |
| S1P | 54.6 | 0.9 | 1.1 | 2.9 | 43.9 | 12.7 |
| VPC22041 | 2053.0 | 598.4 | 845.4 | 973.2 | 645.5 | >5000 |
| VPC22051 | >5000 | 322.1 | 601.9 | 2760.0 | >5000 | >5000 |
| VPC22053 | >5000 | 397.0 | 862.4 | 2685.0 | 1606.0 | 2006.0 |
| VPC22063 | >5000 | 1805.0 | 878.6 | >5000 | 1220.0 | 1326.0 |
| VPC22135 | 1625.0 | 12.7 | 50.8 | 2107.0 | >5000 | 1821.0 |

S1P increases GTPγS binding significantly (2-5-fold) at each receptor with $EC_{50}$ values from 1 to 55 nM. The synthetic series consisted of five dihydro S1P of the general formula:

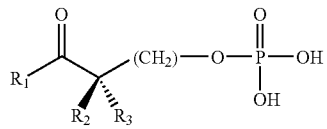

wherein

VPC22041 (2S): $R_1$ is $NH(CH_2)_{11}CH_3$, $R_2$ is $NH_2$ and $R_3$ is H;

VPC22053 (2S): $R_1$ is $O(CH_2)_{13}CH_3$, $R_2$ is $NH_2$ and $R_3$ is H;

VPC22051 (2S): $R_1$ is $NH(CH_2)_{13}CH_3$, $R_2$ is $NH_2$ and $R_3$ is H;

VPC22063 (2S): $R_1$ is $NH(CH_2)_{15}CH_3$, $R_2$ is $NH_2$ and $R_3$ is H; and VPC22135 (2R): $R_1$ is $NH(CH_2)_{13}CH_3$, $R_2$ is H and $R_3$ is $NH_2$ The amide-containing compounds contained alkyl chains of 12 (VPC22041), 14 (VPC22053), or 16 (VPC22063) carbons, and the 2'-amino group was in the natural configuration (S), except for VPC22135, wherein the 2'-amino was in the (R) configuration. VPC22053 and VPC22135 are an enantiomeric pair, while VPC22051 is the ester-containing equivalent of VPC22053 (see Scheme 4). All of these compounds had significant agonist activity at each of the S1P receptors, although none were as potent as S1P itself (see Table 1). In particular, on the S1P5 transfected HEK293 cells, the five mimetics showed $EC_{50}$=s of approximately 1 μM, where as the $EC_{50}$ of S1P itself on the same cells is closer to 10 nM. However, one compound, VPC22135, approached the potency of S1P at both the human S1P1 and human S1P3 receptors. Curiously, this compound has the amino group in the unnatural (R) configuration. Its enantiomer, VPC22053, was more than 1 log order less potent at both the S1P1 and S1P3 receptors. The results obtained for the S1P1 transfected RH-7777 cells showed a preference for binding with the 18 carbon backbone mimetic compounds (identical to S1P) over the 16 and 20 carbon backbone mimetic compounds.

Assay of phenyl imidazole compounds vpc24287 (phosphate) and vpc24289 (phosphothionate) at individual human sphingosine 1-phosphate (S1P) receptors was also conducted.

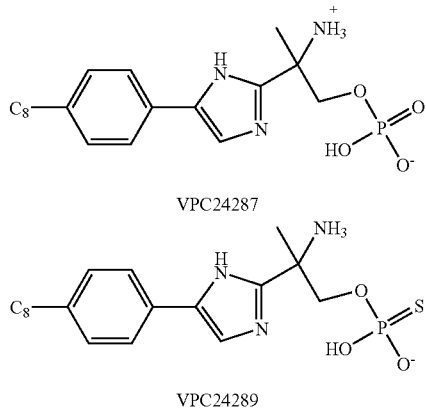

VPC24287

VPC24289

Methods: Human recombinant S1P receptor type DNAs were mixed with DNAs encoding human Gαi2, cow β1 and cow 72 proteins and introduced into cultured HEK293T cells by transfection. After about 48 hours, cells were harvested and crude membranes prepared. Ligand driven binding of a non-hydrolyzable GTP analog, GTP[γ-$^{35}$S], was measured in a rapid filtration assay. Details of the assay are found in: Brinkmann, V., Davis, M. D., Heise, C. E., Albert, R., Cottens, W., H of, R., Bruns, C., Prieschl, E., Baumruker, T., Hiestand, P., Foster, C. and Lynch, K. R. The immune modulator, FTY720, targets sphingosine 1-phosphate receptors. J. Biol. Chem. 277: 21453-21457 (2002). Total counts per minute were determined for S1P, vpc24287 and vpc24289 activation of the S1P receptor subtypes with the maximal counts received by S1P designated as 100% activation of the S1P receptor. The results are provided in FIG. 6A-6D demonstrating vpc24287 and vpc24289 activation of the S1P receptor subtypes relative to S1P.

EXAMPLE 4

Biological Assay of the Synthesized Mimetics

An additional series of compounds was tested using the GTP$_c$S binding assay described in Example 2 and in Im et al., J. Biol. Chem. 275, 14281-14286 (2000), the disclosure of which is incorporated herein). The compounds tested for binding at human S1P receptors (hS1P1, hS1P2, hS1P3, hS1P4 and hS1P5) have the general structure:

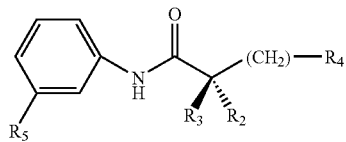

wherein

VPC23019: $R_5$ is $(CH_2)_7CH_3$, $R_2$ is $NH_2$, $R_3$ is H and $R_4$ is phosphate;
VPC23031: $R_5$ is $(CH_2)_7CH_3$, $R_2$ is $NH_2$, $R_3$ is H and $R_4$ is phosphate;
VPC23065: $R_5$ is $(CH_2)_9CH_3$, $R_2$ is $NH_2$, $R_3$ is H and $R_4$ is hydroxy;
VPC23069: $R_5$ is $(CH_2)_9CH_3$, $R_2$ is $NH_2$, $R_3$ is H and $R_4$ is phosphate;
VPC23075: $R_5$ is $(CH_2)_8CH_3$, $R_2$ is $NH_2$, $R_3$ is H and $R_4$ is hydroxy;
VPC23079: $R_5$ is $(CH_2)_8CH_3$, $R_2$ is $NH_2$, $R_3$ is H and $R_4$ is phosphate;

or have the general structure:

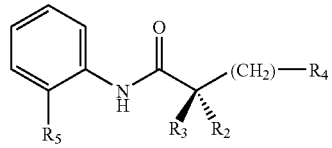

wherein

VPC23087: $R_5$ is $(CH_2)_7CH_3$, $R_2$ is $NH_2$, $R_3$ is H and $R_4$ is hydroxy;
VPC23089: $R_5$ is $(CH_2)_7CH_3$, $R_2$ is $NH_2$, $R_3$ is H and $R_4$ is phosphate;

Each of the compounds tested (VPC 23019, 23031, 23065, 23069, 23087, 23089, 23075, 23079) failed to show significant activity at the S1P2 receptor.

Compounds VPC23065, VPC23087 and VPC23075 are primary alcohols and thus lack the phosphate headgroup. Yet several of these compounds exhibit activity at S1P receptors (See FIGS. 2A, 2B, 2C, 3A, 3B, 3C and 4C) and each of these compounds shows good agonist activity at the S1P4 receptor.

Figure 2A:
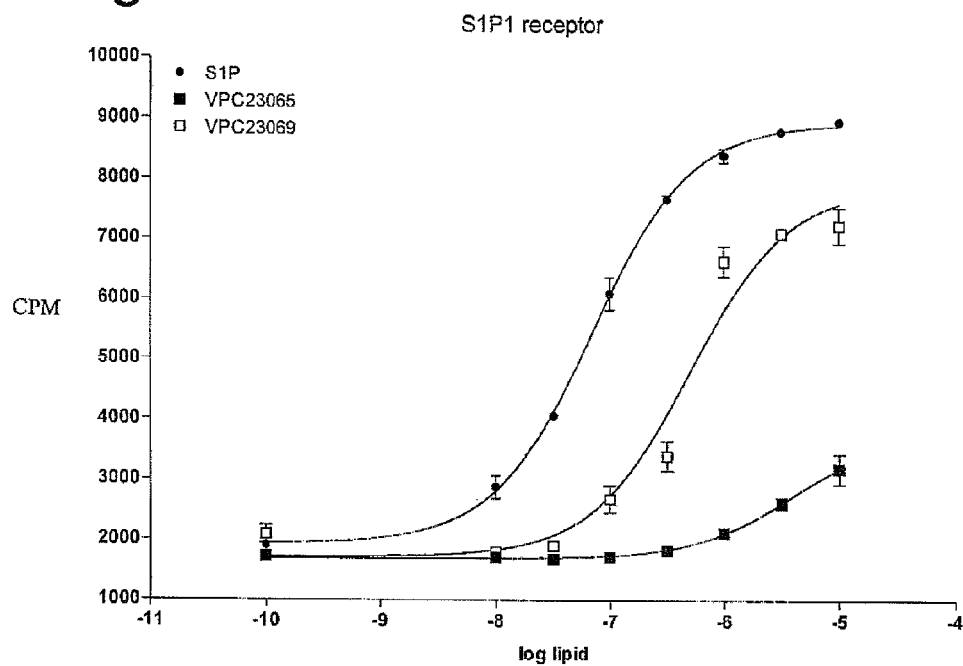
FIG. 2A-2E are graphic representations of [γ-35 S]GTP binding to HEK293T cell membranes (containing different S1P receptors) in response to S1P, VPC23065 and VPC23069.
Figure 2B:
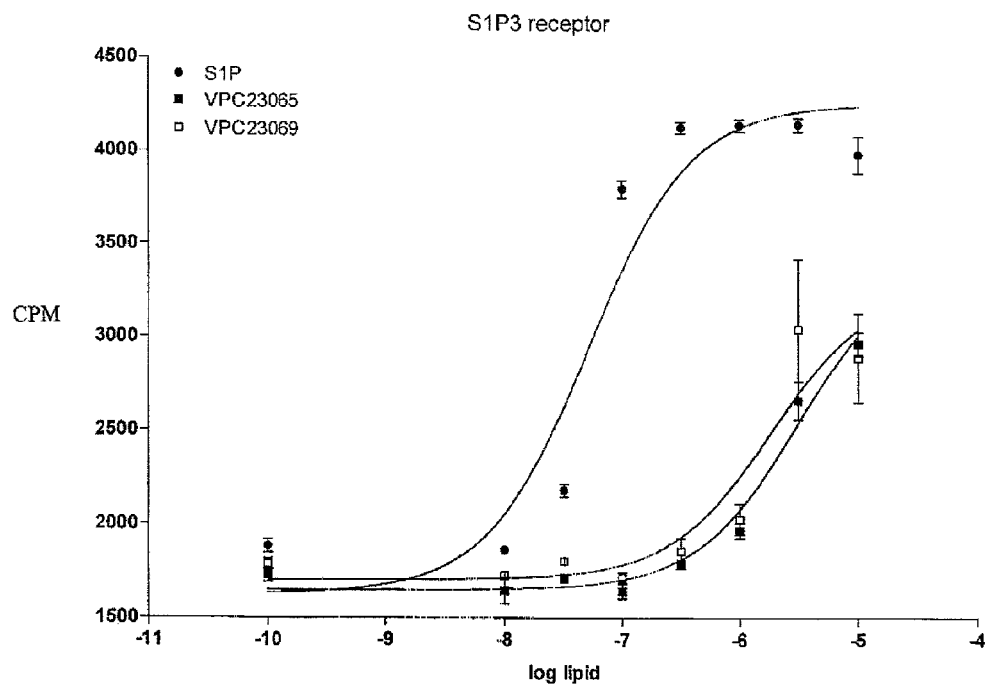
Figure 2C:
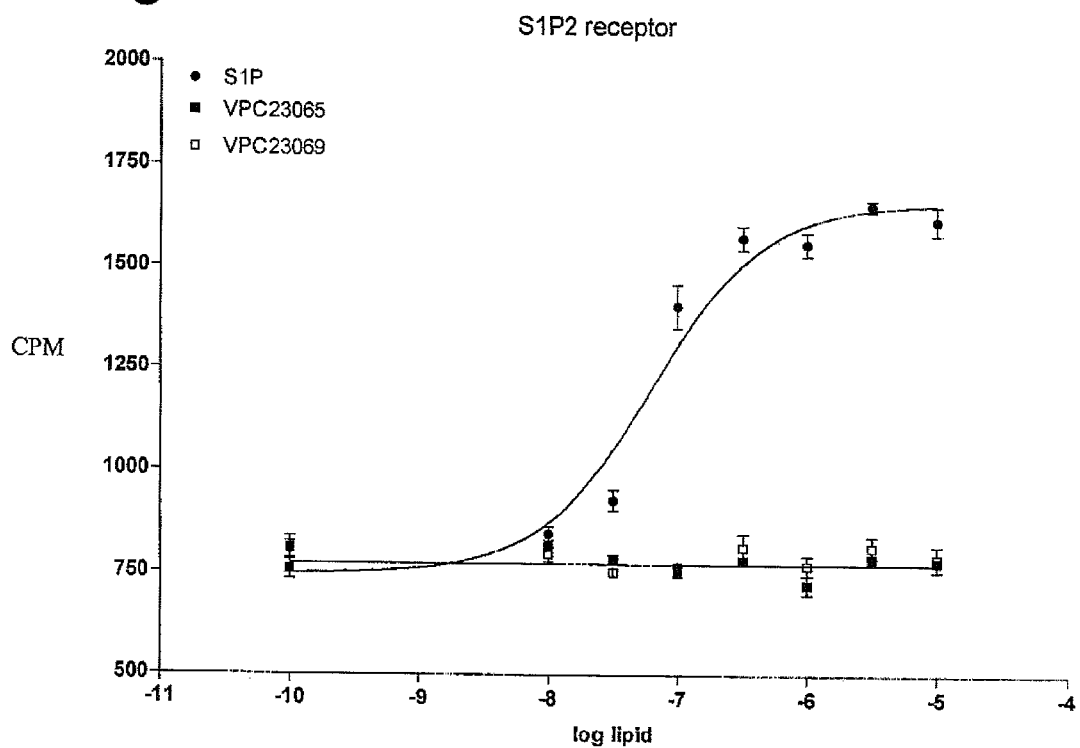
Figure 2D:
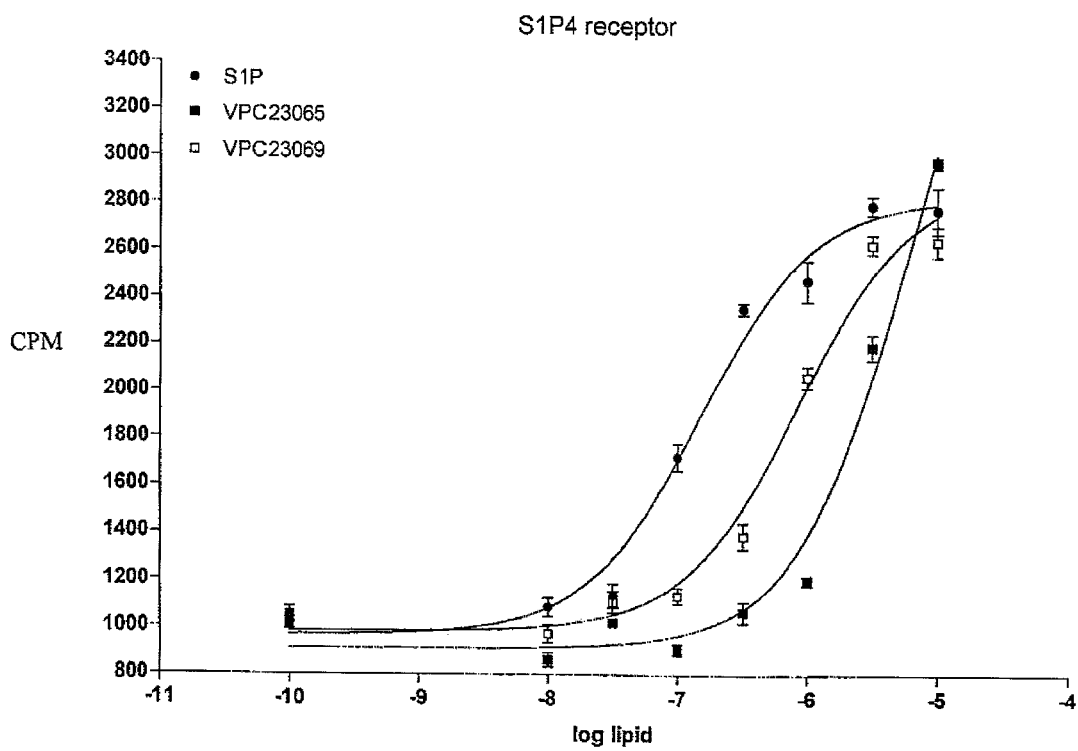
Figure 2E:
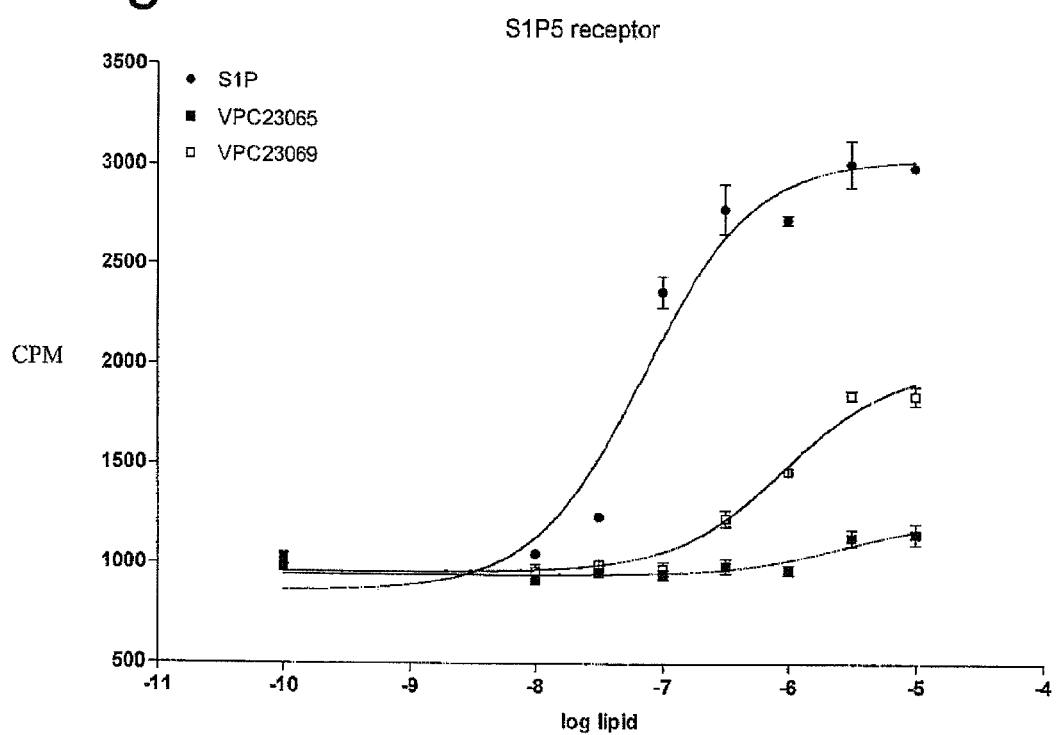
Figure 3A:
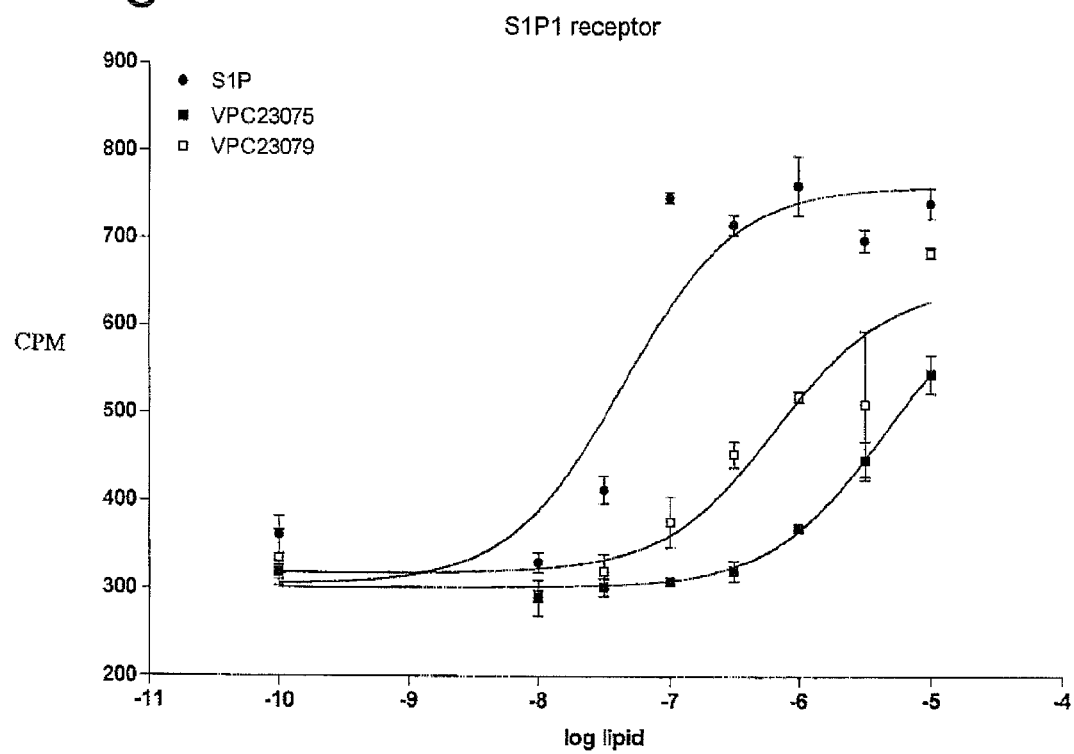
FIG. 3A-3E are graphic representations of [γ-35 S]GTP binding to HEK293 T cell membranes (containing different S1P receptors) in response to S1P, VPC23075 and VPC23079.
Figure 3B:
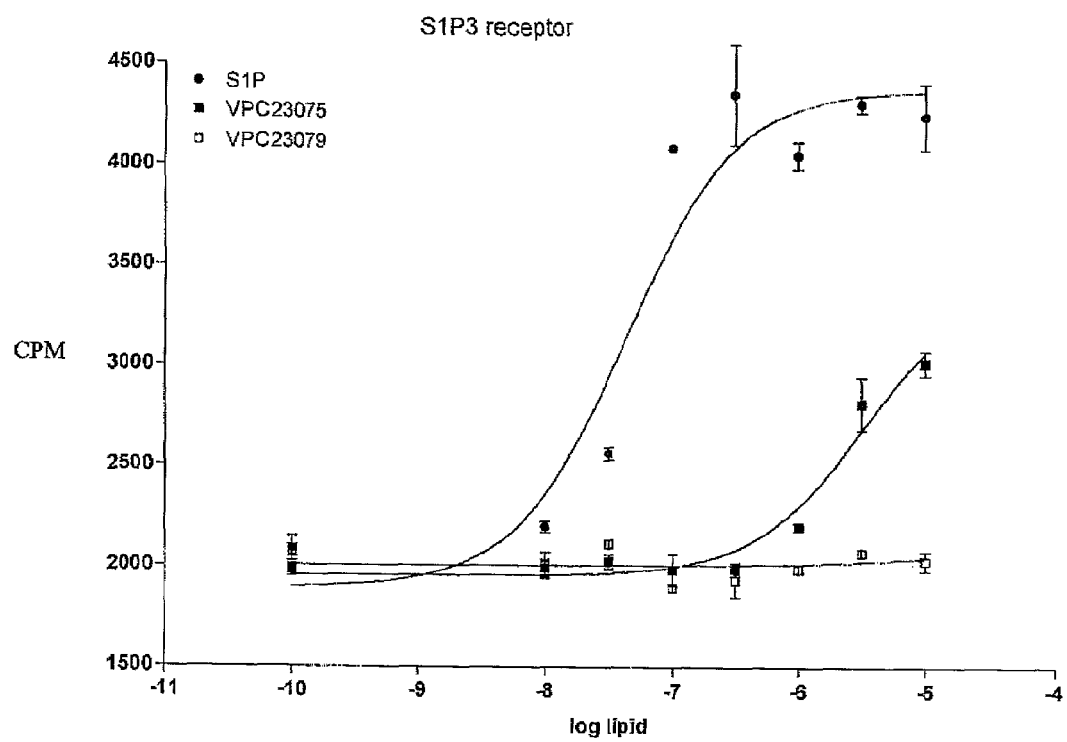
Figure 3C:
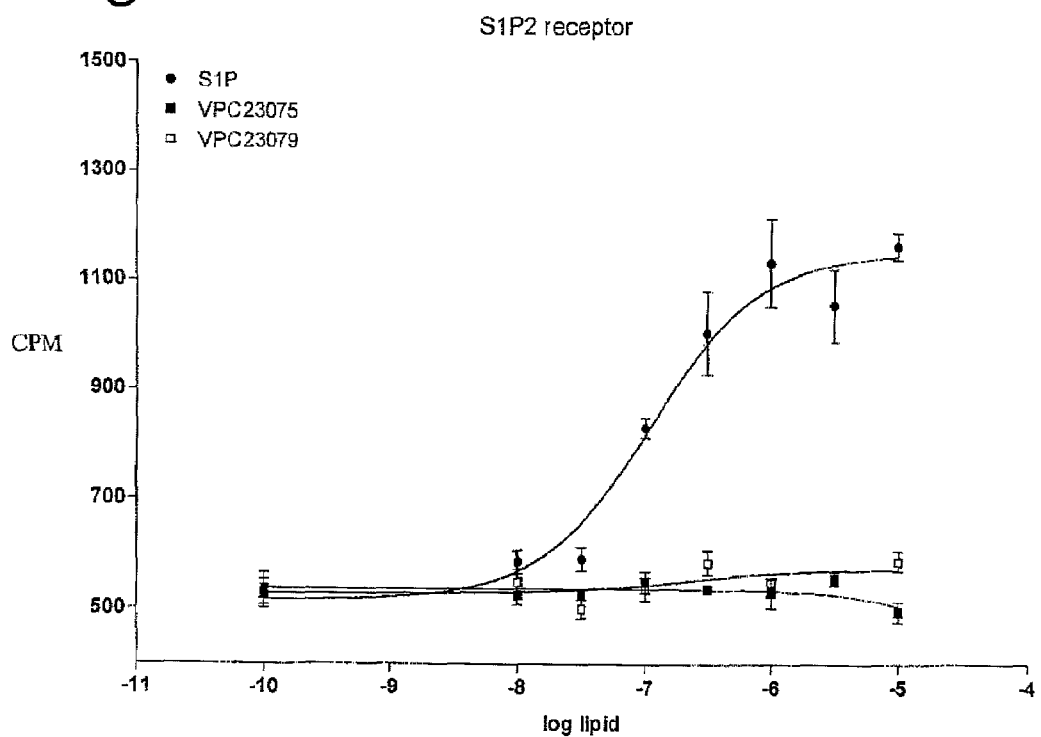
Figure 3D:
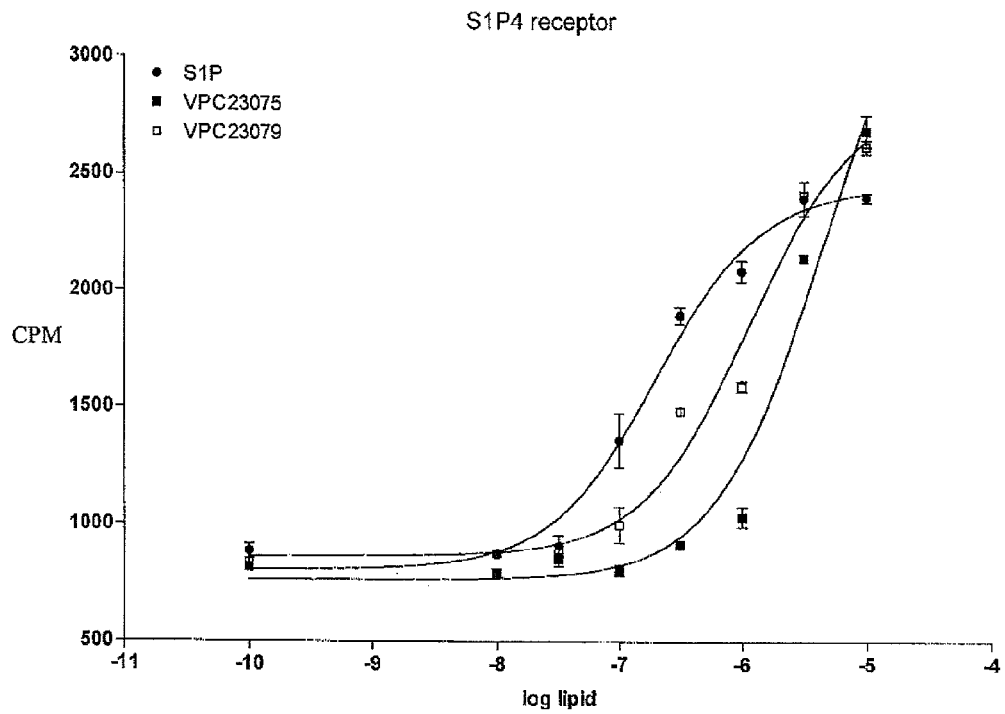
Figure 3E:
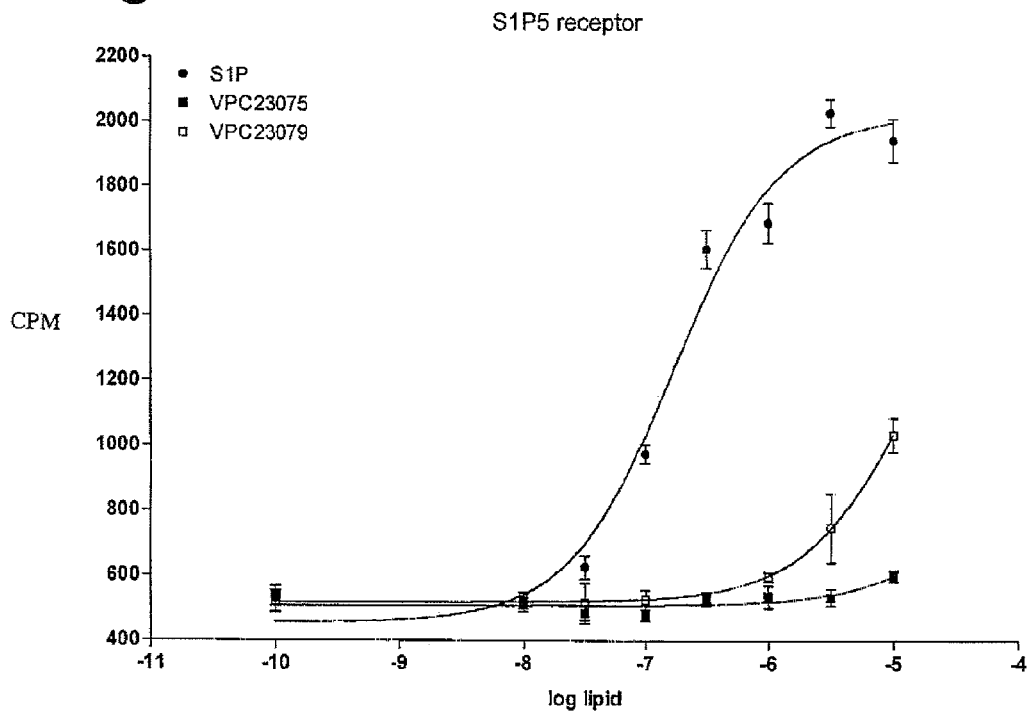
Figure 4A:
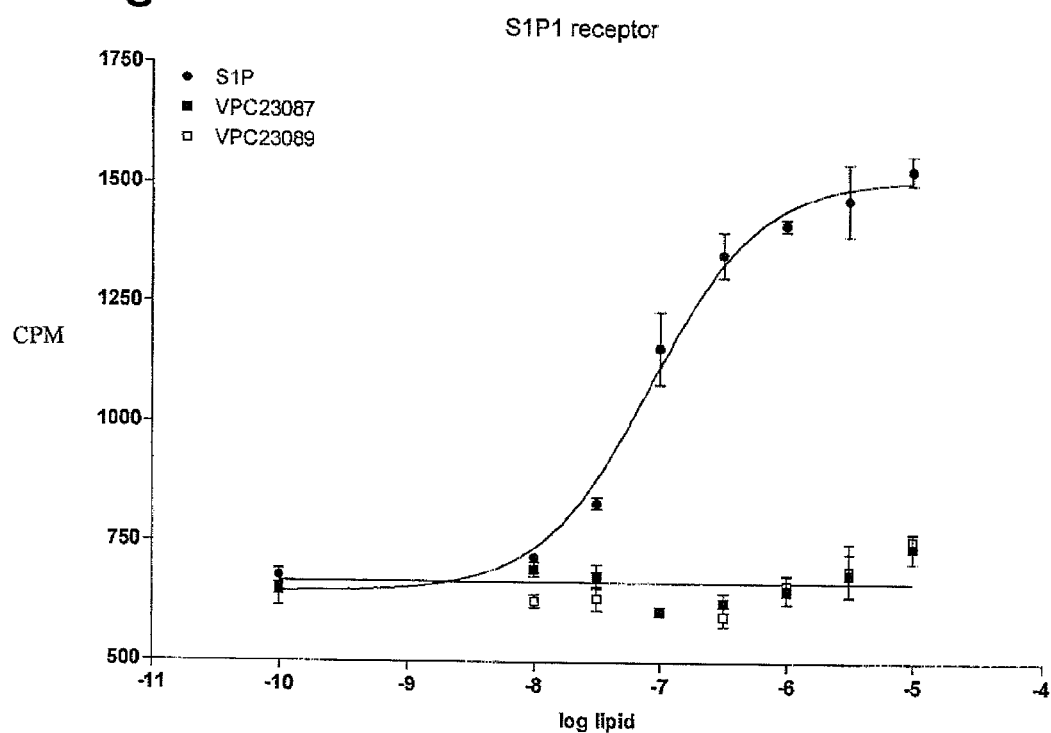
FIG. 4A-4E are graphic representations of [γ-35 S]GTP binding to HEK293T cell membranes (containing different S1P receptors) in response to S1P, VPC23087 and VPC23089.
Figure 4B:
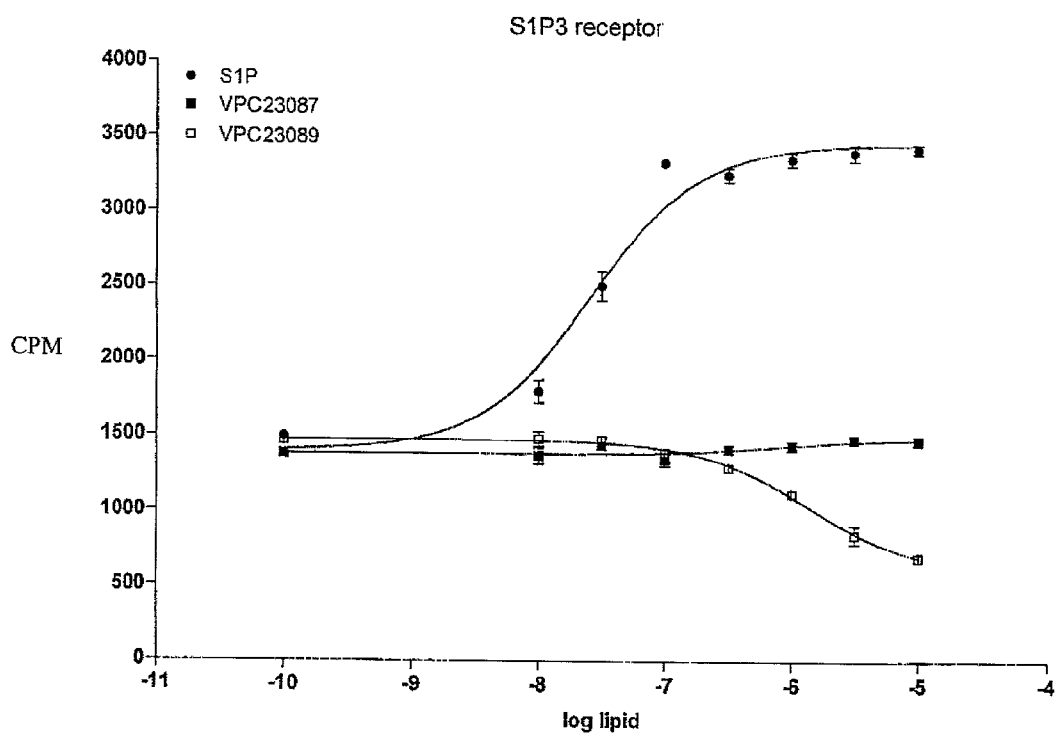
Figure 4C:
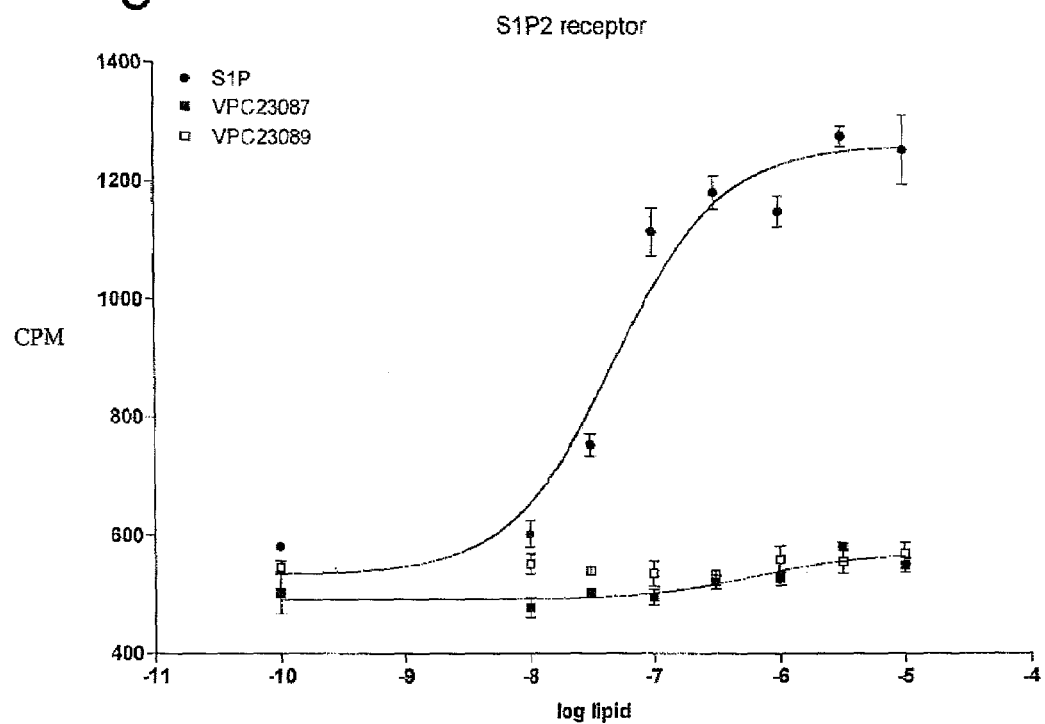
Figure 4D:
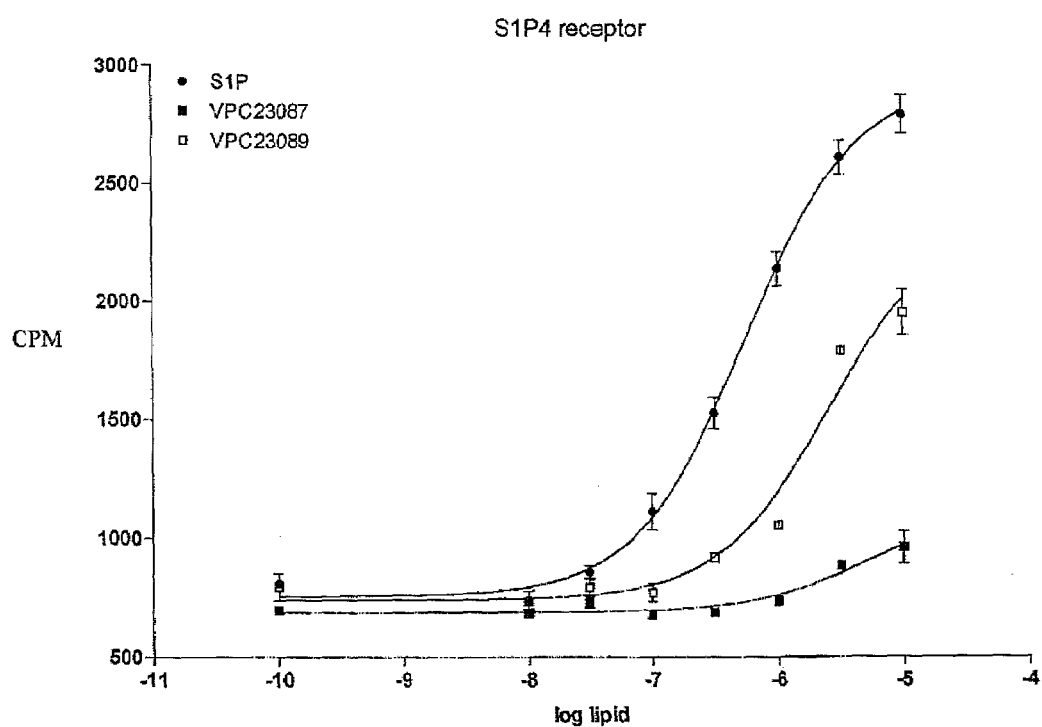
Figure 4E:
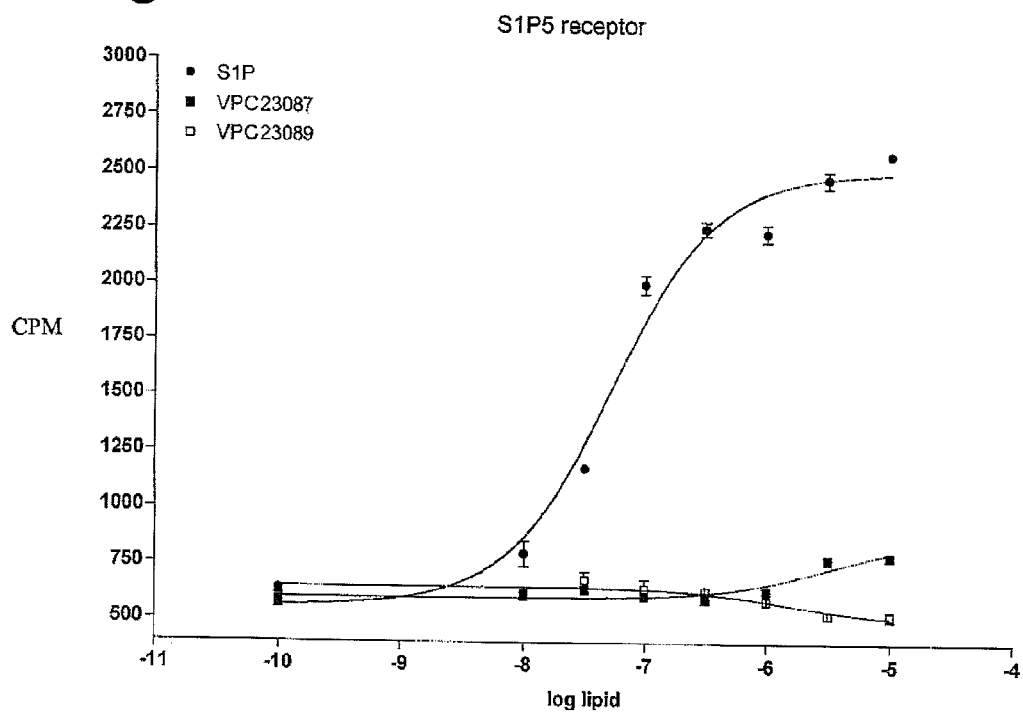

The GTP$_c$S binding assay revealed that VPC23031, VPC23019, VPC23089 are inverse agonists (antagonists) of the S1P3 receptor (See FIGS. 1A and 4A), but this inverse agonism becomes agonism when the alkyl chain length is 9 carbons (VPC23079) or 10 (VPC23069), see FIGS. 2A and 3A.

Figure 5A:
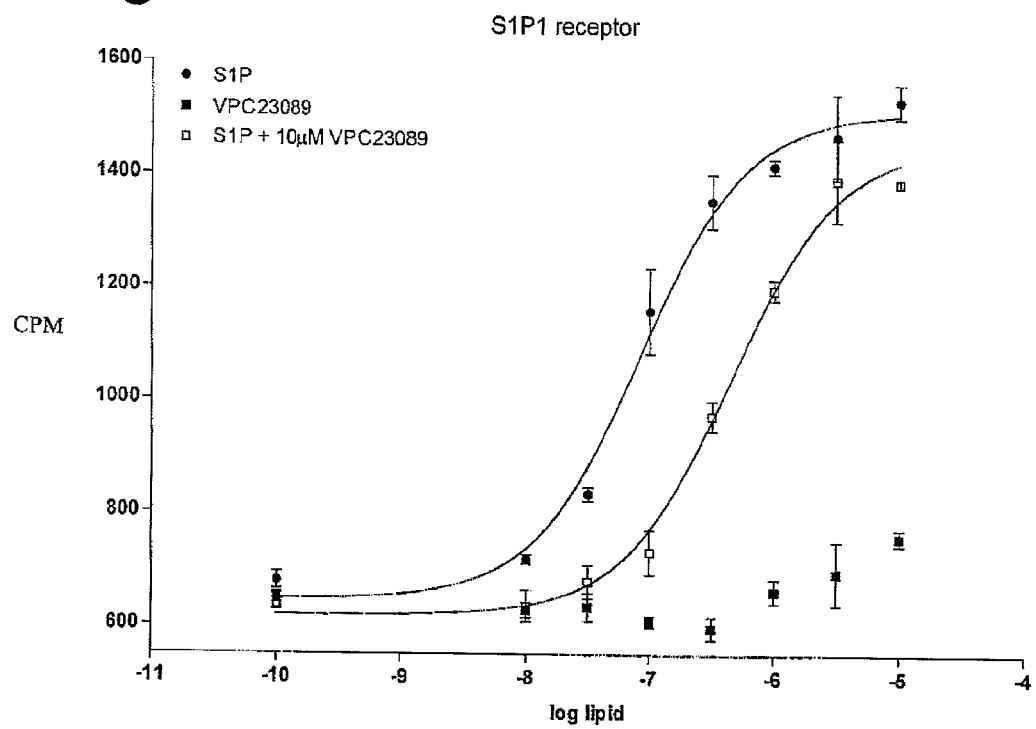
FIGS. 5A and 5B.
Figure 5B:
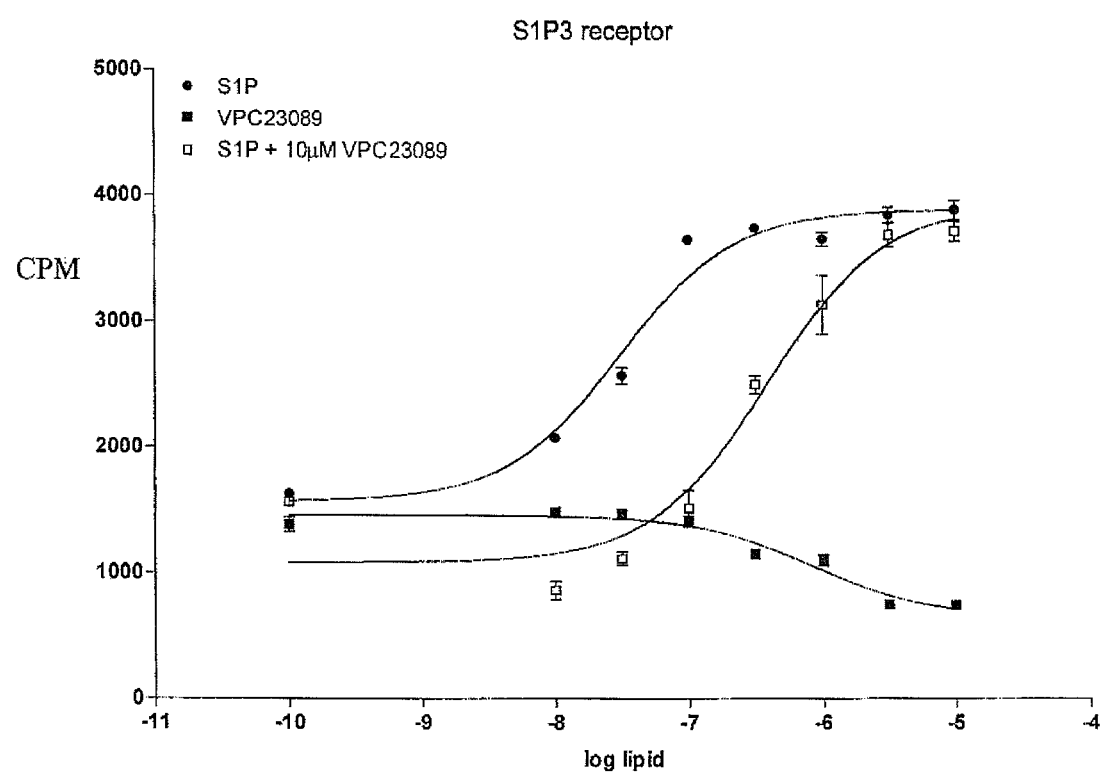
Figure 6A:
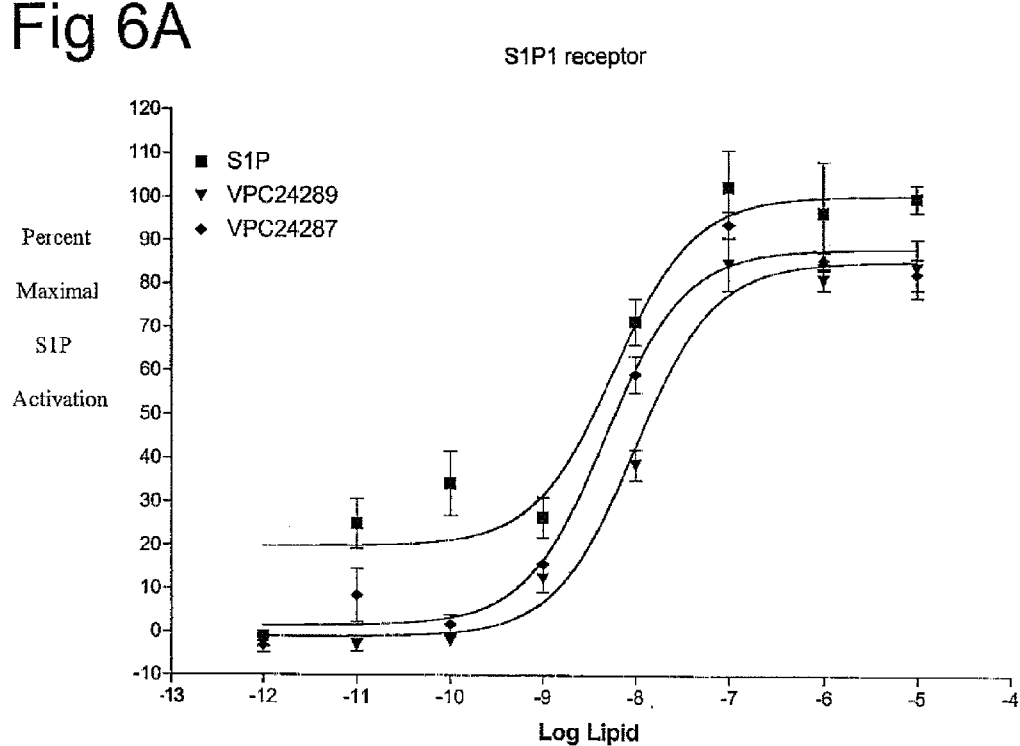
FIGS. 6A-6D are graphic representations of [γ-35 S]GTP binding to HEK293T cell membranes (containing different S1P receptors) in response to S1P, VPC24289 and VPC24287.
Figure 6B:
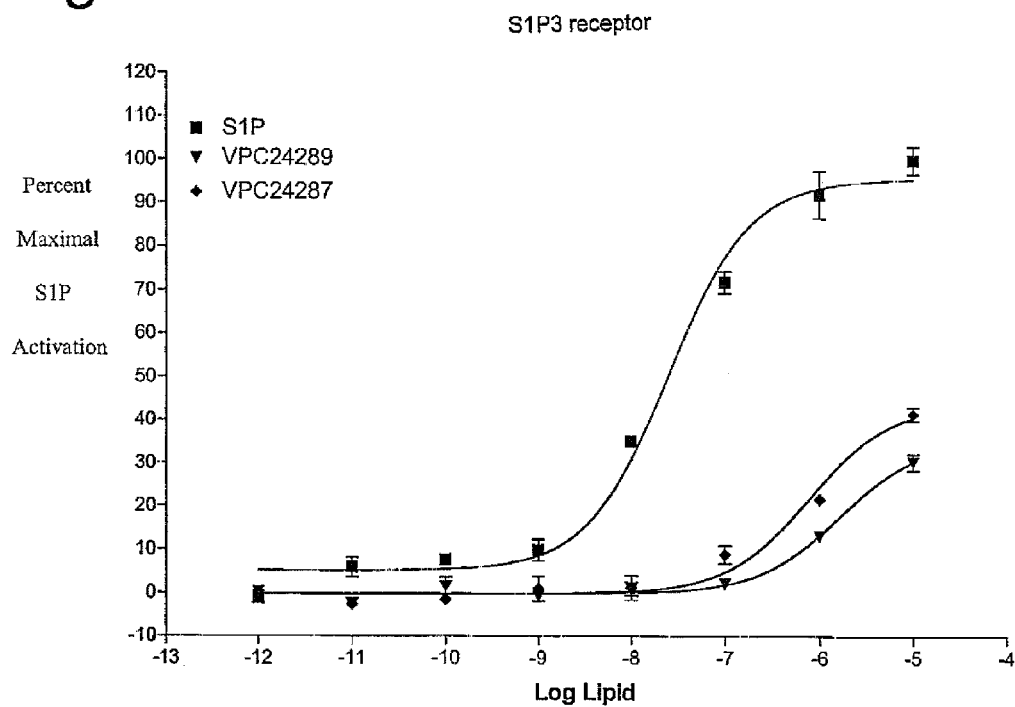
Figure 6C:
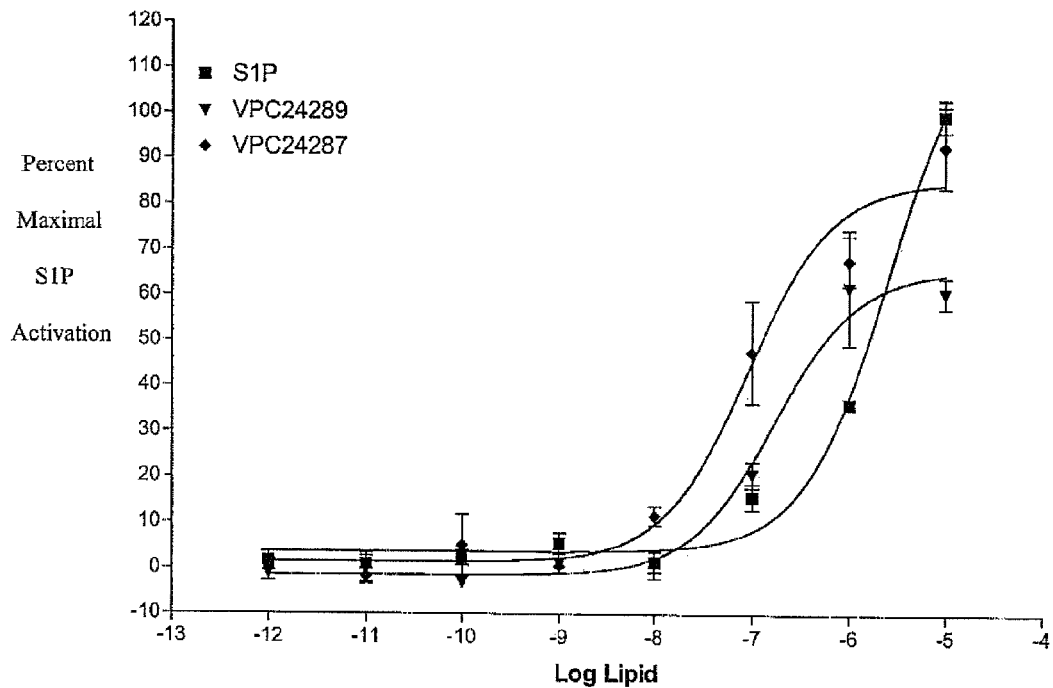
Figure 6D:
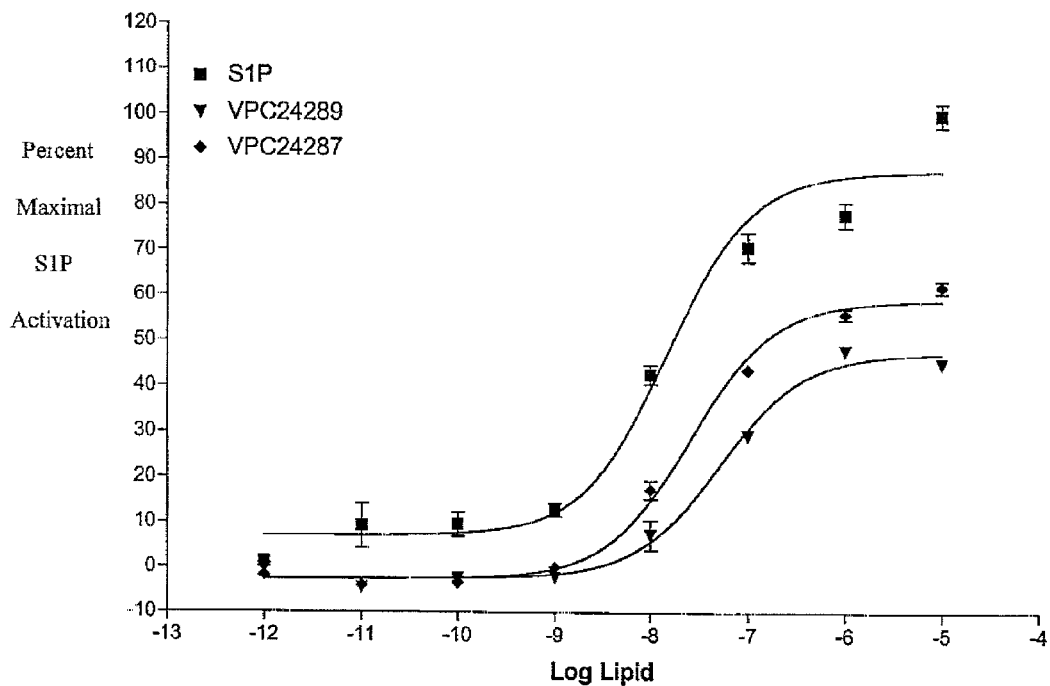

VPC23089 and VPC23019 are isomers, with the VPC23089 compound having the alkyl chain ortho and the VPC23019 compound meta; in both cases the alkyl chain has 8 carbons, but surprisingly, when one goes from ortho to meta, antagonism at S1P1 is realized (compare FIG. 1A with the competition curve FIG. 5A).

The invention claimed is:
1. A compound of the formula:

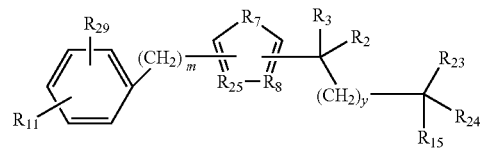

wherein
$R_{11}$ is $C_5$-$C_{12}$ alkyl, $C_5$-$C_{12}$ alkenyl, $C_5$-$C_{12}$ alkynyl, $C_5$-$C_{12}$ alkoxy, $C_5$-$C_{10}$ (aryl)$R_{20}$, $C_5$-$C_{10}$ (heteroaryl)$R_{20}$, $C_5$-$C_{10}$ (cycloalkyl)$R_{20}$, $C_5$-$C_{10}$ alkoxy(aryl)$R_{20}$, $C_5$-$C_{10}$ alkoxy(heteroaryl)$R_{20}$ or $C_5$-$C_{10}$ alkoxy(cycloalkyl)$R_{20}$;
wherein $R_{20}$ is H or $C_1$-$C_{10}$ alkyl;
$R_{29}$ is H or halo;
$R_2$ is $NH_2$;
$R_3$ is H, $C_1$-$C_6$ alkyl, $(C_1$-$C_4$ alkyl)OH, or $(C_1$-$C_4$ alkyl)$NH_2$;
$R_{23}$ is H, F, $NH_2$, OH, $CO_2H$, $C_1$-$C_6$ alkyl, $(C_1$-$C_4$ alkyl)OH, or $(C_1$-$C_4$ alkyl)$NH_2$;

$R_{24}$ is H, F, $C_1$-$C_4$ alkyl or $PO_3H_2$; or $R_{23}$ together with $R_{24}$ and the carbon to which they are attached form a carbonyl group;

$R_{25}$, $R_7$, and $R_8$ are independently O, S, $CHR_{26}$, $CR_{26}$, $NR_{26}$, or N;

wherein $R_{26}$ is H, F or $C_1$-$C_4$ alkyl;

$R_{15}$ is hydroxy, phosphonate, or

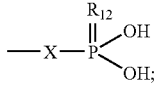

wherein $R_{12}$ is O, NH or S;
X is O, NH or S;
y and m are integers independently ranging from 0 to 4;
or a pharmaceutically acceptable salt or tautomer thereof.

2. The compound of claim 1, of the formula:

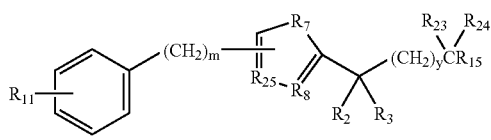

wherein
$R_{11}$ is $C_5$-$C_{12}$ alkyl, $C_5$-$C_{12}$ alkenyl, $C_5$-$C_{12}$ alkoxy, or $C_5$-$C_{12}$ alkynyl;
$R_7$ and $R_8$ are independently O, S, $CHR_{26}$, $CHR_{26}NR_{26}$, or N;
wherein $R_{26}$ is H, F or $C_1$-$C_4$ alkyl;
$R_{25}$ is N or CH;
$R_2$ is $NH_2$;
$R_3$ is H, $C_1$-$C_4$ alkyl, ($C_1$-$C_4$ alkyl)OH, or ($C_1$-$C_4$ alkyl)$NH_2$;
$R_{15}$ is hydroxy, phosphonate, or

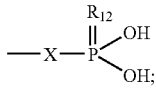

wherein X and $R_{12}$ are independently O or S;
$R_{23}$ is H, F, OH, $C_1$-$C_4$ alkyl, $CO_2H$ or ($C_1$-$C_4$ alkyl)OH;
$R_{24}$ is H, F, $C_1$-$C_4$ alkyl or $PO_3H_2$, or $R_{23}$ together with $R_{24}$ and the carbon to which they are attached form a carbonyl group; and
y and m are integers independently ranging from 0 to 4;
or a pharmaceutically acceptable salt or tautomer thereof.

3. The compound of claim 2 wherein
m is 0;
y is 0 or 1;
$R_{23}$ is H or F; and
$R_{24}$ is H, F or $C_1$-$C_4$ alkyl;
or a pharmaceutically acceptable salt or tautomer thereof.

4. The compound of claim 2, wherein $R_3$ is $C_1$-$C_3$ alkyl or ($C_1$-$C_4$ alkyl)OH;
or a pharmaceutically acceptable salt or tautomer thereof.

5. The compound of claim 3, wherein
$R_7$ is NH; and
X is O;
or a pharmaceutically acceptable salt or tautomer thereof.

6. The compound of claim 5, wherein
y is 0; and
$R_{15}$ is OH;
or a pharmaceutically acceptable salt or tautomer thereof.

7. The compound of claim 4, of the formula:

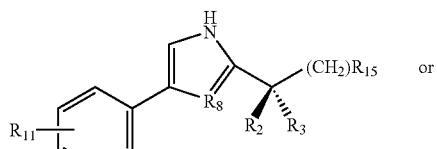

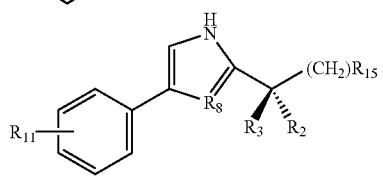

wherein $R_{11}$ is $C_5$-$C_{12}$ alkyl, $C_5$-$C_{12}$ alkoxy, or $C_5$-$C_{12}$ alkenyl; and
$R_8$ is N;
or a pharmaceutically acceptable salt or tautomer thereof.

8. The compound of claim 7, wherein
$R_{15}$ is hydroxy or

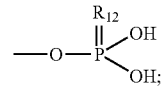

wherein $R_{12}$ is O or S;
or a pharmaceutically acceptable salt or tautomer thereof.

9. The compound of claim 8, wherein $R_{11}$ is $C_5$-$C_9$ alkyl;
$R_{15}$ is OH and
$R_3$ is $CH_3$, $CH_2CH_3$, $CH_2OH$, $CH_2CH_2OH$ or $CH_2CH_2CH_2OH$;
or a pharmaceutically acceptable salt or tautomer thereof.

10. The compound of claim 7, 2-amino-2-[5-(4-octyl-phenyl)-1H-imidazol-2-yl]-propan-1-ol; or a pharmaceutically acceptable salt or tautomer thereof.

11. A composition comprising a compound of claim 1, and a pharmaceutically acceptable carrier.

12. A pharmaceutical composition comprising a compound of the formula

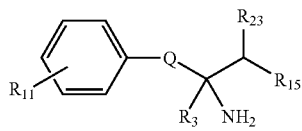

wherein $R_{11}$ is $C_5$-$C_{18}$ alkyl, $C_5$-$C_{18}$ alkoxy, or $C_5$-$C_{18}$ alkenyl;
Q is $C_3$-$C_6$ optionally substituted cycloalkyl, $C_3$-$C_6$ optionally substituted heterocyclic, $C_3$-$C_6$ optionally substituted aryl, $C_3$-$C_6$ optionally substituted heteroaryl or —NH(CO)—;
$R_3$ is H, $C_1$-$C_4$ alkyl or ($C_1$-$C_4$ alkyl)OH;
$R_{23}$ is H or $C_1$-$C_4$ alkyl, and
$R_{15}$ is hydroxy, phosphonate, or

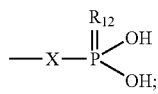
wherein X and $R_{12}$ is O or S;
or a pharmaceutically acceptable salt or tautomer thereof and
a pharmaceutically acceptable carrier.
13. The composition of claim 12 wherein Q is
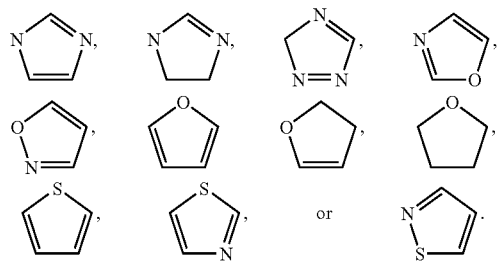
14. The composition of claim 13 wherein $R_{15}$ is hydroxy or
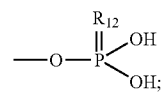
wherein $R_{12}$ is O or S.
15. The composition of claim 14 wherein Q is
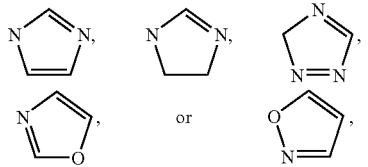
$R_{15}$ is OH;
or a pharmaceutically acceptable salt or tautomer thereof.
* * * * *